(12) United States Patent
Swidorski et al.

(10) Patent No.: US 9,249,180 B2
(45) Date of Patent: Feb. 2, 2016

(54) C-3 ALKYL AND ALKENYL MODIFIED BETULINIC ACID DERIVATIVES

(71) Applicant: BRISTOL-MYERS SQUIBB COMPANY, Princeton, NJ (US)

(72) Inventors: Jacob Swidorski, Southington, CT (US); Yan Chen, Wallingford, CT (US); Sing-Yuen Sit, Meriden, CT (US); Nicholas A. Meanwell, East Hampton, CT (US); Alicia Regueiro-Ren, Middletown, CT (US); Jie Chen, Madison, CT (US); Zheng Liu, Beacon Falls, CT (US); Richard A. Hartz, Middletown, CT (US); Li Xu, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 128 days.

(21) Appl. No.: 14/186,533

(22) Filed: Feb. 21, 2014

(65) Prior Publication Data

US 2014/0243298 A1 Aug. 28, 2014

Related U.S. Application Data

(60) Provisional application No. 61/768,630, filed on Feb. 25, 2013.

(51) Int. Cl.
*A61K 31/56* (2006.01)
*A61K 31/58* (2006.01)
(Continued)

(52) U.S. Cl.
CPC ............. *C07J 53/002* (2013.01); *A61K 31/568* (2013.01); *A61K 31/58* (2013.01); *C07J 63/008* (2013.01)

(58) Field of Classification Search
CPC ........ C07J 63/008; A61K 31/56; A61K 31/58
USPC ...................... 514/169, 176; 540/47; 552/510
See application file for complete search history.

(56) References Cited

U.S. PATENT DOCUMENTS 5,679,828 A 10/1997 Lee et al.
6,369,101 B1 4/2002 Carlson
(Continued)

FOREIGN PATENT DOCUMENTS

WO WO 2006/053255 A2 5/2006
WO WO 2009/100532 A1 8/2009
WO WO 2011/007230 A2 1/2011

OTHER PUBLICATIONS

Blair, W.S. et al., "HIV-1 entry—an expanding portal for drug discovery", Drug Discovery Today, vol. 5, No. 5, pp. 183-194 (2000).
(Continued)

*Primary Examiner* — Barbara P Badio
(74) *Attorney, Agent, or Firm* — John F. Levis

(57) ABSTRACT

Compounds having drug and bio-affecting properties, their pharmaceutical compositions and methods of use are set forth. In particular, alkyl and alkenyl C-3 modified betulinic acid derivatives that possess unique antiviral activity are provided as HIV maturation inhibitors, as represented by compounds of Formulas I, II, III and IV:

a compound of Formula I

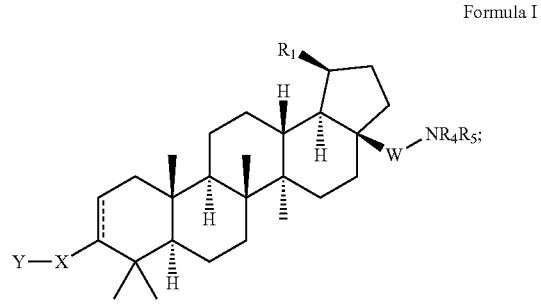

Formula I a compound of Formula II

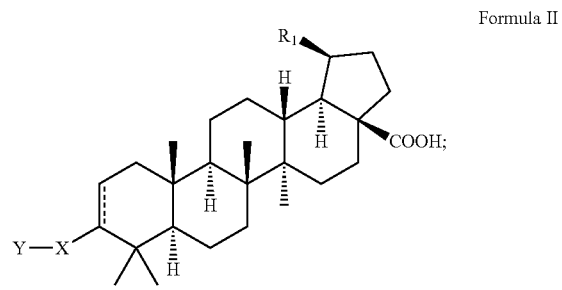

Formula II a compound of Formula III

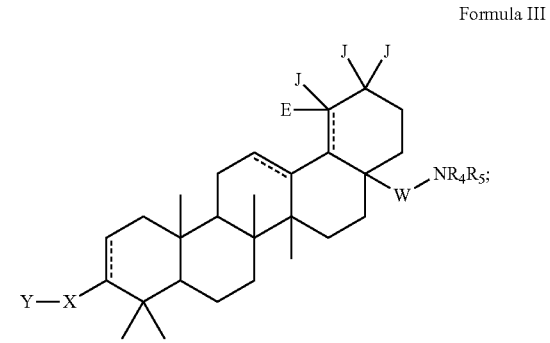

Formula III and a compound of Formula IV

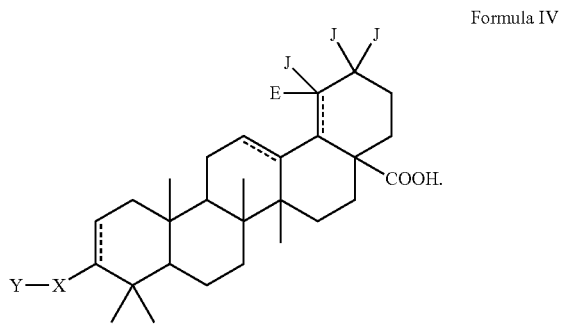

Formula IV

The compounds are useful for the treatment of HIV and AIDS.

13 Claims, No Drawings

(51) Int. Cl.
*C07J 53/00* (2006.01)
*C07J 63/00* (2006.01)
*A61K 31/568* (2006.01)

(56) References Cited

U.S. PATENT DOCUMENTS

| | | | |
|---|---|---|---|
| 7,354,924 | B2 | 4/2008 | Wang et al. |
| 7,365,221 | B2 | 4/2008 | Allaway et al. |
| 7,745,625 | B2 | 6/2010 | Ueda et al. |
| 8,748,415 | B2 | 6/2014 | Regueiro-Ren et al. |
| 8,754,068 | B2 | 6/2014 | Regueiro-Ren et al. |
| 8,802,661 | B2 | 8/2014 | Regueiro-Ren et al. |
| 8,846,647 | B2 | 9/2014 | Regueiro-Ren et al. |
| 8,889,854 | B2 | 11/2014 | Sin et al. |
| 2005/0239748 | A1 | 10/2005 | Power et al. |
| 2008/0207573 | A1 | 8/2008 | Yager et al. |

OTHER PUBLICATIONS

Evers, M. et al., "Betulinic Acid Derivatives: A New Class of Human Immunodeficiency Virus Type 1 Specific Inhibitors with a New Mode of Action," J. Med. Chem., 39, pp. 1056-1068 (1996).

Hotoda, H., "Small-molecule inhibitors of HIV-1 entry via chemokine receptors", Drugs of the Future, vol. 24, No. 12, pp. 1355-1362 (1999).

Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).

Kashiwada Y., et al., "Synthesis and Anti-HIV Activity of 3-Alkylamido-3-deoxy-betulinic Acid Derivatives," Chem. Pharm. Bull., 48, 9, pp. 1387-1390 (2000).

Ma, C-m. et al., "Chemical Modification of Oleanene Type Triterpenes and Their Inhibitory Activity against HIV-1 Protease Dimerization," Chem. Pharm. Bull., 48, 11, pp. 1681-1688 (2000).

Ma, C-m. et al., "Inhibitory Effects of Triterpene-Azidothymidine Conjugates on Proliferation of Human Immunodeficiency Virus Type 1 and Its Protease," Chem. Pharm. Bull., 50, 6, pp. 877-880 (2002).

Meanwell, N.A. et al., "Inhibitors of the entry of HIV into host cells", Current Opinion in Drug Discovery & Development, vol. 6, No. 4, pp. 451-461 (2003).

Pokrovskii, A.G. et al., "Synthesis of derivatives of plant triterpenes and study of their antiviral and immunostimulating activity", Khimiya y Interesakh Ustoichivogo Razvitiya, vol. 9, No. 3, pp. 485-491 (2001) (English abstract).

Qian, K. et al., "Anti-AIDS agents. 78. Design, Synthesis, Metabolic Stability Assessment, and Antiviral Evaluation of Novel Betulinic Acid Derivatives as Potent Anti-Human Immunodeficiency Virus (HIV) Agents," J. Med. Chem., 52, pp. 3248-3258 (2009).

Sodroski, J.G., "HIV-1 Entry Inhibitors in the Side Pocket: Minireview", Cell, vol. 99, pp. 243-246 (1999).

Sun, I-C., "Plant-derived Terpenoids and Analogues as Anti-HIV Agents," Current Topics in Medicinal Chemistry, 3, pp. 155-169 (2003).

C-3 ALKYL AND ALKENYL MODIFIED BETULINIC ACID DERIVATIVES

CROSS REFERENCE TO RELATED APPLICATION

This application claims the priority of U.S. provisional application Ser. No. 61/768,630 filed Feb. 25, 2013 which is herein incorporated by reference.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains-3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. Nos. 7,354,924 and 7,745,625 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., "Synthesis of derivatives of plant triterpenes and study of their antiviral and immunostimulating activity," Khimiya y Interesakh Ustoichivogo Razvitiya, Vol. 9, No. 3, pp. 485-491 (2001) (English abstract)).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitle "MODIFIED C-3 BETULINIC ACID DERIVATIVES AS HIV MATURATION INHIBITORS" U.S. Ser. No. 13/151,706 filed on Jun. 2, 2011 (now US 2012-0142707) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (now US 2012-0142653). Reference is also made to the application entitle "C-28 AMINES OF C-3 MODIFIED BETULINIC ACID DERIVATIVES AS HIV MATURATION INHIBITORS" U.S. Ser. No. 13/359,680, filed on Jan. 27, 2012 (now US 2013-0029954). In addition, reference is made to the application entitled "C-17 AND C-3 MODIFIED TRITERPENOIDS WITH HIV MATURATION INHIBITORY ACTIVITY" U.S. Ser. No. 13/359,727 filed on Jan. 27, 2012 (now US 2013-0035318), and to the application entitled "C-17 BICYCLIC AMINES OF TRITERPENOIDS WITH HIV MATURATION INHIBITORY ACTIVITY", U.S. Ser. No. 61/643,483 filed on May 7, 2012, and to the application entitled "C-19 MODIFIED TRIPERPENOIDS WITH HIV MATURATION INHIBITORY ACTIVITY", U.S. Ser. No. 13/799,479 filed on Mar. 13, 2013 (now US 2013-0296554).

What is now needed in the art are new compounds which are useful as HIV maturation inhibitors, as well as new pharmaceutical compositions containing these compounds.

SUMMARY OF THE INVENTION

The present invention provides compounds of Formulas I, II, III and IV below, including pharmaceutically acceptable salts thereof, their pharmaceutical formulations, and their use in patients suffering from or susceptible to a virus such as HIV. The compounds of Formulas I, II, III and IV are effective antiviral agents, particularly as inhibitors of HIV. They are useful for the treatment of HIV and AIDS.

One embodiment of the present invention is directed to a compound, including pharmaceutically acceptable salts thereof, which is selected from the group of:

a compound of Formula I

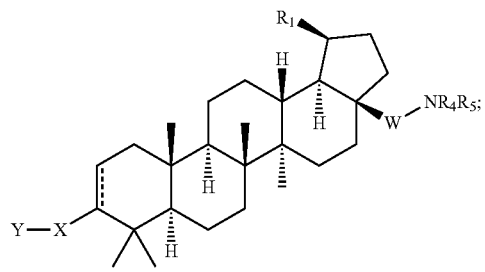

Formula I a compound of Formula II

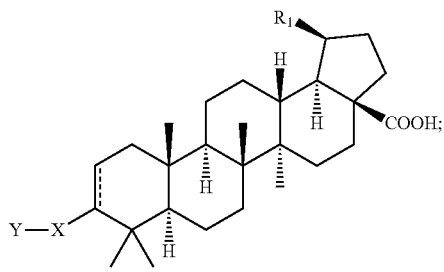

Formula II a compound of Formula III

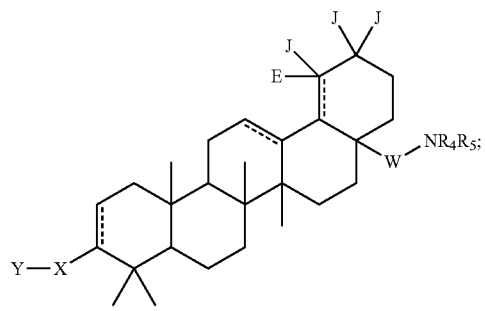

Formula III and a compound of Formula IV

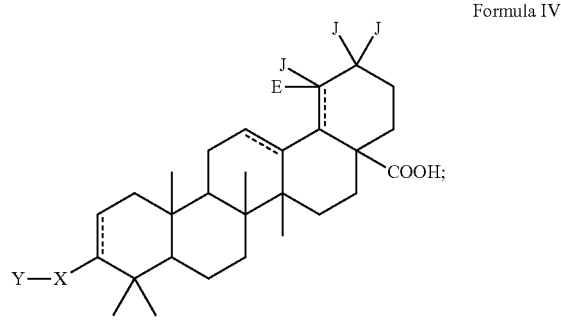

Formula IV wherein $R_1$ is isopropenyl or isopropyl;

J and E are independently —H or —$CH_3$, and E is absent when the double bond is present;

X is selected from the group of —$C_{0-10}$ alkyl, —$C_{2-10}$ alkenyl, —$C_{4-10}$ alkadienyl,

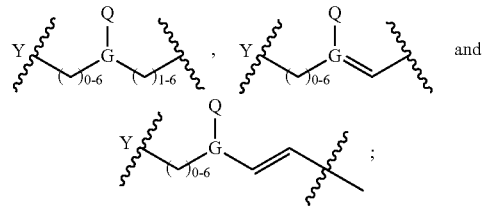 and wherein G is selected from the group of $C_{3-9}$ cycloalkyl, aryl, heteroaryl, fused bicycle and

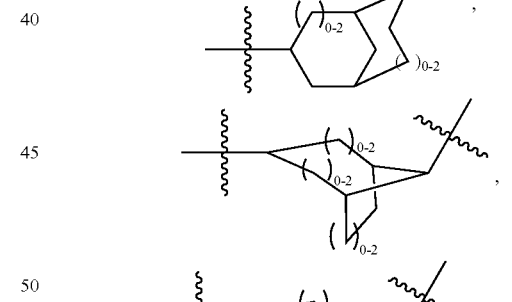

, and

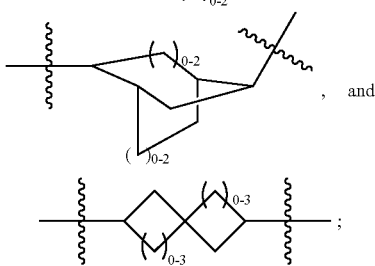

;

wherein X can be further substituted with A, wherein A is at least one member selected from the group of -halo, —$OR_2$, —$C_{1-6}$ alkyl, —$C_{1-6}$ alkylsubstituted alkyl, —$C_{3-9}$cycloalkyl, —$C_{1-6}$ alkyl-$Q_0$, —$NR_2R_2$, —NHCOO$R_3$, —COO$R_2$ and —CON$R_2R_2$;

Q and $Q_0$ are selected from the group of -halo, —$OR_2$, —$C_{1-6}$ alkyl, —$C_{1-6}$ alkylsubstituted alkyl, —$C_{3-9}$cycloalkyl, —$NR_2R_2$, —NHCOO$R_3$, —COO$R_2$ and —CON$R_2R_2$;

$R_2$ is —H, —$C_{1-6}$ alkyl, -alkylsubstituted $C_{1-6}$ alkyl or -arylsubstituted $C_{1-6}$ alkyl;

Y is selected from the group of —$COOR_2$, —C(O)$NR_2SO_2R_3$, —C(O)NHSO$_2$NR$_2$R$_2$, —NR$_2$SO$_2$R$_3$, —SO$_2$NR$_2$R$_2$, —SO$_2$NR$_2$C(O)R$_3$, -tetrazole, —C(O)NHCN and —C(O)NHOR$_2$, W is absent, —CH$_2$ or —CO;

$R_3$ is —$C_{1-6}$ alkyl, -alkylsubstituted-$C_{1-6}$ alkyl, —$C_{3-6}$ cycloalkyl or $C_{1-6}$ alkyl-$C_{3-6}$ cycloalkyl;

$R_4$ is selected from the group of —H, —$C_{1-6}$ alkyl, —$C_{1-6}$ alkyl-C(OR$_3$)$_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-Q$_1$, —$C_{1-6}$ alkyl-$C_{3-6}$ cycloalkyl-Q$_1$, aryl, heteroaryl, substituted heteroaryl, —COR$_6$, —COCOR$_6$, —SO$_2$R$_7$, —SO$_2$NR$_2$R$_2$,

[piperidine with COOR$_2$ on N], and [piperidine with R$_2$ on N, ethyl substituent], with the proviso that R$_4$ or R$_5$ cannot be —COR$_6$ or —COCOR$_6$ when W is CO;

wherein Q$_1$ is selected from the group of heteroaryl, substituted heteroaryl, halogen, —CF$_3$, —OR$_2$, —COOR$_2$, —NR$_8$R$_9$, —CONR$_{10}$R$_{11}$ and —SO$_2$R$_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-NR$_8$R$_9$, —COR$_{10}$, —COR$_6$, —COCOR$_6$, —SO$_2$R$_7$ and —SO$_2$NR$_2$R$_2$;

with the proviso that only one of R$_4$ or R$_5$ can be selected from the group of —COR$_6$, —COCOR$_6$, —SO$_2$R$_7$ and —SO$_2$NR$_2$R$_2$;

or when W is absent or is CH$_2$, then R$_4$ and R$_5$ can be taken together with the adjacent N to form

[aziridine ring];

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-Q$_2$, —$C_{1-6}$ alkyl-Q$_2$, —$C_{1-6}$ alkyl-substitutedalkyl-Q$_2$, —$C_{3-6}$ cycloalkyl-Q$_2$, aryl-Q$_2$, —NR$_{13}$R$_{14}$, and —OR$_{15}$;

wherein Q$_2$ is selected from the group of aryl, heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

$R_7$ is selected from the group of —$C_{1-6}$ alkyl, —$C_{1-6}$ substituted alkyl, —$C_{3-6}$ cycloalkyl, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-Q$_2$, and —COOR$_3$, and R$_8$ and R$_9$ can also be independently selected from the group of

[pyrrolidine with SO$_2$Me on N] and [tetrahydrothiophene SO$_2$], or R$_8$ and R$_9$ are taken together with the adjacent N to form a cycle selected from the group of:

[various heterocyclic structures including piperidine-R$_{16}$, morpholine variants with R$_2$, piperazine-R$_{12}$, sulfone-containing rings, piperidone-R$_{16}$, thiomorpholine, isothiazolidine dioxide, difluoropiperidine, difluoropyrrolidine-R$_{16}$, pyrrolidine-R$_{16}$, pyrrolidinone-R$_{16}$, oxazolidinone-R$_{16}$, thiazolidine dioxide, chloro-benzoxazinone, piperidinyl sulfone-R$_7$ and azaspiro-oxetane];

with the proviso that only one of R$_8$ or R$_9$ can be —COOR$_3$;

$R_{10}$ and $R_{11}$ are independently selected from the group of —H, —$C_{1-6}$ alkyl, —$C_{1-6}$ substituted alkyl and —$C_{3-6}$ cycloalkyl, or R$_{10}$ and R$_{11}$ are taken together with the adjacent N to form a cycle such as

[methylpyrrolidine];

$R_{12}$ is selected from the group of —$C_{1-6}$ alkyl, —$C_{1-6}$ alkyl-OH; —$C_{1-6}$ alkyl, —$C_{1-6}$ substituted alkyl, —$C_{3-6}$ cycloalkyl, —COR$_7$, —COONR$_{22}$R$_{23}$, —SOR$_7$, and —SONR$_{24}$R$_{25}$;

$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-Q$_3$, —$C_{1-6}$ alkyl-$C_{3-6}$ cycloalkyl-Q$_3$, —$C_{1-6}$ substituted alkyl-Q$_3$ and

[2-methyl-3-hydroxypropanoic acid structure with OH groups], or $R_{13}$ and $R_{14}$ are taken together with the adjacent N to form a cycle selected from the group of:

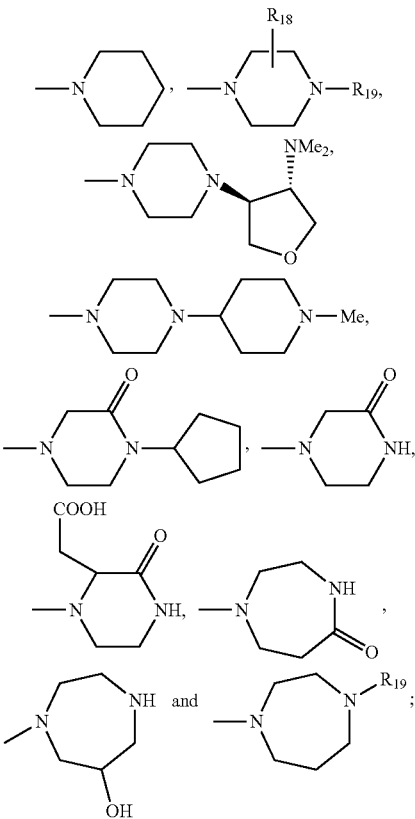

$Q_3$ is selected from the group of heteroaryl, substituted heteroaryl, $-NR_{20}R_{21}$, $-CONR_2R_2$, $-COOR_2$, $-OR_2$, and $-SO_2R_3$;

$R_{15}$ is selected from the group of $-C_{1-6}$ alkyl, $-C_{3-6}$ cycloalkyl, $-C_{1-6}$ substituted alkyl, $-C_{1-6}$ alkyl-$Q_3$, $-C_{1-6}$ alkyl-$C_{3-6}$ cycloalkyl-$Q_3$ and $-C_{1-6}$ substituted alkyl-$Q_3$;

$R_{16}$ is selected from the group of $-C_{1-6}$ alkyl, $-NR_2R_2$, and $-COOR_3$;

$R_{17}$ is selected from the group of $-C_{1-6}$ alkyl, $-COOR_3$, and aryl;

$R_{18}$ is selected from the group of $-COOR_2$ and $-C_{1-6}$ alkyl-$COOR_2$;

$R_{19}$ is selected from the group of $-H$, $-C_{1-6}$ alkyl, $-C_{1-6}$ alkyl-$Q_4$, $-COR_3$, $-COOR_3$, wherein $Q_4$ is selected from the group of $-NR_2R_2$ and $-OR_2$;

$R_{20}$ and $R_{21}$ are independently selected from the group of $-H$, $-C_{1-6}$ alkyl, $-C_{1-6}$ substituted alkyl, $-C_{1-6}$ substituted alkyl-$OR_2$, and $-COR_3$, or $R_{20}$ and $R_{21}$ are taken together with the adjacent N to form a cycle selected from the group of

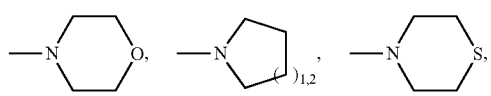

-continued

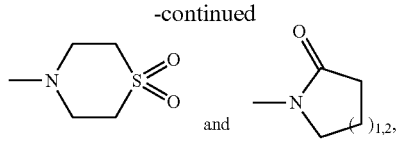

with the proviso that only one of $R_{20}$ or $R_{21}$ can be $-COR_3$;

$R_{22}$ and $R_{23}$ are independently selected from the group of H, $-C_{1-6}$ alkyl, $-C_{1-6}$ substituted alkyl, and $-C_{1-6}$ cycloalkyl, or $R_{22}$ and $R_{23}$ are taken together with the adjacent N to form a cycle selected from the group of

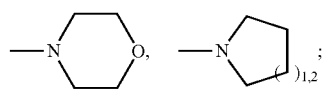

$R_{24}$ and $R_{25}$ are independently from the group of H, $-C_{1-6}$ alkyl, $-C_{1-6}$ substituted alkyl, $-C_{1-6}$ alkyl-$Q_5$, $-C_{1-6}$ cycloalkyl, aryl, substituted aryl, heteroaryl, and substituted heteroaryl; and $Q_5$ is selected from the group of halogen and $SO_2R_3$.

In a further embodiment, there is provided a method for treating mammals infected with a virus, especially wherein said virus is HIV, comprising administering to said mammal an antiviral effective amount of a compound which is selected from the group of compounds of Formulas I, II, III and IV above, and one or more pharmaceutically acceptable carriers, excipients or diluents. Optionally, the compound of Formulas I, II, III and/or IV can be administered in combination with an antiviral effective amount of another-AIDS treatment agent selected from the group of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound which is selected from the group of compounds of Formulas I, II, III and IV, and one or more pharmaceutically acceptable carriers, excipients, and diluents; and optionally in combination with an antiviral effective amount of another AIDS treatment agent selected from the group of: (a) an AIDS antiviral agent; (b) an anti-infective agent; (c) an immunomodulator; and (d) other HIV entry inhibitors.

In another embodiment of the invention there is provided one or more methods for making the compounds of Formulas I, II, III and IV herein.

Also provided herein are intermediate compounds useful in making the compounds of Formulas I, II, III and IV herein.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formulas I, II, III and IV, in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$ fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC(=O)—$ group with said Z being a halogen.

A "C-carboxy" group refers to a —C(=O)O—R" groups, with R" as defined herein.

An "O-carboxy" group refers to a R"C(—O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS(=O)_2—$ groups with Z as defined above.

A "trihalomethanesulfonamido" group refers to a $Z_3CS(=O)_2NR^x—$ group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —$S(=O)_2R''$ group with R" being $(C_{1-6})$alkyl.

A "S-sulfonamido" group refers to a —$S(=O)_2NR^xR^Y$, with $R^X$ and $R^Y$ independently being H or $(C_{1-6})$alkyl.

A "N-Sulfonamido" group refers to a $R''S(=O)_2NR_X—$ group, with $R_x$ being H or $(C_{1-6})$alkyl.

A "O-carbamyl" group refers to a —$OC(=O)NR^xR^y$ group, with $R^x$ and $R^y$ independently being H or $(C_{1-6})$alkyl.

A "N-carbamyl" group refers to a $R^xOC(=O)NR^y$ group, with $R^x$ and $R^y$ independently being H or $(C_{1-6})$alkyl.

A "O-thiocarbamyl" group refers to a —$OC(=S)NR^xR^y$ group, with $R^x$ and $R^y$ independently being H or $(C_{1-6})$alkyl.

A "N-thiocarbamyl" group refers to a $R^xOC(=S)NR^y—$ group, with $R^x$ and $R^y$ independently being H or $(C_{1-6})$alkyl.

An "amino" group refers to an —$NH_2$ group.

A "C-amido" group refers to a —$C(=O)NR^xR^y$ group, with $R^x$ and $R^y$ independently being H or $(C_{1-6})$alkyl.

A "C-thioamido" group refers to a —$C(=S)NR^xR^y$ group, with $R^x$ and $R^y$ independently being H or $(C_{1-6})$alkyl.

A "N-amido" group refers to a $R^xC(=O)NR^3—$ group, with $R^x$ and $R^y$ independently being H or $(C_{1-6})$alkyl.

An "ureido" group refers to a —$NR^xC(=O)NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "amidino" group refers to a $R^xR^yNC(=N)—$ group, with $R^x$ and $R^y$ independently being H or $(C_{1-6})$alkyl.

A "cyano" group refers to a —CN group.

A "silyl" group refers to a —$Si(R'')_3$, with R" being $(C_{1-6})$ alkyl or phenyl.

A "phosphonyl" group refers to a $P(=O)(OR^x)_2$ with Rx being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

A "4, 5, or 6 membered ring cyclic N-lactam" group refers to

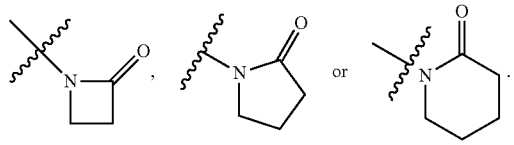

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

The terms "C-3" and "C-28" refer to certain positions of a triterpene core as numbered in accordance with IUPAC rules (positions depicted below with respect to an illustrative triterpene: betulin):

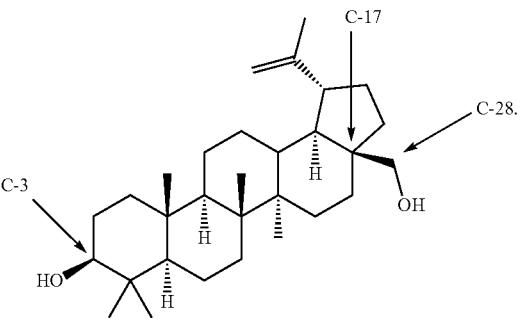

The same numbering is maintained when referring to the compound series in schemes and general descriptions of methods.

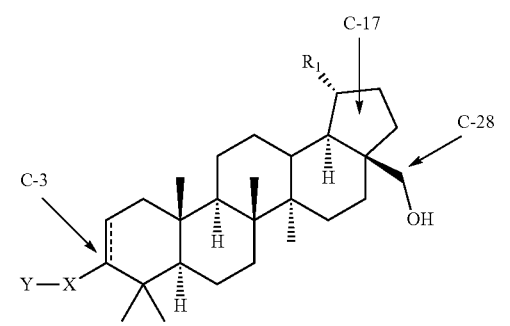

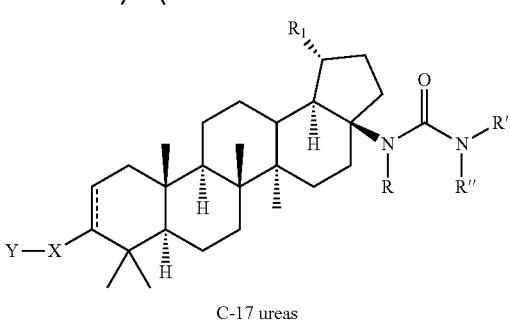

C-17 ureas

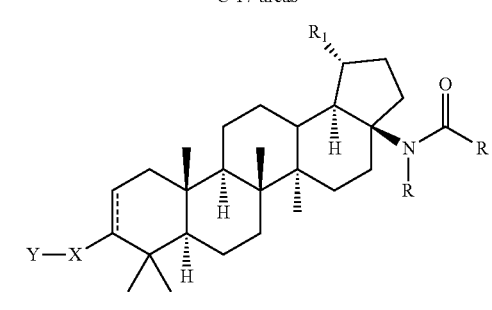

C-17 amides

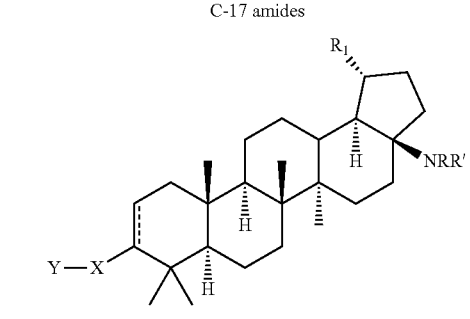

C-17 amines

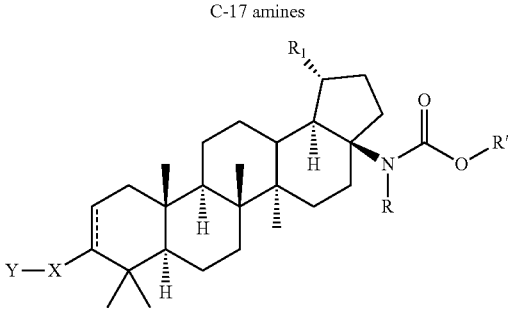

C-17 carbamates

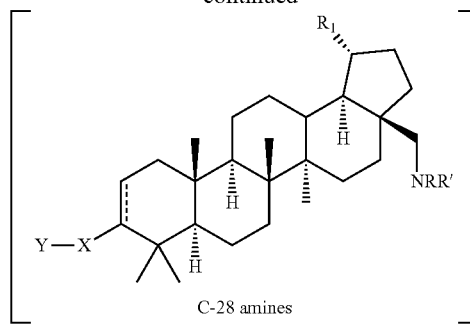

C-28 amines

As set forth above, the invention is directed to a compound, including pharmaceutically acceptable salts thereof, which is selected from the group of:
a compound of Formula I

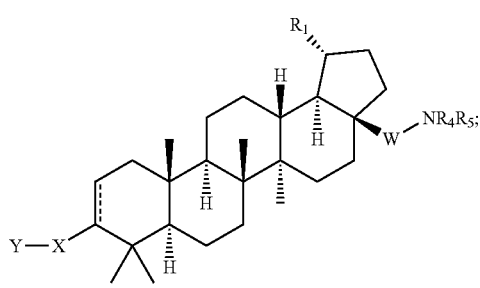

Formula I a compound of Formula II

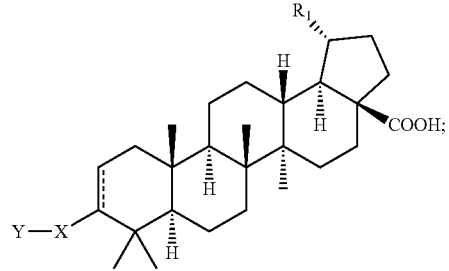

Formula II a compound of Formula III

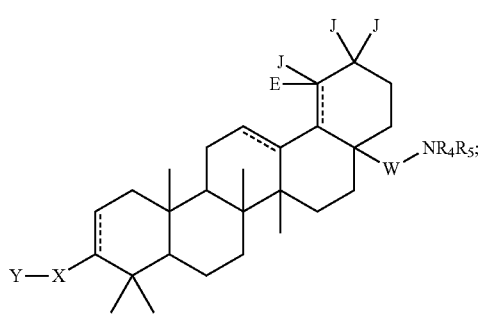

Formula III and a compound of formula IV

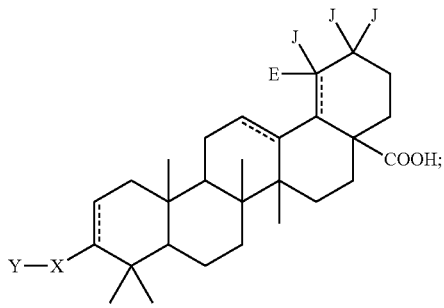

Formula IV wherein $R_1$ is isopropenyl or isopropyl;

J and E are independently —H or —$CH_3$, and E is absent when the double bond is present;

X is selected from the group of —$C_{0-10}$ alkyl, —$C_{2-10}$ alkenyl, —$C_{4-10}$ alkadienyl,

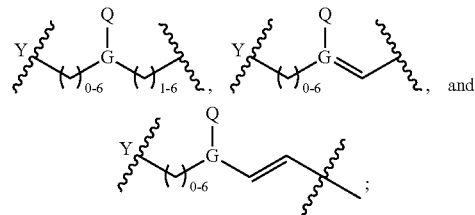

wherein G is selected from the group of $C_{3-9}$ cycloalkyl, aryl, heteroaryl, fused bicycle and

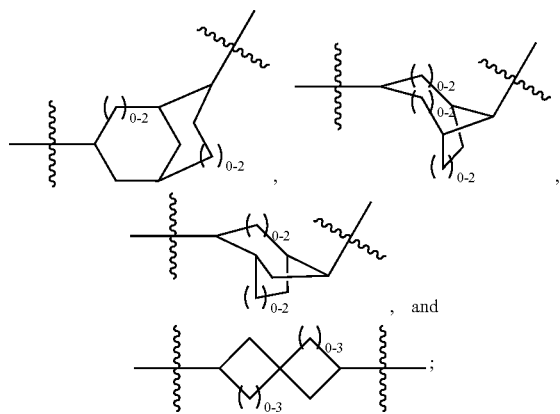

wherein X can be further substituted with A, wherein A is at least one member selected from the group of -halo, —$OR_2$, —$C_{1-6}$ alkyl, —$C_{1-6}$ alkylsubstituted alkyl, —$C_{3-9}$cycloalkyl, —$C_{1-6}$ alkyl-$Q_0$, —$NR_2R_2$, —$NHCOOR_3$, —$COOR_2$ and —$CONR_2R_2$;

Q and $Q_0$ are selected from the group of -halo, —$OR_2$, —$C_{1-6}$ alkyl, —$C_{1-6}$ alkylsubstituted alkyl, —$C_{3-9}$cycloalkyl, —$NR_2R_2$, —$NHCOOR_3$, —$COOR_2$ and —$CONR_2R_2$;

$R_2$ is —H, —$C_{1-6}$ alkyl, -alkylsubstituted $C_{1-6}$ alkyl or -aryl-substituted $C_{1-6}$ alkyl;

Y is selected from the group of —$COOR_2$, —C(O)$NR_2SO_2R_3$, —C(O)$NHSO_2NR_2R_2$, —$NR_2SO_2R_3$, —$SO_2NR_2R_2$, —$SO_2NR_2C(O)R_3$, _tetrazole, —C(O)NHCN and —C(O)$NHOR_2$, W is absent, —$CH_2$ or —CO;

$R_3$ is —$C_{1-6}$ alkyl, -alkylsubstituted-$C_{1-6}$ alkyl, —$C_{3-6}$ cycloalkyl or $C_{1-6}$ alkyl-$C_{3-6}$ cycloalkyl;

$R_4$ is selected from the group of —H, —$C_{1-6}$ alkyl, —$C_{1-6}$ alkyl-$C(OR_3)_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cyclo alkyl-$Q_1$, aryl, heteroaryl, substituted heteroaryl, —$COR_6$, —$COCOR_6$, —$SO_2R_7$, —$SO_2NR_2R_2$,

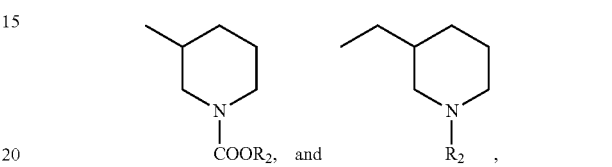

with the proviso that $R_4$ or $R_5$ cannot be —$COR_6$ or —$COCOR_6$ when W is CO;

wherein $Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;

with the proviso that only one of $R_4$ or $R_5$ can be selected from the group of —$COR_6$, —$COCOR_6$, —$SO_2R_7$ and —$SO_2NR_2R_2$;

or when W is absent or is $CH_2$, then $R_4$ and $R_5$ can be taken together with the adjacent N to form

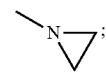

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substitutedalkyl-$Q_2$, —$C_{3-6}$ cycloalkyl-$Q_2$, aryl-$Q_2$, —$NR_{13}R_{14}$, and —$OR_{15}$;

wherein $Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —$C_{1-6}$ alkyl, —$C_{1-6}$ substituted alkyl, —$C_{3-6}$ cycloalkyl, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, and $R_8$ and $R_9$ can also be independently selected from the group of

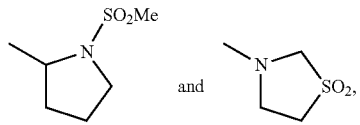

or $R_8$ and $R_9$ are taken together with the adjacent N to form a cycle selected from the group of:

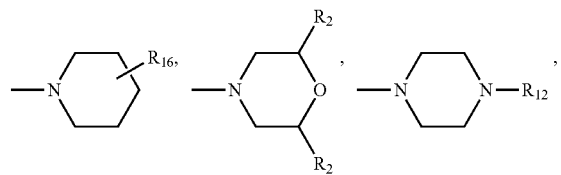

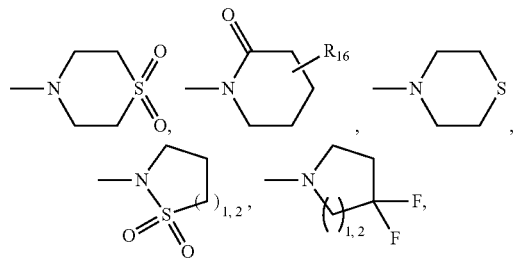

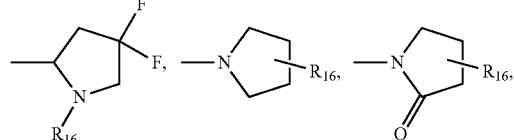

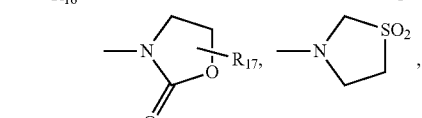

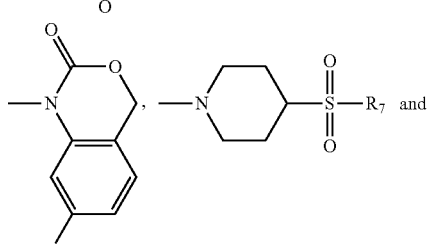

with the proviso that only one of $R_8$ or $R_9$ can be —COOR$_3$;

$R_{10}$ and $R_{11}$ are independently selected from the group of —H, —C$_{1-6}$ alkyl, —C$_{1-6}$ substituted alkyl and —C$_{3-6}$ cycloalkyl, or $R_{10}$ and $R_{11}$ are taken together with the adjacent N to form a cycle such as

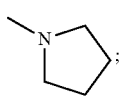

$R_{12}$ is selected from the group of —C$_{1-6}$ alkyl, —C$_{1-6}$ alkyl-OH; —C$_{1-6}$ alkyl, —C$_{1-6}$ substituted alkyl, —C$_{3-6}$ cycloalkyl, —COR$_7$, —COONR$_{22}$R$_{23}$, —SOR$_7$, and —SONR$_{24}$R$_{25}$;

$R_{13}$ and $R_{14}$ are independently selected from the group of —H, —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$, C$_{1-6}$ substituted alkyl-Q$_3$ and

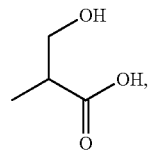

or $R_{13}$ and $R_{14}$ are taken together with the adjacent N to form a cycle selected from the group of:

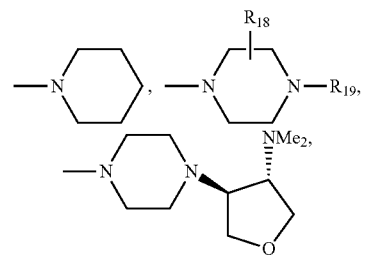

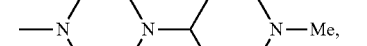

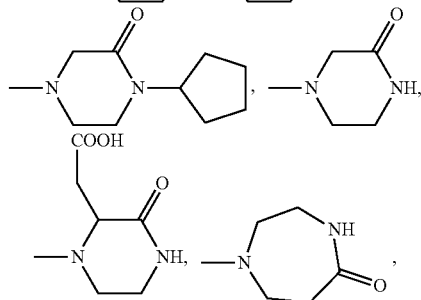

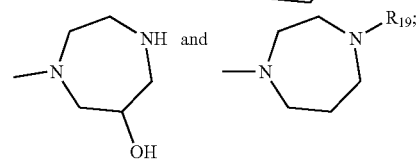

$Q_3$ is selected from the group of heteroaryl, substituted heteroaryl, —NR$_{20}$R$_{21}$, ⁻CONR$_2$R$_2$, —COOR$_2$, —OR$_2$, and —SO$_2$R$_3$;

$R_{15}$ is selected from the group of —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$ and —C$_{1-6}$ substituted alkyl-Q$_3$;

$R_{16}$ is selected from the group of —C$_{1-6}$ alkyl, —NR$_2$R$_2$, and —COOR$_3$;

$R_{17}$ is selected from the group of —C$_{1-6}$ alkyl, —COOR$_3$, and aryl;

$R_{18}$ is selected from the group of —COOR$_2$ and —C$_{1-6}$ alkyl-COOR$_2$;

$R_{19}$ is selected from the group of —H, —C$_{1-6}$ alkyl, —C$_{1-6}$ alkyl-Q$_4$, —COR$_3$, —COOR$_3$, wherein Q$_4$ is selected from the group of —NR$_2$R$_2$ and —OR$_2$;

$R_{20}$ and $R_{21}$ are independently selected from the group of —H, —C$_{1-6}$ alkyl, —C$_{1-6}$ substituted alkyl, —C$_{1-6}$ substituted alkyl-OR$_2$, and —COR$_3$, or $R_{20}$ and $R_{21}$ are taken together with the adjacent N to form a cycle selected from the group of

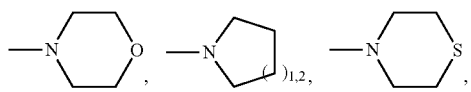

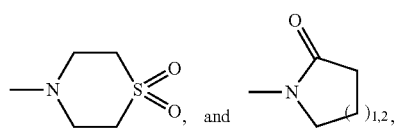

with the proviso that only one of $R_{20}$ or $R_{21}$ can be —$COR_3$;

$R_{22}$ and $R_{23}$ are independently selected from the group of H, —$C_{1-6}$ alkyl, —$C_{1-6}$ substituted alkyl, and —$C_{1-6}$ cycloalkyl, or $R_{22}$ and $R_{23}$ are taken together with the adjacent N to form a cycle selected from the group of

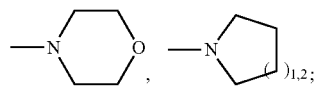

$R_{24}$ and $R_{25}$ are independently from the group of H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl; and $Q_5$ is selected from the group of halogen and $SO_2R_3$.

Preferred are compounds of Formula I.

Further preferred are compounds wherein Y is $COOR_2$. It is also preferred that $R_2$ is —H.

It is also preferred that $R_1$ is isopropenyl.

It is further preferred that W is absent in most embodiments.

Also preferred are compounds, including pharmaceutically acceptable salts thereof, which are selected from the group of:

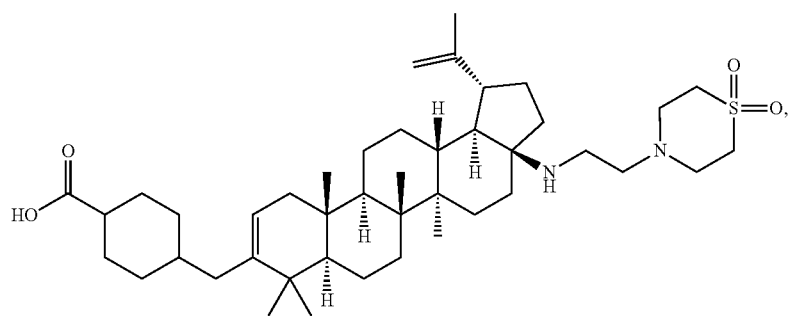

Isomer 1

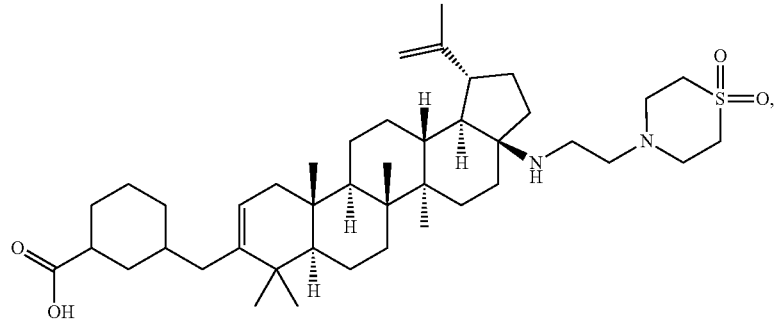

Isomer 2

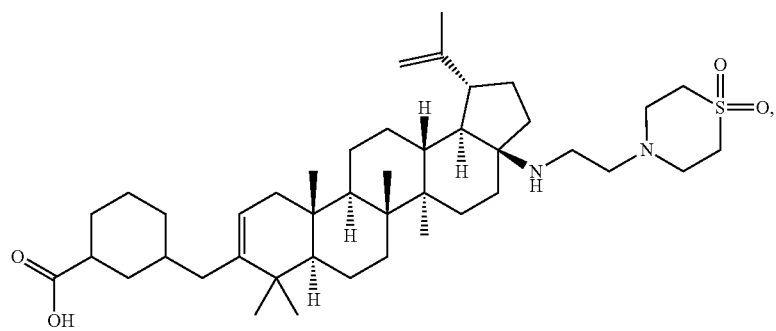

-continued
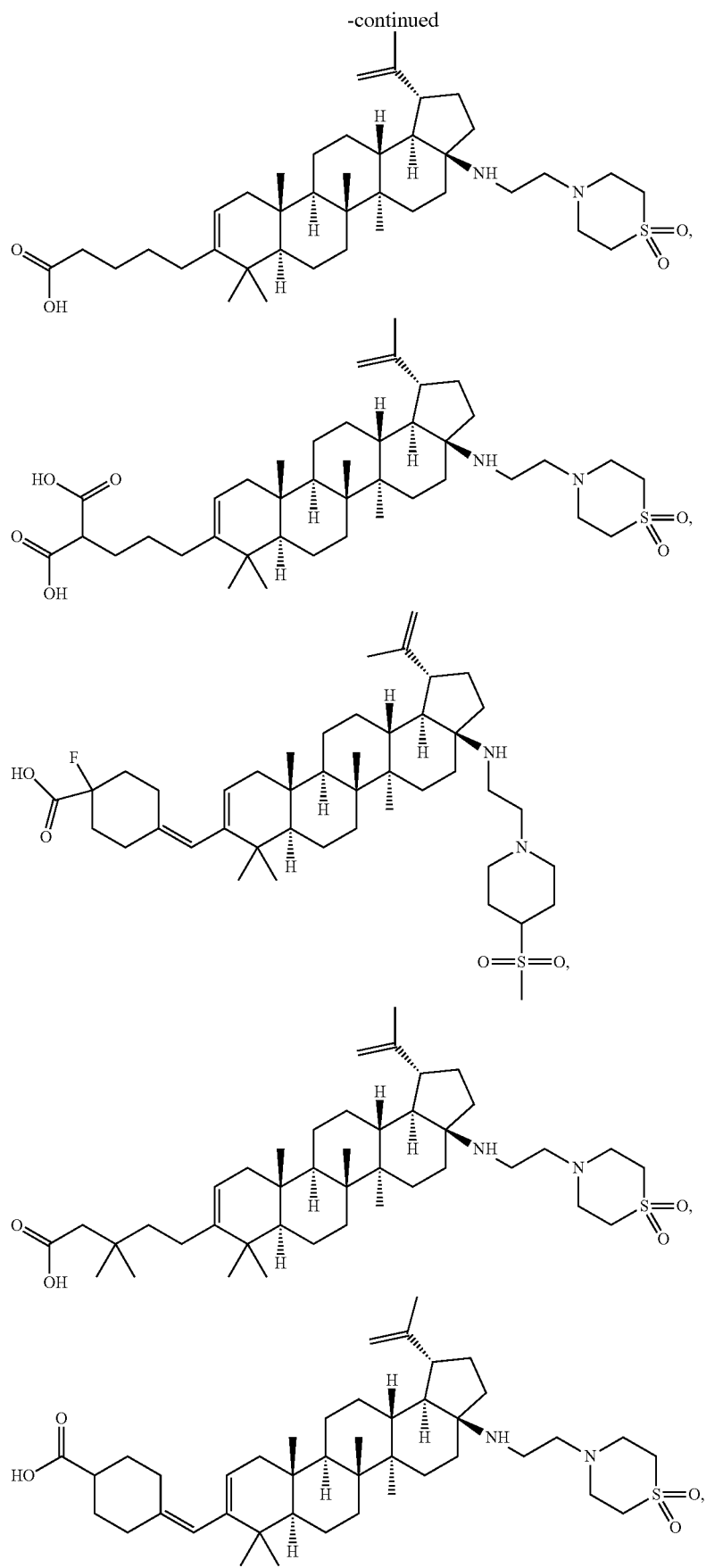

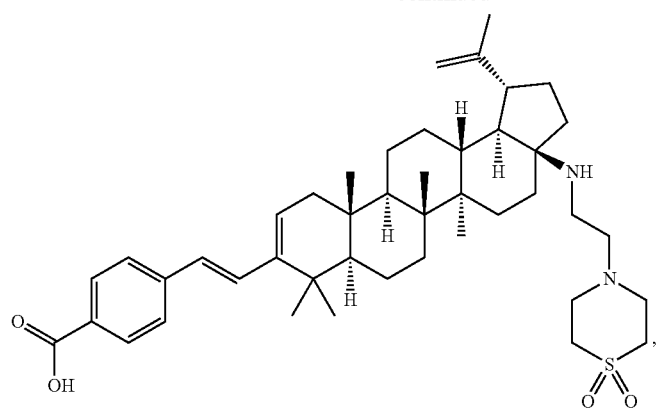
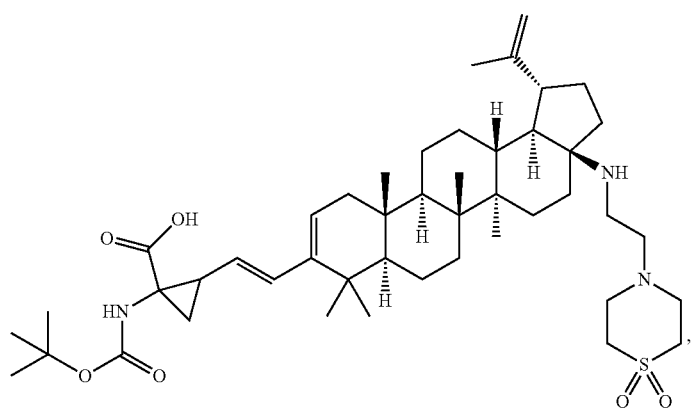
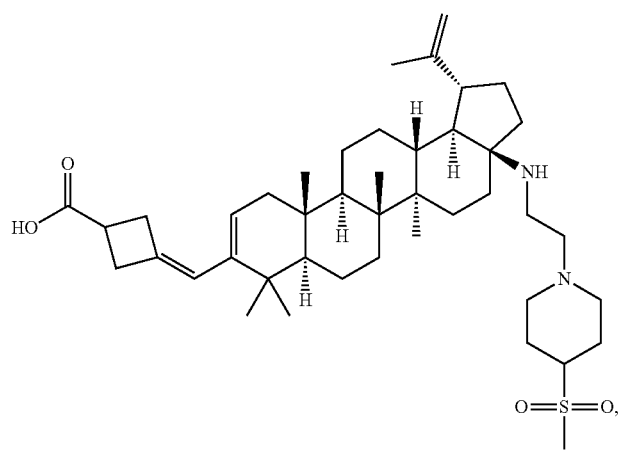
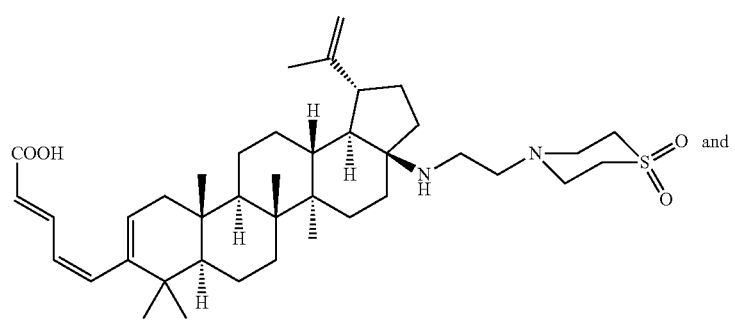

-continued

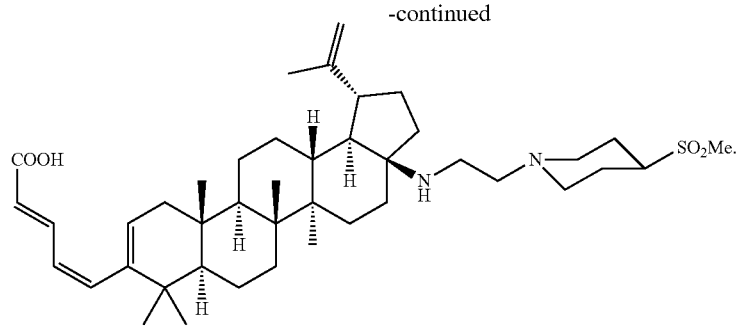

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I, II, III and IV, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
| --- | --- | --- |
| ANTIVIRALS | | |
| 097 | Hoechst/Bayer | HIV infection, AIDS, ARC (non-nucleoside reverse transcriptase (RT) inhibitor) |

-continued

| Drug Name | Manufacturer | Indication |
|---|---|---|
| Amprenavir<br>141 W94<br>GW 141 | Glaxo Wellcome | HIV infection,<br>AIDS, ARC<br>(protease inhibitor) |
| Abacavir (1592U89)<br>GW 1592 | Glaxo Wellcome | HIV infection,<br>AIDS, ARC<br>(RT inhibitor) |
| Acemannan | Carrington Labs<br>(Irving, TX) | ARC |
| Acyclovir | Burroughs Wellcome | HIV infection, AIDS,<br>ARC |
| AD-439 | Tanox Biosystems | HIV infection, AIDS,<br>ARC |
| AD-519 | Tanox Biosystems | HIV infection, AIDS,<br>ARC |
| Adefovir dipivoxil | Gilead Sciences | HIV infection |
| AL-721 | Ethigen<br>(Los Angeles, CA) | ARC, PGL<br>HIV positive, AIDS |
| Alpha Interferon | Glaxo Wellcome | Kaposi's sarcoma,<br>HIV in combination w/Retrovir |
| Ansamycin<br>LM 427 | Adria Laboratories<br>(Dublin, OH)<br>Erbamont<br>(Stamford, CT) | ARC |
| Antibody which<br>Neutralizes pH<br>Labile alpha aberrant<br>Interferon | Advanced Biotherapy<br>Concepts<br>(Rockville, MD) | AIDS, ARC |
| AR177 | Aronex Pharm | HIV infection, AIDS,<br>ARC |
| Beta-fluoro-ddA | Nat'l Cancer Institute | AIDS-associated<br>diseases |
| BMS-234475<br>(CGP-61755) | Bristol-Myers Squibb/<br>Novartis | HIV infection,<br>AIDS, ARC<br>(protease inhibitor) |
| CI-1012 | Warner-Lambert | HIV-1 infection |
| Cidofovir | Gilead Science | CMV retinitis,<br>herpes, papillomavirus |
| Curdlan sulfate | AJI Pharma USA | HIV infection |
| Cytomegalovirus<br>Immune globin | MedImmune | CMV retinitis |
| Cytovene<br>Ganciclovir | Syntex | Sight threatening<br>CMV<br>peripheral CMV<br>retinitis |
| Darunavir | Tibotec-J & J | HIV infection, AIDS, ARC<br>(protease inhibitor) |
| Delaviridine | Pharmacia-Upjohn | HIV infection,<br>AIDS, ARC<br>(RT inhibitor) |
| Dextran Sulfate | Ueno Fine Chem.<br>Ind. Ltd. (Osaka,<br>Japan) | AIDS, ARC, HIV<br>positive<br>asymptomatic |
| ddC<br>Dideoxycytidine | Hoffman-La Roche | HIV infection, AIDS,<br>ARC |
| ddI<br>Dideoxyinosine | Bristol-Myers Squibb | HIV infection, AIDS,<br>ARC; combination<br>with AZT/d4T |
| DMP-450 | AVID<br>(Camden, NJ) | HIV infection,<br>AIDS, ARC<br>(protease inhibitor) |
| Efavirenz<br>(DMP 266, SUSTIVA ®)<br>(−)6-Chloro-4-(S)-<br>cyclopropylethynyl-<br>4(S)-trifluoro-<br>methyl-1,4-dihydro-<br>2H-3,1-benzoxazin-<br>2-one, STOCRINE | Bristol Myers Squibb | HIV infection,<br>AIDS, ARC<br>(non-nucleoside RT<br>inhibitor) |
| EL10 | Elan Corp, PLC<br>(Gainesville, GA) | HIV infection |
| Etravirine | Tibotec/J & J | HIV infection, AIDS, ARC<br>(non-nucleoside<br>reverse transcriptase<br>inhibitor) |

-continued

| Drug Name | Manufacturer | Indication |
|---|---|---|
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |

| Drug Name | Manufacturer | Indication |
|---|---|---|
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDS in development |
| CMX-157 Lipid conjugate of nucleotide tenofovir | Chimerix | HIV infection AIDS |
| GSK1349572 Integrase inhibitor | GSK | HIV infection AIDS |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |

-continued

| Drug Name | Manufacturer | Indication |
|---|---|---|
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |

| Drug Name | Manufacturer | Indication |
| --- | --- | --- |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*, Meanwell, Nicholas A.; Kadow, John F. Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. No. 7,354,924 and US 2005/0209246.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

Abbreviations:
TBDMS=tert-butyldimethylsilane
PTFE=polytetrafluoroethylene
NMO=4-methylmorpholine-N-oxide
THF=tetrahydrofuran
TLC=thin layer chromatography
DCM=dichloromethane
DCE=dichloroethane
TFA=trifluoroacetic acid
LCMS=liquid chromatography mass spectroscopy
Prep=preparative
HPLC=high performance liquid chromatography
DAST=(diethylamino)sulfur trifluoride
TEA=triethylamine
DIPEA=N,N-diisopropylethylamine
HATU=[O-(7-azabenzotriazol-1-yl)-1,1,3,3-tetramethyluronium hexafluorophosphate]
DMAP=dimethylaminopyridine
TMS=trimethylsilyl
NMR=nuclear magnetic resonance
DPPA=diphenyl phosphoryl azide
AIBN=azobisisobutyronitrile
TBAF=tetrabutylammonium fluoride
DMF=dimethylformamide
TBTU=O-(benzotriazol-1-yl)-N,N,N',N'-tetramethyluronium tetrafluoroborate
min=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
$Tf_2NPh$=(trifluoromethylsulfonyl)methanesulfonamide dioxane=1,4-dioxane
PG=protective group
atm=atmosphere(s)
mol=mole(s)
mmol=millimole(s)
mg=milligram(s)
μg=microgram(s)
μl=microliter(s)
μm=micrometer(s)
mm=millimeter(s)

EXAMPLES

The following examples illustrate typical syntheses of the compounds of Formulas I, II, III and IV as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), Acetic-d4 (Acetic Acid d$_4$) ($\delta_H$ 11.6, 2.07), DMSO mix or DMSO-D6_CDCl$_3$ (($_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

Abbreviations

One or more of the following abbreviations, most of which are conventional abbreviations well known to those skilled in the art, may be used throughout the description of the examples:

Bz$_2$O=benzoic anhydride
TBTU=O-(benzotriazol-1-yl)-N,N,N',N'-tetramethyluronium tetrafluoroborate
HATU=2-(1H-7-azabenzotriazol-1-yl)-1,1,3,3-tetramethyluronium hexafluorophosphate methanaminium
DCE=dichloroethane
DCM=dichloromethane
CDI=carbonyl diimidazole
prep. HPLC=preparative high performance liquid chromatography
rt=room temperature
LDA=Lithium diisopropylamine
DIPEA=diisopropylethylamine
DMAP=4-dimethylaminopyridine
DMSO=dimethylsulfoxide
THF=tetrahydrofuran
KHMDS=potassium bis(trimethylsilyl)amide
min=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=millimole(s)
mg=milligram(s)
μg=microgram(s)
μl=micro liter(s)
μm=micrometer(s)
mm=millimeter(s)
HOAc=acetic acid
MeOH=methanol
TBDMSCl=tert-butyldimethylsilyl chloride
DMF=N,N-dimethylformamide
TBAF=tetrabutylammonium fluoride LC/MS Methods:

Method 1
Start % B=0, Final % B=100 over 2 minute gradient, hold at 100% B
Flow Rate=1 mL/min
Wavelength=220 nm
Solvent A=90% water, 10% acetonitrile, 0.1% TFA
Solvent B=10% water, 90% acetonitrile, 0.1% TFA
Column=Phenomenex Luna C18, 3 μm, 2.0×30 mm Method 2
Start % B=0, Final % B=100 over 2 minute gradient, hold at 100% B
Flow Rate=1 mL/min
Wavelength=220 nm
Solvent A=95% Water, 5% methanol/10 mM ammonium acetate
Solvent B=5% Water, 95% methanol/10 mM ammonium acetate
Column=Phenomenex Luna C18, 3 μm, 2.0×30 mm Method 3
Start % B=0; Final % B=100 over 2 minute gradient, hold at 100% B
Flow Rate=1 mL/min
Detector Wavelength=220 nm
Solvent A=90% water, 10% methanol, 0.1% TFA
Solvent B=10% water, 90% methanol, 0.1% TFA
Column=Phenomenex Luna C18, 3 μm, 2.0×30 mm Method 4
Start % B=20; Final % B=100 over 2 minute gradient, hold at 100% B
Flow Rate=0.8 mL/min
Detector Wavelength=220 nm
Solvent A=90% water, 10% methanol, 0.1% TFA
Solvent B=10% water, 90% methanol, 0.1% TFA
Column=Xbridge Phenyl, 2.5 μm, 2.1×50 mm Method 5:
Start % B=30, Final % B=100 over 2 minute gradient
Flow Rate=0.8 ml/min
Wavelength=220
Solvent A=10% MeOH-90% H$_2$O-0.1% TFA
Solvent B=90% MeOH-10% H$_2$O-0.1% TFA
Column=Xbridge Phenyl 2.1×50 mm 2.5 μm
Method 6
Start % B=0, Final % B=100 over 2 minute gradient, hold at 100% B
Flow Rate=4 mL/min
Wavelength=220 nm
Solvent A=95% Water, 5% Acetonitrile/10 mM ammonium acetate
Solvent B=5% Water, 95% Acetonitrile/10 mM ammonium acetate
Column=Phenomenex Luna, 3.0×50 mm, S10
Prep HPLC
Method 1
Start % B=20 Final % B=100 over 15 minute gradient, hold at 100% B
Flow Rate=40 mL/min
Solvent A=10% acetonitrile, 90% H$_2$O, 0.1% TFA
Solvent B=90% acetonitrile, 10% H$_2$O, 0.1% TFA
Column=Waters Sunfire 30×100 mm 5 μm
Method 2
Start % B=15 Final % B=90 over 15 minute gradient, hold at 100%
Flow Rate=40 mL/min
Solvent A=10% acetonitrile, 90% H$_2$O, 0.1% TFA
Solvent B=90% acetonitrile, 10% H$_2$O, 0.1% TFA
Column=Waters-Sunfire 30×100 mm 5 μm
Method 3
Start % B=10 Final % B=85 over 20 minute gradient, hold at 100%
Flow Rate=40 mL/min
Solvent A=10% acetonitrile, 90% H$_2$O, 0.1% TFA
Solvent B=90% acetonitrile, 10% H$_2$O, 0.1% TFA
Column=Waters-Sunfire 30×100 mm 5 μm
Method 4
Start % B=10; Final % B=100 over 10 minute gradient, hold at 100% B
Flow Rate=25 mL/min
Solvent A=5% acetonitrile, 95% H$_2$O-10 mM Ammonium Actetate
Solvent B=95% acetonitrile, 5% H$_2$O-10 mM Ammonium Actetate
Column=X-bridge OBD prep shield RP18 19×100 mm 5 μm
Method 5
Start % B=15; Final % B=95 over 15 minute gradient, hold at 100%
Flow Rate=40 mL/min
Solvent A=10% acetonitrile, 90% H$_2$O-0.1% TFA
Solvent B=90% acetonitrile, 10% H$_2$O-0.1% TFA
Column=Waters-Sunfire 30×100 mm 5 μm
Method 6
Start % B=25; Final % B=90 over 15 minute gradient, hold at 100%
Flow Rate=40 mL/min
Solvent A=10% acetonitrile, 90% H2O-0.1% TFA
Solvent B=90% acetonitrile, 10% H2O-0.1% TFA
Column=Waters-Sunfire 30×100 mm 5 μm
Method 7
Start % B=20; Final % B=85 over 15 minute gradient, hold at 100%
Flow Rate=40 mL/min
Solvent A=10% acetonitrile, 90% H2O-0.1% TFA
Solvent B=90% acetonitrile, 10% H2O-0.1% TFA
Column=Waters-Sunfire 30×100 mm 5 μm
Method 8
Start % B=25; Final % B=100 over 20 minute gradient, hold at 100%
Flow Rate=40 mL/min
Solvent A=10% acetonitrile, 90% H2O-0.1% TFA
Solvent B=90% acetonitrile, 10% H2O-0.1% TFA
Column=Waters-Sunfire 30×100 mm 5 μm
Method 9
Start % B=30 Final % B=100 over 12 minute gradient, hold at 100% B
Flow Rate=40 mL/min
Solvent A=10% acetonitrile, 90% H$_2$O, 0.1% TFA
Solvent B=90% acetonitrile, 10% H$_2$O, 0.1% TFA
Column=Waters Sunfire 30×100 mm, 5 μm
Method 10
Start % B=50 Final % B=100 over 20 minute gradient, hold at 100% B
Flow Rate=20 mL/min
Solvent A=5% acetonitrile, 95% H$_2$O, 10 mM Ammonium Actetate
Solvent B=95% acetonitrile, 5% H$_2$O, 10 mM Ammonium Actetate
Column=XBridge C18 19×200 mm, 5 μm
Method 11
Start % B=60 Final % B=100 over 20 minute gradient, hold at 100% B
Flow Rate=20 mL/min
Solvent A=5% acetonitrile, 95% H$_2$O, 10 mM Ammonium Actetate
Solvent B=95% acetonitrile, 5% H$_2$O, 10 mM Ammonium Actetate
Column=XBridge C18 19×200 mm, 5 μm
Method 12
Start % B=50 Final % B=90 over 20 minute gradient, hold at 100% B
Flow Rate=20 mL/min
Solvent A=5% acetonitrile, 95% H$_2$O, 10 mM Ammonium Actetate
Solvent B=95% acetonitrile, 5% H$_2$O, 10 mM Ammonium Actetate
Column=XBridge C18 19×200 mm, 5 μm
Method 13
Start % B=60 Final % B=100 over 15 minute gradient, hold at 100% B
Flow Rate=20 mL/min
Solvent A=5% acetonitrile, 95% H$_2$O, 10 mM Ammonium Actetate
Solvent B=95% acetonitrile, 5% H$_2$O, 10 mM Ammonium Actetate
Column=XBridge C18 19×200 mm, 5 μm Synthesis of Key Intermediates:

Key intermediate 1 was prepared by the following methods:

Method 1: Intermediate 1

Preparation of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate

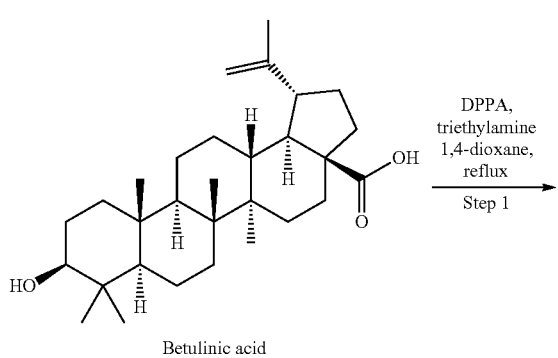

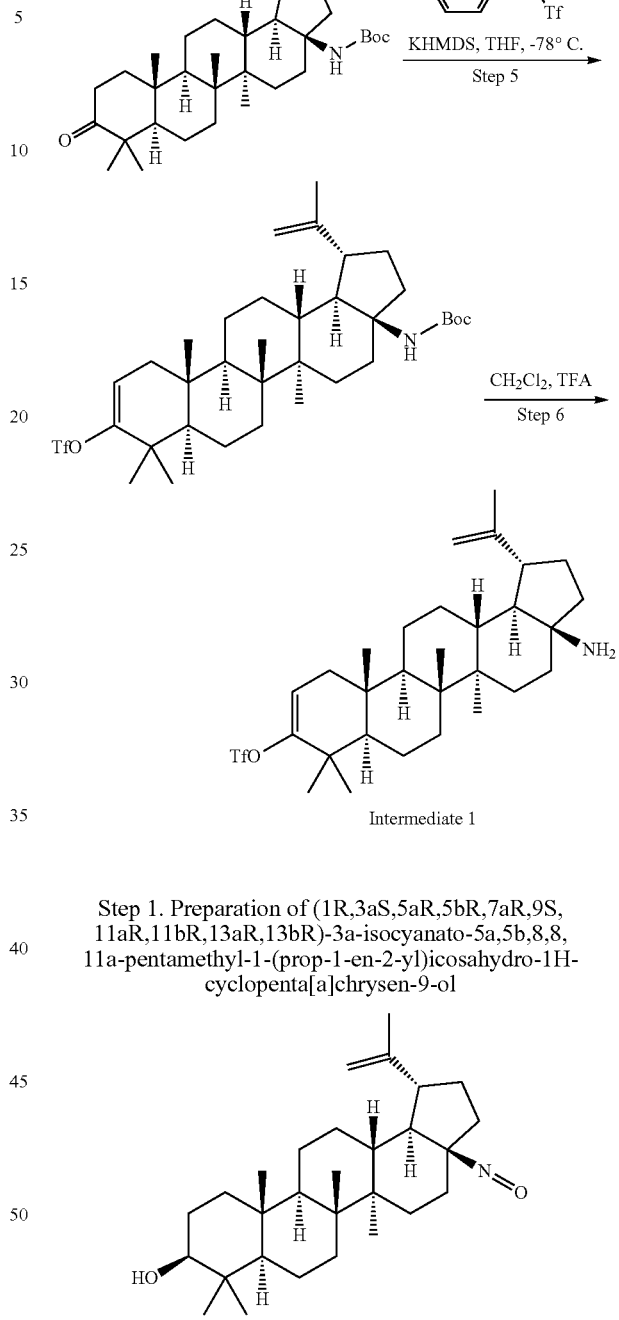

Step 1. Preparation of (1R,3aS,5aR,5bR,7aR,9S,11aR,11bR,13aR,13bR)-3a-isocyanato-5a,5b,8,8,11a-pentamethyl-1-(prop-1-en-2-yl)icosahydro-1H-cyclopenta[a]chrysen-9-ol

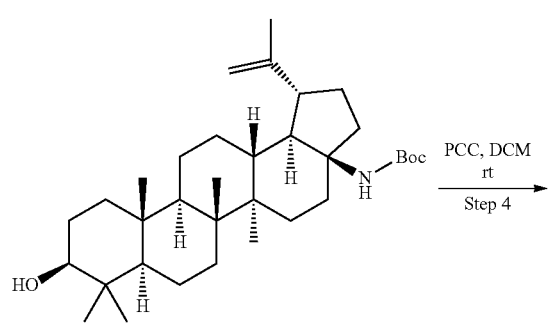

To a suspension of betulinic acid (10 g, 21.90 mmol) in 1,4-dioxane (100 mL) was added triethylamine (9.16 mL, 65.7 mmol) and diphenyl phosphorazidate (7.08 mL, 32.8 mmol). The mixture was heated to reflux. Upon heating, all solids dissolved. After heating the mixture for 26 h, the mixture was cooled to rt and was concentrated under reduced pressure. The residue was diluted with 100 mL of water and was extracted with dichloromethane (3×100 mL). The combined organic layers were dried with sodium sulfate. The drying agent was removed by filtration and the filtrate was concentrated under reduced pressure. The residue was purified by flash chromatography using a 0-15% EtOAc in hexanes gradient and a Thomson 240 g silica gel column. The fractions containing the expected product were combined and concentrated under reduced pressure. A second batch of less-pure product was concentrated and was repurified using a Thomson 240 g column and the same gradient. The fractions containing the expected product were combined with the first batch to give the title compound as a white solid (7.76 g, 17.10 mmol, 78% yield). $^1$H NMR (400 MHz, chloroform-d) δ=4.75 (s, 1H), 4.67-4.62 (m, 1H), 3.20 (dt, J=11.3, 5.6 Hz, 1H), 2.55 (td, J=10.9, 5.9 Hz, 1H), 2.17-2.03 (m, 1H), 1.92-1.76 (m, 5H), 1.69 (s, 3H), 1.06 (s, 3H), 0.98 (s, 3H), 0.95 (s, 3H), 0.85 (s, 3H), 0.78 (s, 3H), 1.74-0.66 (m, 19H).

Step 2. Preparation of (1R,3aS,5aR,5bR,7aR,9S,11aR,11bR,13aR,13bR)-3a-amino-5a,5b,8,8,11a-pentamethyl-1-(prop-1-en-2-yl)icosahydro-1H-cyclopenta[a]chrysen-9-ol, HCl

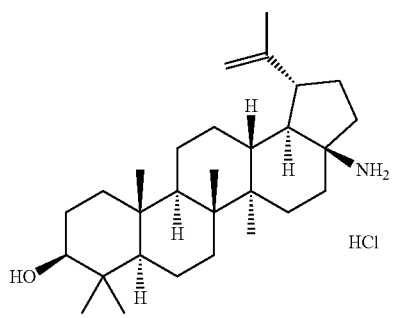

To a solution of (1R,3aS,5aR,5bR,7aR,9S,11aR,11bR,13aR,13bR)-3a-isocyanato-5a,5b,8,8,11a-pentamethyl-1-(prop-1-en-2-yl)icosahydro-1H-cyclopenta[a]chrysen-9-ol (7.76 g, 17.10 mmol) in 1,4-dioxane (100 mL) was added HCl (37%) (21.07 mL, 257 mmol). The mixture was heated to 60° C. for 15 h, then was cooled to rt and concentrated under reduced pressure. The residue was dissolved in dichloromethane and methanol and was concentrated two additional times to give (1R,3aS,5aR,5bR,7aR,9S,11aR,11bR,13aR,13bR)-3a-amino-5a,5b,8,8,11a-pentamethyl-1-(prop-1-en-2-yl)icosahydro-1H-cyclopenta[a]chrysen-9-ol, HCl (7.75 g, 16.7 mmol, 98% yield) as an off-white foam. The crude product was used in the next step with no purification.

Step 3. Preparation of tert-butyl ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)carbamate

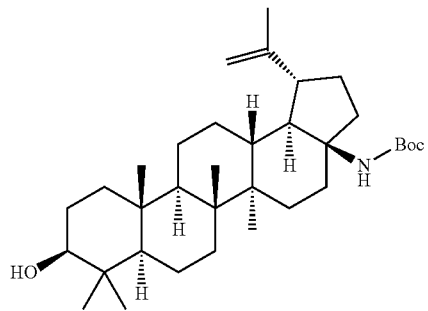

To a solution of (1R,3aS,5aR,5bR,7aR,9S,11aR,11bR,13aR,13bR)-3a-amino-5a,5b,8,8,11a-pentamethyl-1-(prop-1-en-2-yl)icosahydro-1H-cyclopenta[a]chrysen-9-ol, HCl (7.75 g, 16.7 mmol) in 1,4-dioxane (100 mL) was added water (25 mL), sodium bicarbonate (4.21 g, 50.2 mmol) and Boc anhydride (5.82 mL, 25.08 mmol). The mixture was stirred at rt for 16 h then the mixture was diluted with 100 mL of water and was extracted with ethyl acetate (3×100 mL). The combined organic layers were washed with brine, dried over magnesium sulfate, filtered and concentrated under reduced pressure to give tert-butyl ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)carbamate as an off-white foam. $^1$H NMR (500 MHz, chloroform-d) δ=4.74 (d, J=1.6 Hz, 1H), 4.64-4.62 (m, 1H), 4.34 (br. s., 1H), 3.24-3.18 (m, 1H), 2.63-2.35 (m, 3H), 2.06-1.93 (m, 1H), 1.71 (s, 3H), 1.46 (s, 9H), 1.04 (s, 3H), 0.99 (s, 3H), 0.98 (s, 3H), 0.86 (s, 3H), 0.79 (s, 3H), 1.77-0.68 (m, 22H).

Step 4. Preparation of tert-butyl ((1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate

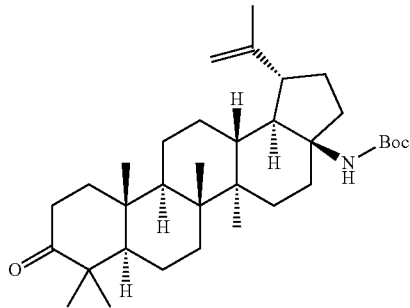

To a solution of the resulting tert-butyl ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)carbamate in dichloromethane (100 mL) was added pyridinium chlorochromate (4.69 g, 21.74 mmol). The mixture was stirred at rt for 5 h then an additional 1.0 g of PCC was added and the mixture was stirred at rt for 1 h. The mixture was filtered through a plug of silica gel and celite which was washed with a solution of 25% ethyl acetate in hexanes. The filtrate was concentrated under reduced pressure to give tert-butyl ((1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate as a light-yellow foam. $^1$H NMR (500 MHz, CHLOROFORM-d) δ=4.74 (d, J=1.7 Hz, 1H), 4.63 (t, J=1.7 Hz, 1H), 4.34 (br. s., 1H), 2.65-2.34 (m, 5H), 2.05-1.88 (m, 2H), 1.71 (s, 3H), 1.47 (s, 9H), 1.10 (s, 3H), 1.08 (s, 3H), 1.05 (s, 3H), 0.99 (s, 3H), 0.96 (s, 3H), 1.76-0.93 (m, 18H).

Step 5. Preparation of (1R,3aS,5aR,5bR,7aR,11aR,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate

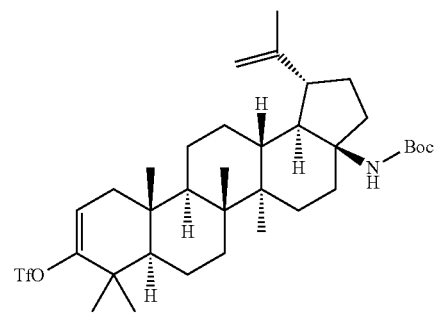

A solution of the resulting tert-butyl ((1R,3aS,5aR,5bR, 7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate in THF (100 mL) was cooled to −78° C. To the solution was added KHMDS (0.91M in THF) (40.4 mL, 36.8 mmol). The mixture was stirred for 20 minutes at −78° C. then a solution of 1,1,1-trifluoro-N-phenyl-N-(trifluoromethyl)sulfonyl methanesulfonamide (7.47 g, 20.90 mmol) in THF (100 mL) was added via canula. The mixture was stirred at −78° C. for 5 h, then was quenched with 100 mL of water and was extracted with ethyl acetate (3×75 mL). The combined organic layers were dried with magnesium sulfate. The drying agent was removed by filtration and the filtrate was concentrated under reduced pressure. The residue was taken up in a small amount of DCM and methanol and the yellow solids that formed were removed by filtration. The filtrate was again concentrated and treated with methanol and the solids that formed were again removed by filtration. The filtrate was concentrated and was adsorbed to silica gel and was then purified by flash chromatography using a 0-50% ethyl acetate in hexanes gradient and a Thomson 240 g silica gel column. The fractions containing the deprotected product were combined and were concentrated under reduced pressure to give a mixture of products. This mixture was repurified by flash chromatography using a 0-10% EtOAc in hexanes gradient and a 240 g Thomson silica gel column. The fractions containing the expected product were combined and concentrated under reduced pressure to give (1R,3aS,5aR, 5bR,7aR,11aR,11bR,13aR,13bR)-3a-((tert-butoxycarbonyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl trifluoromethanesulfonate (1.31 g, 1.99 mmol, 11.9% over 3 steps). ¹H NMR (500 MHz, CHLOROFORM-d) δ=5.57 (dd, J=6.7, 1.8 Hz, 1H), 4.73 (s, 1H), 4.62 (s, 1H), 4.32 (br. s., 1H), 2.64-2.31 (m, 3H), 2.16 (dd, J=17.0, 6.8 Hz, 1H), 2.04-1.94 (m, 1H), 1.70 (s, 3H), 1.45 (s, 9H), 1.13 (s, 3H), 1.06 (s, 3H), 1.03 (s, 3H), 0.97 (s, 3H), 0.93 (s, 3H), 1.82-0.86 (m, 18H).

Step 6. Preparation of (1R,3aS,5aR,5bR,7aR,11aR, 11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl trifluoromethanesulfonate

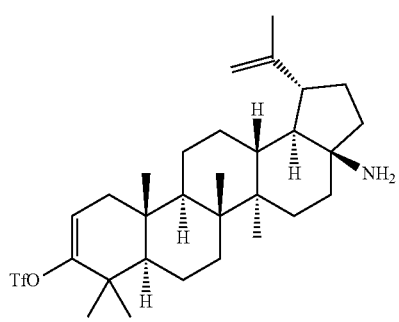

To a solution of (1R,3aS,5aR,5bR,7aR,11aR,11bR,13aR, 13bR)-3a-(((tert-butoxycarbonyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a]chrysen-9-yltrifluoromethanesulfonate (0.2 g, 0.304 mmol) in dichloromethane (2 mL) was added trifluoroacetic acid (0.5 mL, 6.49 mmol). The mixture was stirred at rt for 1.5 h then was concentrated under reduced pressure. The residue was diluted with saturated aqueous sodium bicarbonate (20 mL) and extracted with dichloromethane (3×20 mL). The combined organic layers were dried with sodium sulfate. The drying agent was removed by filtration. The filtrate was concentrated and adsorbed to silica gel and purified using a 12-100% ethyl acetate in hexanes gradient and a 12 g Thomson silica gel column. The fractions containing the expected product were combined and were concentrated under reduced pressure to give (1R,3aS,5aR,5bR,7aR,11aR,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.109 g, 0.195 mmol, 64.3% yield) as an off-white solid. ¹H NMR (500 MHz, chloroform-d) δ=5.57 (dd, J=6.8, 1.9 Hz, 1H), 4.73 (d, J=1.6 Hz, 1H), 4.63-4.60 (m, 1H), 2.54 (td, J=10.9, 5.3 Hz, 1H), 2.17 (dd, J=17.1, 6.9 Hz, 1H), 2.08-1.99 (m, 1H), 1.70 (s, 3H), 1.13 (s, 3H), 1.08 (s, 3H), 1.03 (s, 3H), 0.97 (s, 3H), 0.93 (s, 3H), 1.82-0.91 (m, 20H).

Method 2: Intermediate 1

Preparation of (1R,3aS,5aR,5bR,7aR,11aR,11bR, 13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl trifluoromethanesulfonate

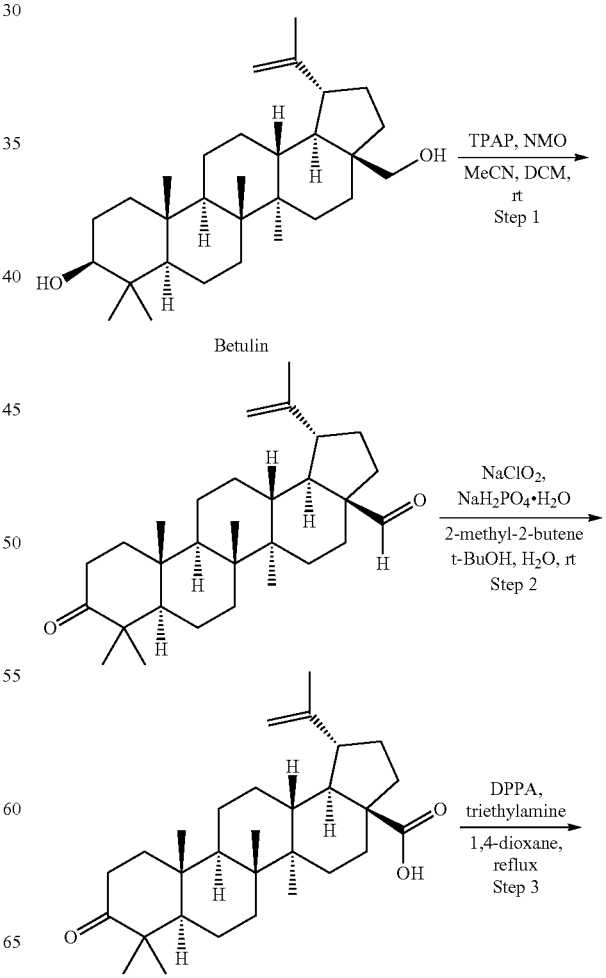

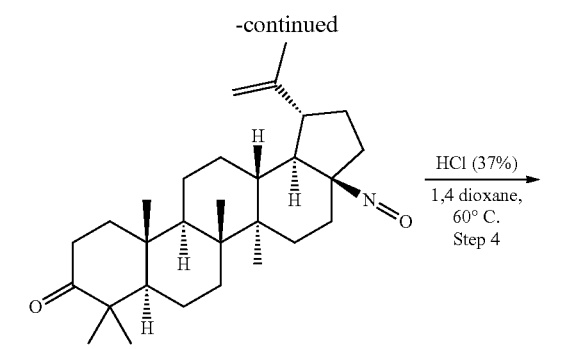

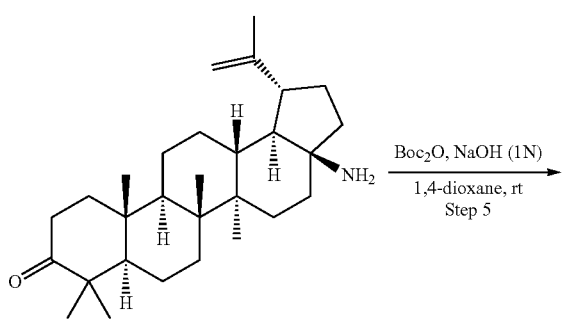

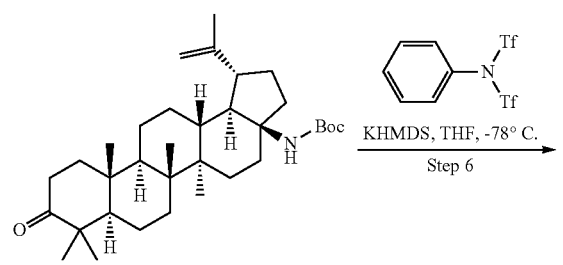

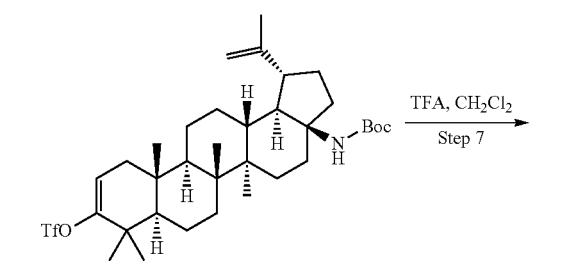

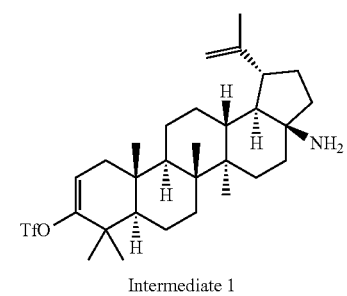

Intermediate 1

Step 1. Preparation of (1R,3aS,5aR,5bR,7aR,11aR, 11bR,13aR,13bR)-5a,5b,8,8,11a-pentamethyl-9-oxo-1-(prop-1-en-2-yl)icosahydro-1H-cyclopenta[a]chrysene-3a-carbaldehyde

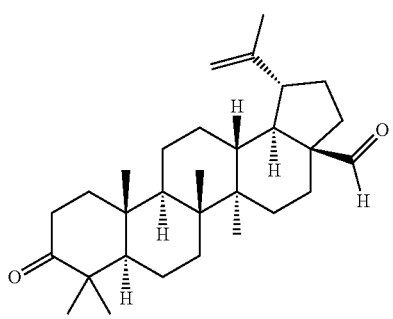

To suspension of (1R,3aS,5aR,5bR,7aR,9S,11aR,11bR, 13aR,13bR)-3a-(hydroxymethyl)-5a,5b,8,8,11a-pentamethyl-1-(prop-1-en-2-yl)icosahydro-1H-cyclopenta[a]chrysen-9-ol (20 g, 45.2 mmol) in acetonitrile (200 mL) and DCM (300 mL) was added 4 angstrom molecular sieves (5 g) and the mixture was stirred for 10 minutes at rt. To the mixture was then added NMO (15.88 g, 136 mmol) and TPAP (0.794 g, 2.259 mmol). The dark green mixture was stirred under nitrogen overnight. Additional NMO (2.0 g) and TPAP (0.08 g) were added and the mixture was stirred at rt for 7 h. The mixture was filtered through a pad of silica gel and celite which was washed with dichloromethane then 25% EtOAc in hexanes. The filtrate was concentrated under reduced pressure and purified using a Thomson 240 g silica gel column and a 15-20% ethyl acetate in hexanes gradient. The title product was isolated as a white foam (17.6 g, 40.1 mmol, 89%). $^1$H NMR (400 MHz, chloroform-d) δ=9.68 (d, J=1.5 Hz, 1H), 4.77 (d, J=2.0 Hz, 1H), 4.66-4.63 (m, 1H), 2.89 (td, J=11.2, 5.8 Hz, 1H), 2.56-2.36 (m, 2H), 2.16-2.03 (m, 2H), 1.97-1.84 (m, 2H), 1.71 (s, 3H), 1.08 (s, 3H), 1.03 (s, 3H), 1.00 (s, 3H), 0.97 (s, 3H), 0.94 (s, 3H), 1.83-0.87 (m, 18H).

Step 2. Preparation of (1R,3aS,5aR,5bR,7aR,11aR, 11bR,13aR,13bR)-5a,5b,8,8,11a-pentamethyl-9-oxo-1-(prop-1-en-2-yl)icosahydro-1H-cyclopenta[a]chrysene-3a-carboxylic acid

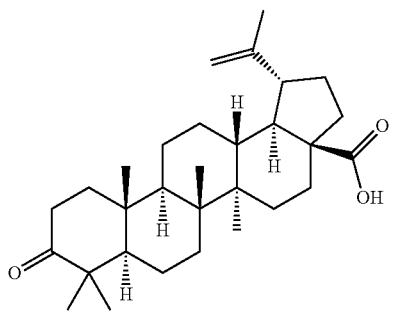

To a solution of (1R,3aS,5aR,5bR,7aR,11aR,11bR,13aR, 13bR)-5a,5b,8,8,11a-pentamethyl-9-oxo-1-(prop-1-en-2-yl) icosahydro-1H-cyclopenta[a]chrysene-3a-carbaldehyde (17.6 g, 36.1 mmol) in t-BuOH (100 mL) was added 2-methyl-2-butene (40 mL, 476 mmol). A solution of sodium chlorite (15 g, 133 mmol) and sodium phosphate monobasic monohydrate (25 g, 181 mmol) in water (200 mL) was added drop wise over 1.25 h and the mixture was stirred at rt for an additional 45 minutes. The mixture was diluted with saturated aqueous ammonium chloride (100 mL) and extracted with ethyl acetate (3×125 mL). The combined organic layers were washed with brine and dried over sodium sulfate. The drying agent was removed by filtration and the filtrate was concentrated under reduced pressure. The residue was purified by using a 300 g Thomson silica gel column and a 10-50% ethyl acetate in hexanes gradient. The fractions containing the expected product were combined and concentrated under reduced pressure to give (1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysene-3a-carboxylic acid as a white foam (16.4 g, 36.1 mmol, 100%). LCMS: m/e 453.2 (M−H)$^-$, 2.61 min (method 3). $^1$H NMR (400 MHz, chloroform-d) δ=10.02 (br. s., 1H), 4.75 (d, J=1.8 Hz, 1H), 4.64-4.61 (m, 1H), 3.02 (td, J=10.8, 4.8 Hz, 1H), 2.55-2.36 (m, 3H), 2.33-2.19 (m, 2H), 2.08-1.86 (m, 4H), 1.70 (s, 3H), 1.08 (s, 3H), 1.02 (s, 3H), 1.00 (s, 3H), 0.98 (s, 3H), 0.93 (s, 3H), 1.82-0.90 (m, 15H).

Step 3. Preparation of (1R,3aS,5aR,5bR,7aR,11aR,11bR,13aR,13bR)-3a-isocyanato-5a,5b,8,8,11a-pentamethyl-1-(prop-1-en-2-yl)octadecahydro-1H-cyclopenta[a]chrysen-9(5bH)-one

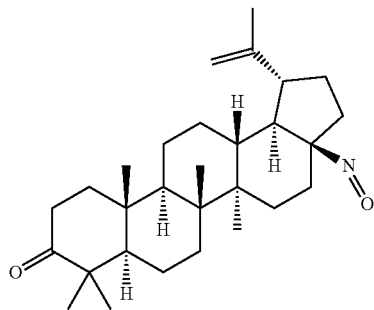

To a solution of (1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysene-3a-carboxylic acid (16.41 g, 36.1 mmol) in 1,4-dioxane (200 mL) was added triethylamine (15.09 mL, 108 mmol) and diphenyl phosphorazidate (11.67 mL, 54.2 mmol). The mixture was heated to reflux for 18.5 h, then was cooled to rt and concentrated under reduced pressure. The residue was split into two portions and was purified using a 0-15% ethyl acetate in hexanes gradient and a Thomson 240 g silica gel column to purify each portion. The fractions containing the expected product were combined and concentrated under reduced pressure to give (1R,3aS,5aR,5bR,7aR,11aR,11bR,13aR,13bR)-3a-isocyanato-5a,5b,8,8,11a-pentamethyl-1-(prop-1-en-2-yl)octadecahydro-1H-cyclopenta[a]chrysen-9(5bH)-one (10.3 g, 22.80 mmol, 63.2% yield) as an off-white foam. $^1$H NMR (400 MHz, chloroform-d) δ=4.75 (d, J=2.0 Hz, 1H), 4.66-4.63 (m, 1H), 2.60-2.36 (m, 4H), 2.17-2.04 (m, 1H), 1.69 (s, 3H), 1.10 (s, 3H), 1.08 (s, 3H), 1.04 (s, 3H), 0.95 (s, 6H), 2.01-0.71 (m, 20H).

Step 4. Preparation of (1R,3aS,5aR,5bR,7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one, HCl

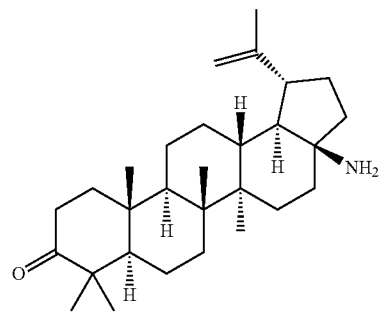

To a solution of (1R,3aS,5aR,5bR,7aR,11aR,11bR,13aR,13bR)-3a-isocyanato-5a,5b,8,8,11a-pentamethyl-1-(prop-1-en-2-yl)octadecahydro-1H-cyclopenta[a]chrysen-9(5bH)-one (10.3 g, 22.80 mmol) in 1,4-dioxane (100 mL) was added HCl (37%) (28.1 mL, 342 mmol). The mixture was heated to 60° C. for 15.5 h then was cooled to rt and was concentrated under reduced pressure. The residue was diluted with saturated aqueous sodium bicarbonate (150 mL) and was extracted with dichloromethane (3×100 mL). The combined organic layers were dried with sodium sulfate, filtered and concentrated under reduced pressure. The residue was purified by flash chromatography using a 20-60% ethyl acetate in hexanes gradient with 0.1% triethyl amine added to the mixture. The fractions containing the expected product were combined and concentrated under reduced pressure to give (1R,3aS,5aR,5bR,7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one, HCl (5.4 g, 11.68 mmol, 51.2% yield) as a yellow foam. LCMS: m/e 426.5 (M+H)$^+$, 1.59 min (method 1). $^1$H NMR (400 MHz, CHLOROFORM-d) δ=4.73 (d, J=2.3 Hz, 1H), 4.60 (dd, J=2.4, 1.4 Hz, 1H), 2.58-2.37 (m, 3H), 2.11-1.98 (m, 1H), 1.94-1.87 (m, 1H), 1.69 (d, J=0.5 Hz, 3H), 1.09 (s, 3H), 1.08 (s, 3H), 1.03 (s, 3H), 0.97 (s, 3H), 0.94 (s, 3H), 1.79-0.91 (m, 20H).

Step 5. Preparation of tert-butyl ((1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate

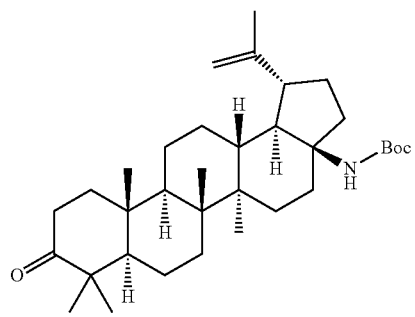

To a solution of (1R,3aS,5aR,5bR,7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one (5.25 g, 12.33 mmol) in 1,4-dioxane (50 mL) was added sodium hydroxide (1N) (24.67 mL, 24.67 mmol) followed by di-tert-butyl dicarbonate (3.15 mL, 13.57 mmol). The mixture was stirred at rt for 2 h then 30 mL of methanol, 50 mL of dichloromethane and 20 ml, of water were added to help solubilize the mixture. After stirring for 1.5 h at rt, the reaction was not complete, so di-tert-butyl dicarbonate (0.3 g) was added and the mixture stirred at rt for 3 h. Again di-tert-butyl dicarbonate (0.3 g) was added and the mixture was stirred at rt for 16 h. Since traces of starting material were still present, di-tert-butyl dicarbonate (1 g) was added to the mixture and the stirring was continued for 6 h at which point TLC showed no starting material remaining. The mixture was diluted with water (75 mL) and extracted with dichloromethane (3×100 mL). The combined organic layers were washed with water (100 mL) then were dried with sodium sulfate, filtered and concentrated under reduced pressure. The residue was purified using a 0-10% ethyl acetate in hexanes gradient and a 240 g silica gel column. The fractions containing the expected product were combined and concentrated under reduced pressure to give tert-butyl ((1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate (5.85 g, 11.13 mmol, 90% yield) as a white foam. $^1$H NMR (400 MHz, chloroform-d) δ=4.72 (s, 1H), 4.62 (s, 1H), 4.33 (br. s., 1H), 2.64-2.32 (m, 5H), 2.06-1.84 (m, 2H), 1.69 (s, 3H), 1.45 (s, 9H), 1.08 (s, 3H), 1.06 (s, 3H), 1.03 (s, 3H), 0.97 (s, 3H), 0.94 (s, 3H), 1.74-0.86 (m, 18H).

Step 6. Preparation of (1R,3aS,5aR,5bR,7aR,11aR,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate

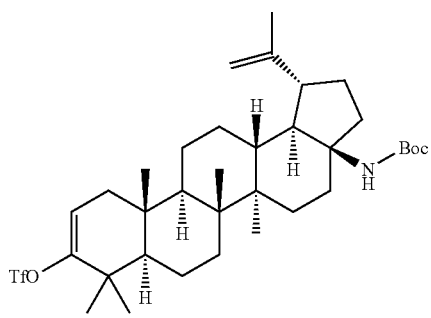

A flask containing a solution of tert-butyl ((1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate (1.2 g, 2.282 mmol) and 1,1,1-trifluoro-N-phenyl-N-(trifluoromethyl)sulfonyl methanesulfonamide (1.019 g, 2.85 mmol) in THF (20 mL) was cooled to −78° C. To the solution was added KHMDS (0.91 M in THF) (5.52 mL, 5.02 mmol). The mixture was stirred at −78° C. for 1 h then warmed to rt and stirred for 1 h. The reaction was then quenched with saturated aqueous ammonium chloride (30 mL) and extracted with ethyl acetate (3×30 mL). The combined organic layers were dried over magnesium sulfate. The drying agent was removed by filtration and the filtrate was concentrated under reduced pressure. The crude material was purified using a 0-12% ethyl acetate in hexanes gradient and a Thomson 80 g silica gel column. The fractions containing the expected product were combined and concentrated under reduced pressure to give (1R,3aS,5aR,5bR,7aR,11aR,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (0.9 g, 1.368 mmol, 59.9% yield) as a white foam. $^1$H NMR (500 MHz, chloroform-d) δ=5.57 (dd, J=6.7, 1.8 Hz, 1H), 4.73 (s, 1H), 4.62 (s, 1H), 4.32 (br. s., 1H), 2.64-2.31 (m, 3H), 2.16 (dd, J=17.0, 6.8 Hz, 1H), 2.04-1.94 (m, 1H), 1.70 (s, 3H), 1.45 (s, 9H), 1.13 (s, 3H), 1.06 (s, 3H), 1.03 (s, 3H), 0.97 (s, 3H), 0.93 (s, 3H), 1.82-0.86 (m, 18H).

Step 7

Same experimental procedure described for Step 6 in method 1 above.

Alternatively, the intermediate (1R,3aS,5aR,5bR,7aR,11aR,11bR,13aR,13bR)-3a-isocyanato-5a,5b,8,8,11a-pentamethyl-1-(prop-1-en-2-yl)octadecahydro-1H-cyclopenta[a]chrysen-9(5bH)-one can be prepared from betulinic acid following the scheme shown below:

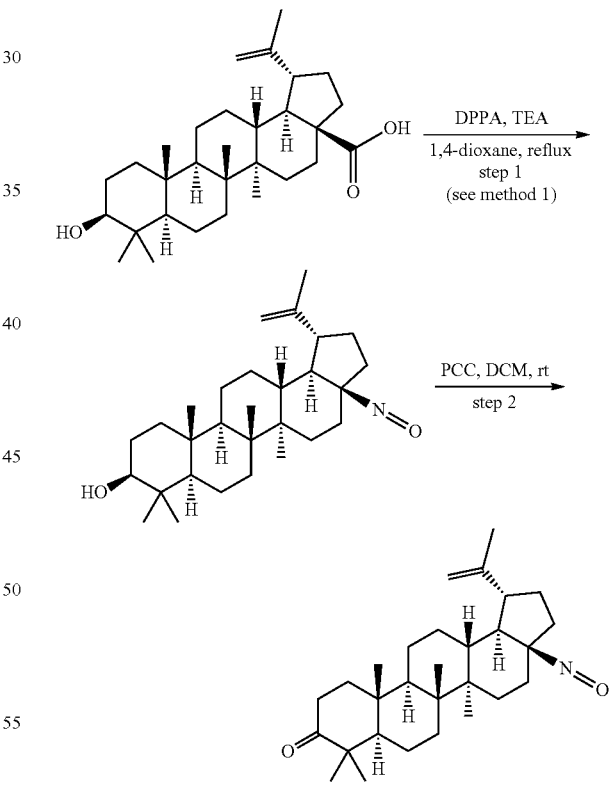

Step 1: Preparation of (1R,3aS,5aR,5bR,7aR,9S,11aR,11bR,13aR,13bR)-3a-isocyanato-5a,5b,8,8,11a-pentamethyl-1-(prop-1-en-2-yl)icosahydro-1H-cyclopenta[a]chrysen-9-ol The title compound was prepared using the same conditions described above in Step 1, method 1 using betulinic acid as starting material.

Step 2

To a solution of 24 g of crude (1R,3aS,5aR,5bR,7aR,9S,11aR,11bR,13aR,13bR)-3a-isocyanato-5a,5b,8,8,11a-pentamethyl-1-(prop-1-en-2-yl)icosahydro-1H-cyclopenta[a]chrysen-9-ol in dichloromethane (200 mL) was added PCC (11.80 g, 54.8 mmol) in three portions over 45 minutes. The mixture was stirred at rt for 4 h, then an additional 1 g of PCC was added and the mixture was further stirred at rt for 2 h. The mixture was filtered through a plug of silica gel and celite and the plug was washed with a 1:1 solution of ethyl acetate:hexanes. The filtrate was concentrated under reduced pressure to give the crude product which was used in the next step with no additional purification. $^1$H NMR (500 MHz, Chloroform-d) δ=4.76-4.74 (m, 1H), 4.65-4.63 (m, 1H), 2.62-2.36 (m, 3H), 2.16-2.03 (m, 1H), 1.69 (s, 3H), 1.10 (s, 3H), 1.08 (s, 3H), 1.04 (s, 3H), 0.96 (s, 6H), 1.95-0.91 (m, 21H).

Key Intermediate Triflate 1

Preparation of (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate

Step 1: Preparation of (1R,3aS,5aR,5bR,7aR,11aR,11bR,13aR,13bR)-3a-(aziridin-1-yl)-5a,5b,8,8,11a-pentamethyl-1-(prop-1-en-2-yl)octadecahydro-1H-cyclopenta[a]chrysen-9(5bH)-one In a pressure vessel, a suspension of (1R,3aS,5aR,5bR,7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one (4.0 g, 9.4 mmol) and K$_3$PO$_4$ (9.97 g, 47.0 mmol) in 1,2-dichloroethane (300 mL) and acetonitrile (30 mL) was flushed with nitrogen, sealed, and stirred at 130° C. overnight. The reaction mixture was cooled to RT, filtered through a bed of silica gel, and rinsed with EtOAc. The filtrate was concentrated in vacuo to give crude aziridine (4.0 g, 94%) as a solid which was used for the next step without purification. MS: m/e 452.5 (M+H)$^+$, 2.63 min (method 4).

Step 2: Preparation of (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)octadecahydro-1H-cyclopenta[a]chrysen-9(5bH)-one To a solution of (1R,3aS,5aR,5bR,7aR,11aR,11bR,13aR,13bR)-3a-(aziridin-1-yl)-5a,5b,8,8,11a-pentamethyl-1-(prop-1-en-2-yl)octadecahydro-1H-cyclopenta[a]chrysen-9(5bH)-one (4.0 g, 8.85 mmol) and thiomorpholine 1,1-

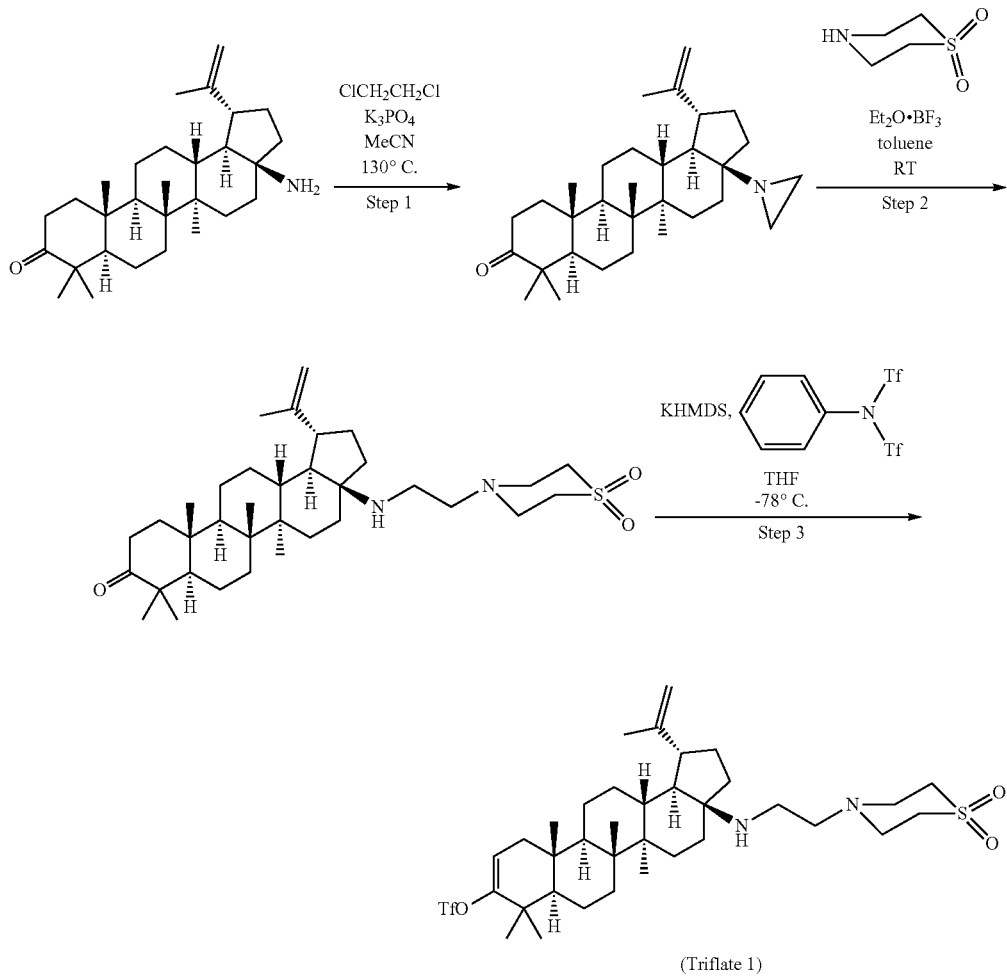

(Triflate 1)

dioxide (4.79 g, 35.4 mmol) in toluene (30 mL) was added boron trifluoride diethyl etherate (1 mL in 100 mL of toluene, mL) forming a yellow suspension. The mixture was sonicated for 2 min, then stirred at RT for 5 days. The reaction mixture was diluted with EtOAc (200 mL), washed with NaHCO$_3$ (200 mL), dried over Na$_2$SO$_4$, filtered and concentrated in vacuo. The crude product was purified by a silica gel column (160 gm) eluted with 20-50% of EtOAc/Hexane to give desired ketone (2.95 g, 57%) as a solid. MS: m/e 587.5 (M+H)$^+$, 2.39 min (method 4). $^1$H NMR (400 MHz, CHLOROFORM-d) δ 4.74-4.70 (m, 1H), 4.62-4.59 (m, 1H), 3.11-2.99 (m, 7H), 2.72-2.36 (m, H), 1.98-0.82 (m. 23H), 1.69 (s, 3H), 1.08 (s, 6H), 1.04 (s, 3H), 0.98 (s, 3H), 0.95 (s, 3H).

Step 3

To a solution of (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)octadecahydro-1H-cyclopenta[a]chrysen-9(5bH)-one (2.95 g, 5.03 mmol) in THF (50 mL) at −78° C. was added KHMDS (1 M in THF, 7.54 mL, 7.54 mmol). The yellow solution was stirred at −78° C. for 30 min. A solution of 1,1,1-trifluoro-N-phenyl-N-((trifluoromethyl)sulfonyl)methanesulfonamide (1.89 g, 5.28 mmol) in THF (10 mL) was added. The resulted reddish reaction mixture was stirred at −78° C. for 2 h, then warmed to RT and stirred at RT overnight (20 h). The reaction was quenched with saturated aq NH$_4$Cl (50 mL). The separated aqueous layer was extracted with EtOAc (2×100 mL). The combined organic layers were washed with brine (50 mL), dried over Na$_2$SO$_4$, filtered and concentrated in vacuo. The crude product was purified by a silica gel column (160 gm) eluted with 20-80% of EtOAc/Hexane to give (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (triflate 1) (2.78 g, 77%) as a solid. MS: m/e 719.5 (M+H)$^+$, 2.60 min (method 4). $^1$H NMR (400 MHz, CHLOROFORM-d) δ 5.57 (dd, J=6.8, 2.0 Hz, 1H), 4.76-4.71 (m, 1H), 4.64-4.61 (m, 1H), 3.13-3.02 (m, 7H), 2.85-2.75 (m, 1H), 2.73-2.64 (m, 2H), 2.62-2.52 (m, 2H), 2.17 (dd, J=17.1, 6.8 Hz, 1H), 2.00-0.86 (m, 22H), 1.70 (s, 3H), 1.13 (s, 3H), 1.08 (s, 3H), 1.03 (s, 3H), 0.98 (s, 3H), 0.93 (s, 3H). $^{19}$F NMR (376 MHz, CHLOROFORM-d) δ −74.84 (s, 3F).

Key Intermediate: Triflate 2

Preparation of (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate

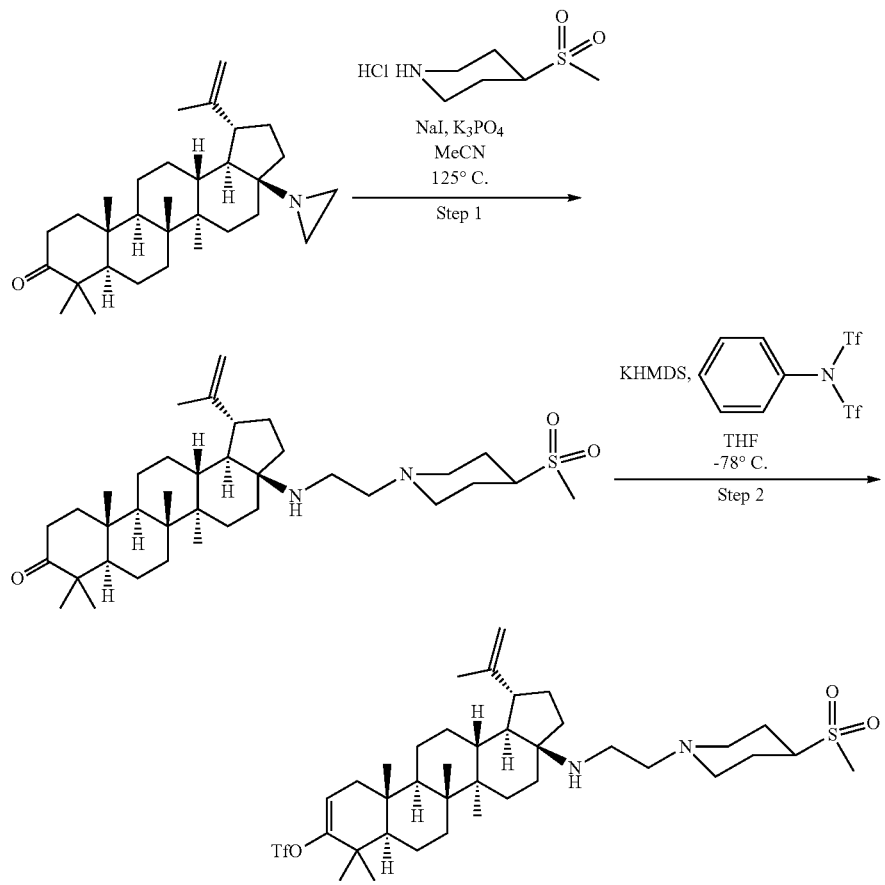

(Triflate 2)

Step 1: Preparation of (1R,3aS,5aR,5bR,7aR,11aR, 11bR,13aR,13bR)-5a,5b,8,8,11a-pentamethyl-3a-((2-(4-(methylsulfonyl)piperidin-1-yl)ethyl)amino)-1-(prop-1-en-2-yl)octadecahydro-1H-cyclopenta[a]chrysen-9(5bH)-one In a pressure vessel, a suspension of (1R,3aS,5aR,5bR, 7aR,11aR,11bR,13aR,13bR)-3a-(aziridin-1-yl)-5a,5b,8,8, 11a-pentamethyl-1-(prop-1-en-2-yl)octadecahydro-1H-cyclopenta[a]chrysen-9(5bH)-one (5.0 g, 11.07 mmol), 4-(methylsulfonyl)piperidine hydrochloride (4.42 g, 22.14 mmol), NaI (1.659 g, 11.07 mmol) and $K_3PO_4$ (4.70 g, 22.14 mmol) in toluene (50 mL) and $CH_3CN$ (50 mL) was flushed with nitrogen, sealed, and stirred at 125° C. for 24 h. The reaction mixture was concentrated in vacuo, and the residue was partitioned between EtOAc (100 mL) and $H_2O$ (100 mL). The separated aqueous layer was extracted with EtOAc (2×100 mL). The combined organic layers were washed with brine (100 mL), dried over $Na_2SO_4$, filtered and concentrated in vacuo. The crude product was purified by a silica gel column (240 gm) eluted with 40-80% EtOAc/Hexane to give desired ketone (4.26 g, 63%) as a solid. MS: m/e 615.6 $(M+H)^+$, 2.40 min (method 4). $^1H$ NMR (400 MHz, CHLOROFORM-d) δ 4.67 (d, J=2.3 Hz, 1H), 4.54 (dd, J=2.3, 1.5 Hz, 1H), 3.07 (dd, J=16.7, 11.7 Hz, 2H), 2.88-2.78 (m, 1H), 2.81 (s, 3H), 2.61-2.30 (m, 7H), 2.14-2.02 (m, 3H), 1.98-1.70 (m, 9H), 1.69-0.94 (m, 16H), 1.65 (s, 3H), 1.06 (s, 3H), 1.03 (s, 3H), 0.99 (s, 3H), 0.93 (s, 3H), 0.90 (s, 3H).

Step 2

To a solution of (1R,3aS,5aR,5bR,7aR,11aR,11bR,13aR, 13bR)-5a,5b,8,8,11a-pentamethyl-3a- ((2-(4-(methylsulfonyl)piperidin-1-yl)ethyl)amino)-1-(prop-1-en-2-yl)octadecahydro-1H-cyclopenta[a]chrysen-9(5bH)-one (4.26 g, 6.93 mmol) in THF (80 mL) at −78° C. was added KHMDS (1 M in THF) (10.39 mL, 10.39 mmol). The resulted orange slurry was stirred at −78° C. for 20 min. A solution of 1,1,1-trifluoro-N-phenyl-N-((trifluoromethyl)sulfonyl)methanesulfonamide (2.72 g, 7.62 mmol) in THF (20 mL) was added. The resulted orange reaction mixture was stirred at −78° C. for 2 h. The reaction was quenched with saturated aq $NH_4Cl$ (100 mL). The separated aqueous layer was extracted with EtOAc (3×100 mL). The combined organic layers were washed with brine (100 mL), dried over $Na_2SO_4$, filtered and concentrated in vacuo. The crude product was purified by a silica gel column (240 gm), eluted with 40-100% EtOAc/Hexane to give (1R,3aS,5aR,5bR,7aR,11aR,11bR,13aR, 13bR)-5a,5b,8,8,11a-pentamethyl-3a-((2-(4-(methylsulfonyl)piperidin-1-yl)ethyl)amino)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yltrifluoromethanesulfonate, (triflate 2) (3.5 g, 68%) as a solid. MS: m/e 747.4 $(M+H)^+$, 2.82 min (method 4). $^1H$ NMR (400 MHz, CHLOROFORM-d) δ 5.56 (dd, J=6.7, 1.9 Hz, 1H), 4.73 (d, J=2.0 Hz, 1H), 4.60 (dd, J=2.1, 1.4 Hz, 1H), 3.17-3.07 (m, 2H), 2.88-2.79 (m, 1H), 2.85 (s, 3H), 2.69-2.54 (m, 3H), 2.52-2.42 (m, 2H), 2.19-2.07 (m, 4H), 2.03-0.88 (m, 24H), 1.69 (s, 3H), 1.12 (s, 3H), 1.08 (s, 3H), 1.02 (s, 3H), 0.96 (s, 3H), 0.91 (s, 3H). $^{19}F$ NMR (376 MHz, CHLOROFORM-d) δ −74.85 (s, 3F).

General Scheme #1 for the Preparation of Examples 1-6

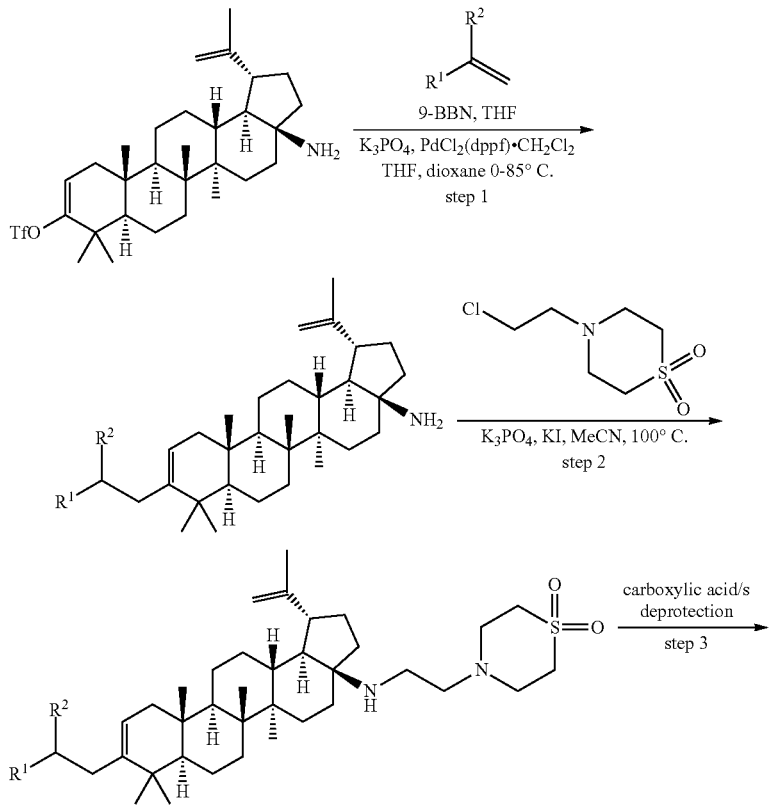

Example 1

Preparation of 4-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)cyclohexanecarboxylic acid, TFA

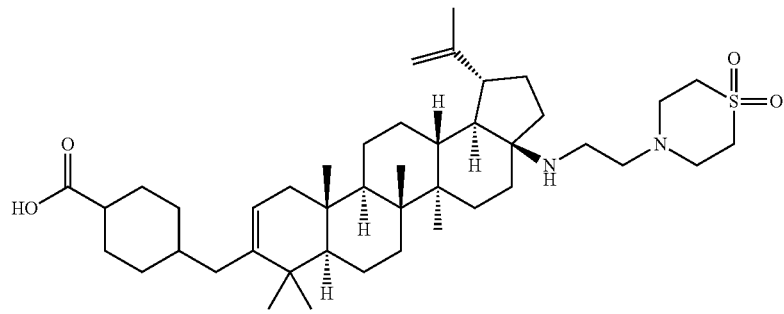

Step 1. Preparation of ethyl 4-(((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)cyclohexanecarboxylate

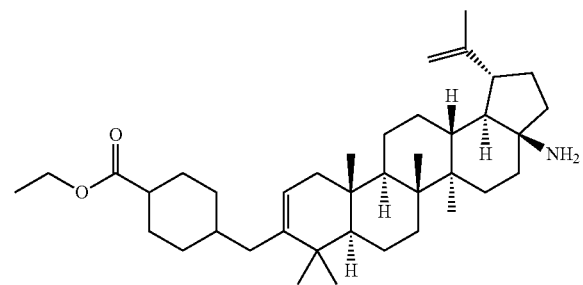

A solution of ethyl 4-methylenecyclohexanecarboxylate (0.045 g, 0.269 mmol) (prepared as described in *Bioorg. Med. Chem.* 2004, 12, 5719-5725) in THF (1.5 mL) was cooled to 0° C. and 9-BBN (0.5 M in THF) (0.574 mL, 0.287 mmol) was added dropwise. The mixture was removed from the ice bath and was stirred at rt for 2 h. To the solution was added a solution of phosphoric acid, potassium salt (1M) (0.448 mL, 0.448 mmol) followed by a solution of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.1 g, 0.179 mmol) in 1,4-dioxane (1.5 mL) and finally 1,1'-bis(diphenylphosphino)ferrocenepalladium(II) dichloride, toluene (7.38 mg, 8.96 μmol). The mixture was heated to 85° C. for 18.5 h and then it was cooled to rt, diluted with water (7 mL), and extracted with ethyl acetate (3×10 mL). The organic layers were dried over magnesium sulfate, filtered, and concentrated under reduced pressure. The residue was purified by flash chromatography using a 10-60% ethyl acetate in hexanes gradient and a 24 g silica gel column to give the title compound (78.5 mg, 76% yield) as a white solid. LCMS: m/e 578.3 (M+H)$^+$, 2.74 min (method 2).

Step 2. Preparation of ethyl 4-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)cyclohexanecarboxylate

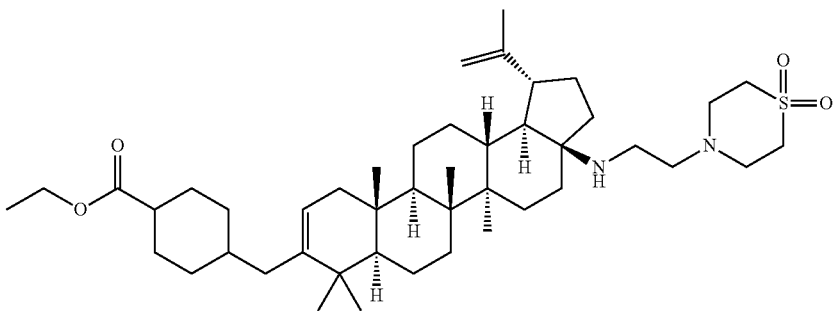

To a sealable flask containing ethyl 4-(((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)methyl)cyclohexanecarboxylate (0.078 g, 0.135 mmol) was added phosphoric acid, potassium salt (0.143 g, 0.675 mmol), potassium iodide (0.067 g, 0.405 mmol), and 4-(2-chloroethyl)thiomorpholine 1,1-dioxide, HCl (0.095 g, 0.405 mmol) (prepared as described in WO2002045652). The mixture was diluted with acetonitrile (1.25 mL), flushed with nitrogen, sealed, and heated to 100° C. for 18.5 h. The mixture was diluted with water (10 mL) and was extracted with ethyl acetate (3×10 mL). The organic layers were washed with brine, dried over magnesium sulfate, filtered, and concentrated under reduced pressure. The residue was purified by flash chromatography using a 5-55% ethyl acetate in hexanes gradient and a 12 g silica gel column to give the title compound (77 mg, 77% yield) as a clear film. LCMS: m/e 739.5 (M+H)+, 2.17 min (method 1).

Step 3

To a solution of ethyl 4-(((1R,3aS,5aR,5bR,7aR,11aS, 11bR,13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl) cyclohexanecarboxylate (0.077 g, 0.104 mmol) in 1,4-dioxane (2 mL) was added NaOH (1N) (0.521 mL, 0.521 mmol). The mixture was heated to 75° C. After 3 h of heating, the mixture was cooled to rt, diluted with methanol and dioxane, and purified by prep HPLC (method 1, retention time: 10.3 minutes) to give 4-(((1R,3aS,5aR,5bR,7aR,11aS,11bR, 13aR,13bR)-3a-((2-(1,1-dioxidothiomorpholino)ethyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)methyl) cyclohexanecarboxylic acid, TFA (0.026 g, 30% yield) as a white solid. LCMS: m/e 711.6 (M+H)+, 1.89 min (method 1). 1H NMR (400 MHz, acetic acid d4) δ=5.28 (d, J=5.0 Hz, 1H), 4.80 (s, 1H), 4.70 (s, 1H), 3.46 (d, J=12.5 Hz, 1H), 3.31-3.01 (m, 11H), 2.91-2.82 (m, 1H), 1.72 (s, 3H), 1.22 (s, 3H), 1.08 (s, 3H), 0.97 (s, 3H), 0.91 (s, 6H), 2.35-0.85 (m, 34H).

Example 2 and Example 3

Preparation of 3-(((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)methyl)cyclohexanecarboxylic acid, TFA

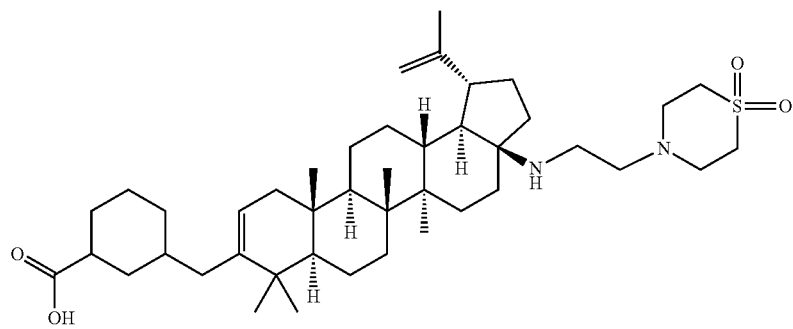

Isomer 1 and Isomer 2

Step 1. Preparation of ethyl 3-(((1R,3aS,5aR,5bR, 7aR,11aS,11bR,13aR,13bR)-3α-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) methyl)cyclohexanecarboxylate

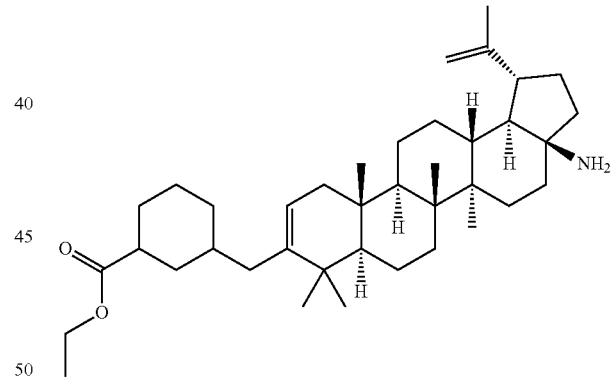

A solution of ethyl 3-methylenecyclohexanecarboxylate (0.045 g, 0.269 mmol) (prepared as described in J. Org. Chem. 1995, 60, 3518-3522) in THF (1.5 mL) was cooled to 0° C. and 9-BBN (0.5 M in THF) (0.574 mL, 0.287 mmol) was added dropwise. The mixture was removed from the ice bath and was stirred at rt for 2 h. To the solution was added a solution of phosphoric acid, potassium salt (1M) (0.448 mL, 0.448 mmol) followed by a solution of (1R,3aS,5aR,5bR, 7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yltrifluoromethanesulfonate (0.1 g, 0.179 mmol) in 1,4-dioxane (1.5 mL) and finally 1,1'-bis(diphenylphosphino)ferrocenepalladium(II) dichloride, Toluene (7.38 mg, 8.96 μmol). The mixture was heated to 85° C. for 19 h, cooled to rt, diluted with water (15 mL), and extracted with ethyl acetate (3×15 mL). The organic layers were washed with brine, dried over magnesium sulfate, filtered, and concentrated under reduced pressure. The residue was purified by flash chromatography using a 5-50% EtOAc in hexanes gradient and a 12 g silica gel column. The fractions containing the product were combined and concentrated under reduced pressure to give the title compound (0.089 g, 86% yield) as an off-white foam. $^1$H NMR (400 MHz, CHLOROFORM-d) δ=5.23 (d, J=5.5 Hz, 1H), 4.73 (d, J=2.3 Hz, 1H), 4.61 (dd, J=2.1, 1.4 Hz, 1H), 4.16-4.08 (m, 2H), 2.55 (td, J=10.9, 5.3 Hz, 1H), 1.70 (s, 3H), 1.08 (s, 3H), 0.97 (s, 3H), 0.95 (s, 3H), 0.86 (s, 3H), 0.84 (s, 3H), 2.37-0.73 (m, 39H).

Step 2. Preparation of ethyl 3-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)cyclohexanecarboxylate

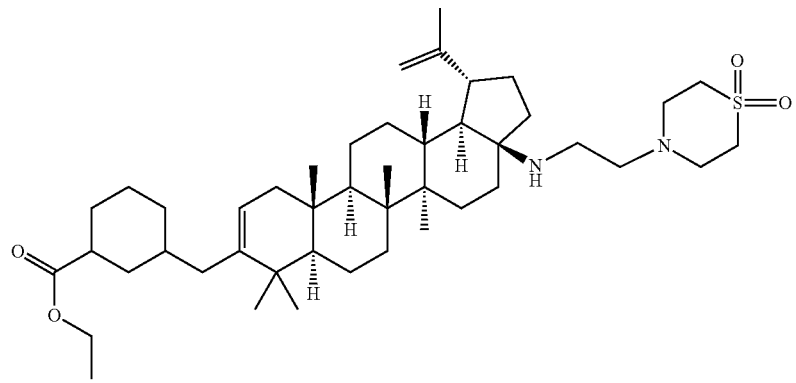

To a sealable flask containing ethyl 3-(((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)cyclohexanecarboxylate (0.078 g, 0.135 mmol) was added phosphoric acid, potassium salt (0.143 g, 0.675 mmol), potassium iodide (0.067 g, 0.405 mmol), and 4-(2-chloroethyl)thiomorpholine 1,1-dioxide, HCl (0.095 g, 0.405 mmol). The mixture was diluted with acetonitrile (1.25 mL), flushed with nitrogen, sealed, and heated to 100° C. After heating the mixture for 16 h, it was cooled to rt, diluted with water (5 mL), and extracted with dichloromethane (3×5 mL). The combined organic layers were dried with sodium sulfate, filtered, and concentrated under reduced pressure. The residue was purified by flash chromatography using a 0-50% EtOAc in hexanes gradient and a 12 g silica gel column. The fractions containing the product were combined and concentrated under reduced pressure to give the title compound (0.078 g, 0.106 mmol, 78% yield) as a white foam. LCMS: m/e 739.8 (M+H)$^+$, 2.25 min (method 1).

Step 3

To a solution of ethyl 3-(((1R,3aS,5aR,5bR,7aR,11aS,11bR,13aR,13bR)-3a- ((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)cyclohexanecarboxylate (0.078 g, 0.106 mmol) in 1,4-dioxane (3 mL) was added NaOH (1N) (0.528 mL, 0.528 mmol). The mixture was heated to 75° C. for 8 h, cooled to rt and purified by prep HPLC (method 2) to afford 2 isomers: isomer 1 retention time=11.4 minutes and isomer 2=12.5 minutes. Isomer 2 was repurified by prep HPLC (method 3, retention time=16.9 minutes). (Isomer 1, white solid, 16.4 mg, 19% yield; isomer 2, white solid, 17.6 mg, 20% yield).

Example 2 ethyl 3-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)cyclohexanecarboxylate (Isomer 1): LCMS: m/e: 711.6 (M+H)$^+$, 1.87 min (method 1). $^1$H NMR (500 MHz, acetic acid d$_4$) δ=5.31 (d, J=5.7 Hz, 1H), 4.81 (s, 1H), 4.71 (s, 1H), 3.48 (d, J=12.1 Hz, 1H), 3.34-3.01 (m, 11H), 2.91-2.83 (m, 1H), 2.41-2.32 (m, 1H), 1.73 (s, 3H), 1.23 (s, 3H), 1.09 (s, 3H), 0.99 (s, 3H), 0.93 (s, 6H), 2.30-0.77 (m, 33H).

Example 3 ethyl 3-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)cyclohexanecarboxylate (Isomer 2): LCMS: m/e: 711.6 (M+H)$^+$, 1.96 min (method 1). $^1$H NMR was very similar to isomer 1, only isomer 2 showed a splitting of the multiplet at 2.32-2.41 ppm into two peaks at 2.31-2.40 and 2.70-2.76 ppm respectively (~0.7:0.3 ratio).

Example 4

Preparation of 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)pentanoic acid, TFA

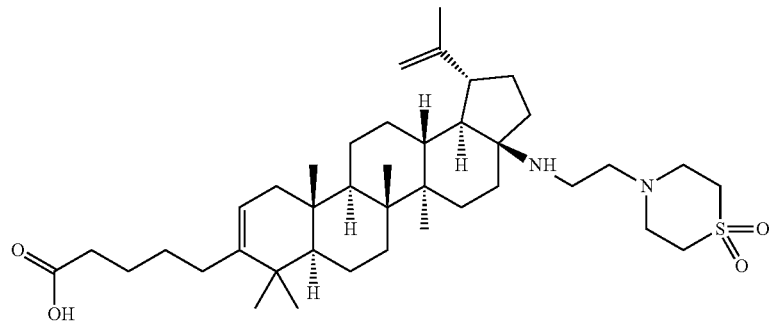

Step 1. Preparation of methyl 5-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)pentanoate

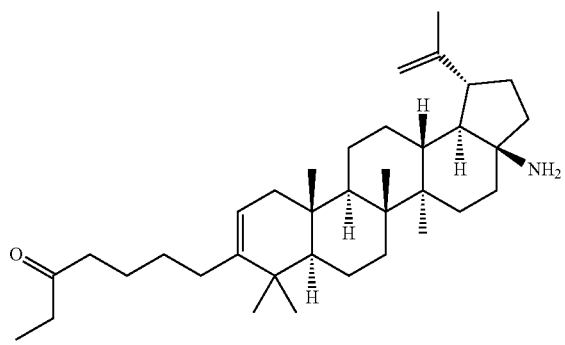

A solution of methyl 4-pentenoate (0.031 g, 0.269 mmol) in THF (1.5 mL) was cooled to 0° C. and 9-BBN (0.5M in THF) (0.574 mL, 0.287 mmol) was added dropwise. The mixture was removed from the ice bath and was stirred at rt for 2 h. To the solution was added a solution of phosphoric acid, potassium salt (1M) (0.448 mL, 0.448 mmol) followed by a solution of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (0.1 g, 0.179 mmol) in 1,4-dioxane (1.5 mL) and finally 1,1'-bis(diphenylphosphino)ferrocenepalladium(II) dichloride, Toluene (7.38 mg, 8.96 μmol). The mixture was heated to 85° C. for 16 h, cooled to rt, diluted with water (15 mL), and extracted with ethyl acetate (3×15 mL). The organic layers were combined, washed with brine, dried over magnesium sulfate, filtered, and concentrated under reduced pressure. The residue was purified by flash chromatography using a 5-50% EtOAc in hexanes gradient and a 12 g silica gel column to give the title compound (0.072 g, 77% yield) as an off-white foam. LCMS: m/e: 524.5 (M+H)$^+$, 2.04 min (method 1). $^1$H NMR (400 MHz, chloroform-d) δ=5.23 (d, J=5.3 Hz, 1H), 4.73 (d, J=2.0 Hz, 1H), 4.62-4.59 (m, 1H), 3.67 (s, 3H), 2.55 (td, J=10.9, 5.3 Hz, 1H), 2.33 (t, J=7.5 Hz, 2H), 2.09-1.92 (m, 4H), 1.70 (s, 3H), 1.07 (s, 3H), 0.97 (s, 6H), 0.89 (s, 3H), 0.83 (s, 3H), 1.78-0.80 (m, 26H).

Step 2. Preparation of methyl 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)pentanoate

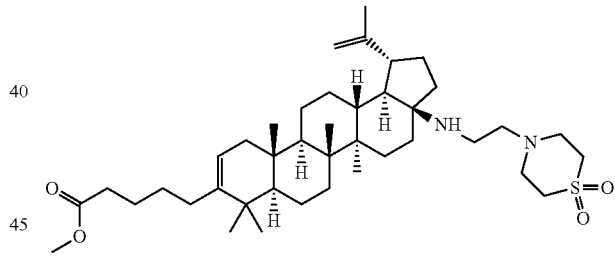

To a sealable flask containing methyl 5-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)pentanoate (0.07 g, 0.134 mmol) was added phosphoric acid, potassium salt (0.142 g, 0.668 mmol), potassium iodide (0.067 g, 0.401 mmol) and 4-(2-chloroethyl)thiomorpholine 1,1-dioxide, HCl (0.094 g, 0.401 mmol). The mixture was diluted with acetonitrile (1.25 mL), flushed with nitrogen, sealed, and heated to 100° C. After heating the mixture for 24 h, the mixture was cooled to rt, diluted with water (7 mL), and extracted with dichloromethane (3×7 mL). The combined organic layers were dried with sodium sulfate, filtered, and concentrated under reduced pressure. The residue was purified by flash chromatography using a 0-50% EtOAc in hexanes gradient and a 12 g silica gel column to give the title compound (0.072 g, 0.105 mmol, 79% yield) as a white foam. LCMS: m/e: 685.7 (M+H)$^+$, 1.98 min (method 1). $^1$H NMR (500 MHz, chloroform-d) δ=5.22 (d, J=5.2 Hz, 1H), 4.71 (d, J=1.9 Hz, 1H), 4.60 (s, 1H), 3.67 (s, 3H), 3.14-2.98 (m, 9H), 2.73-2.53 (m, 4H), 2.50-2.43 (m, 1H), 2.33 (t, J=7.5 Hz, 2H), 1.69 (s, 3H), 1.06 (s, 3H), 0.96 (s, 6H), 0.89 (s, 3H), 0.82 (s, 3H), 2.01-0.79 (m, 28H).

Step 3

To a solution of methyl 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)pentanoate (0.072 g, 0.105 mmol) in 1,4-dioxane (2 mL) was added NaOH (1N) (0.526 mL, 0.526 mmol). The mixture was heated to 75° C. for 15 h, cooled to rt, diluted with methanol, and purified by prep HPLC (method 2, retention time=10.4 minutes to give 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)pentanoic acid, TFA (0.055 g, 66% yield) as a white solid. LCMS: m/e: 671.7 (M+H)+, 1.69 min (method 1). $^1$H NMR (400 MHz, acetic acid d$_4$) δ=5.30 (d, J=5.5 Hz, 1H), 4.81 (s, 1H), 4.71 (s, 1H), 3.51-3.43 (m, 1H), 3.34-3.01 (m, 11H), 2.92-2.81 (m, 1H), 2.39 (t, J=7.4 Hz, 2H), 1.73 (s, 3H), 1.23 (s, 3H), 1.09 (s, 3H), 1.01 (s, 3H), 0.94 (s, 3H), 0.91 (s, 3H), 2.28-0.88 (m, 28H).

Example 5

Preparation of 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)propyl)malonic acid, TFA

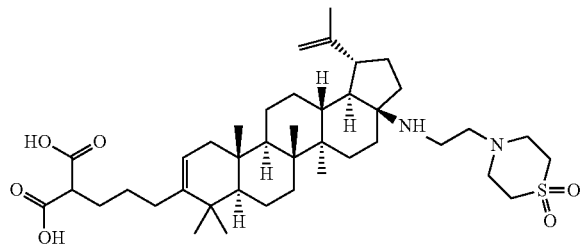

Step 1. Preparation of diethyl 2-(3-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)propyl)malonate

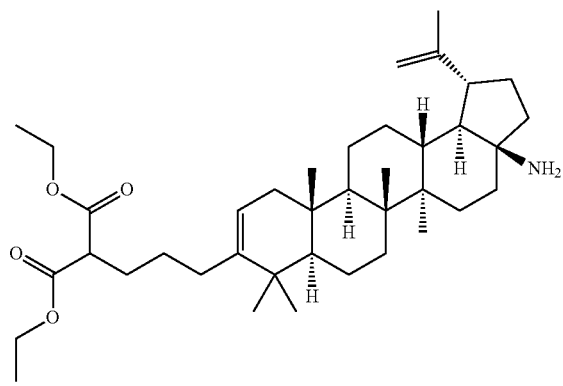

A solution of diethyl allylmalonate (0.053 mL, 0.269 mmol) in THF (1.5 mL) was cooled to 0° C. and 9-BBN (0.5M in THF) (0.574 mL, 0.287 mmol) was added dropwise. The mixture was removed from the ice bath and was stirred at rt for 2 h. To the solution was added a solution of phosphoric acid, potassium salt (1M) (0.448 mL, 0.448 mmol) followed by a solution of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.1 g, 0.179 mmol) in 1,4-dioxane (1.5 mL) and finally 1,1'-bis(diphenylphosphino)ferrocenepalladium(II) dichloride, Toluene (7.38 mg, 8.96 μmol). The mixture was heated to 85° C. for 16 h, then was cooled to rt, diluted with water (15 mL), and was extracted with ethyl acetate (3×15 mL). The organic layers were washed with brine, dried over magnesium sulfate, filtered, and concentrated under reduced pressure. The residue was purified by flash chromatography using a 5-50% EtOAc in hexanes gradient and a 12 g silica gel column to give the title compound (0.077 g, 70.4% yield) as an off-white foam. LCMS: m/e: 610.6 (M+H)+, 2.09 min (method 1). $^1$H NMR (400 MHz, chloroform-d) δ=5.22 (d, J=5.0 Hz, 1H), 4.73 (d, J=2.0 Hz, 1H), 4.60 (dd, J=2.3, 1.3 Hz, 1H), 4.24-4.16 (m, 4H), 3.34 (t, J=7.5 Hz, 1H), 2.54 (td, J=10.9, 5.3 Hz, 1H), 2.10-1.88 (m, 6H), 1.70 (s, 3H), 1.27 (t, J=7.2 Hz, 6H), 1.07 (s, 3H), 0.96 (s, 6H), 0.88 (s, 3H), 1.79-0.80 (m, 24H), 0.82 (s, 3H).

Step 2. Preparation of diethyl 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)propyl)malonate

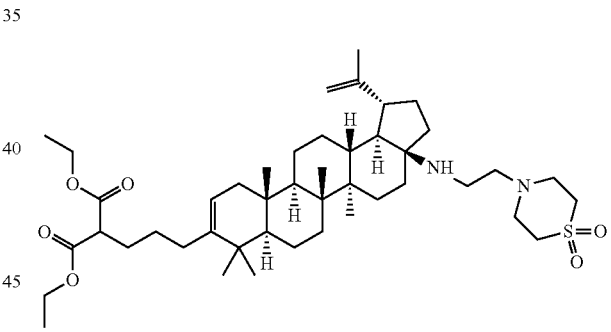

To a sealable flask containing diethyl 2-(3-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)propyl)malonate (0.075 g, 0.123 mmol) was added phosphoric acid, potassium salt (0.131 g, 0.615 mmol), potassium iodide (0.061 g, 0.369 mmol) and 4-(2-chloroethyl)thiomorpholine 1,1-dioxide, HCl (0.086 g, 0.369 mmol). The mixture was diluted with acetonitrile (1.25 mL), flushed with nitrogen, sealed, and heated to 100° C. After heating the mixture for 24 h, it was cooled to rt, diluted with water (7 mL), and extracted with dichloromethane (3×7 mL). The combined organic layers were dried with sodium sulfate, filtered, and concentrated under reduced pressure. The residue was purified by flash chromatography using a 0-50% EtOAc in hexanes gradient and a 12 g silica gel column. The fractions containing the product were combined and concentrated under reduced pressure to give the title compound (0.025 g, 0.032 mmol, 26.4% yield) as an off-white foam. LCMS: m/e: 771.8 (M+H)+, 2.03 min (method 1).

Step 3

To a solution of diethyl 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)propyl)malonate (0.025 g, 0.032 mmol) in 1,4-dioxane (2 mL) was added NaOH (1N) (0.162 mL, 0.162 mmol). The mixture was heated to 75° for 15 h, cooled to rt, diluted with methanol, and purified by prep HPLC (method 2, retention time=8.96 minutes to give 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)propyl)malonic acid, TFA (8.8 mg, 33% yield) as a white solid. LCMS: m/e: 715.7 (M+H)+, 1.64 min (method 1). 1H NMR (400 MHz, acetic acid d4) δ=5.29 (d, J=5.8 Hz, 1H), 4.80 (s, 1H), 4.70 (s, 1H), 3.53-3.41 (m, 2H), 3.34-3.00 (m, 11H), 2.90-2.80 (m, 1H), 1.72 (s, 3H), 1.22 (s, 3H), 1.08 (s, 3H), 1.00 (s, 3H), 0.93 (s, 3H), 0.90 (s, 3H), 2.27-0.86 (m, 28H).

Example 6

Preparation of 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoic acid, TFA

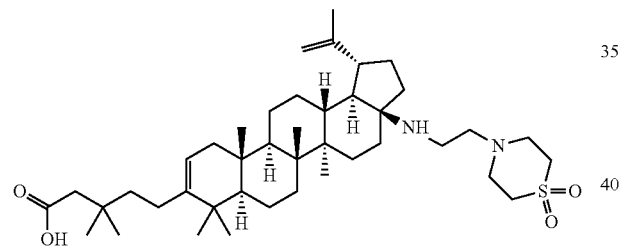

Step 1. Preparation of methyl 5-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoate

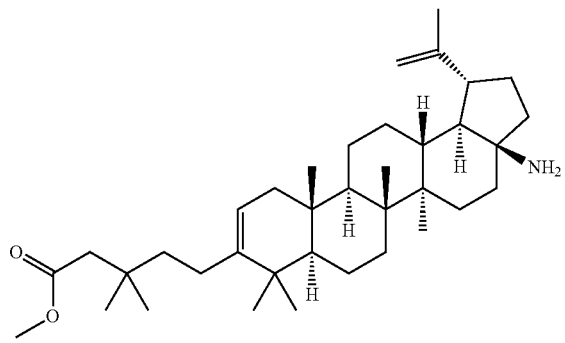

A solution of 4-Pentenoic acid, 3,3-dimethyl-, methyl ester (0.042 mL, 0.269 mmol) in THF (1.5 mL) was cooled to 0° C. and 9-BBN (0.5M in THF) (0.574 mL, 0.287 mmol) was added dropwise. The mixture was removed from the ice bath and was stirred at rt for 2 h. To the solution was added a solution of phosphoric acid, potassium salt (1M) (0.448 mL, 0.448 mmol) followed by a solution of (1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.1 g, 0.179 mmol) in 1,4-dioxane (1.5 mL) and finally 1,1'-bis(diphenylphosphino)ferrocenepalladium(II) dichloride, Toluene (7.38 mg, 8.96 μmol). The mixture was heated to 85° C. for 16 h, then was cooled to rt, diluted with water (15 mL), and was extracted with ethyl acetate (3×15 mL). The organic layers were washed with brine, dried over magnesium sulfate, filtered, and concentrated under reduced pressure. The residue was purified by flash chromatography using a 5-50% ethyl acetate in hexanes gradient and a 12 g silica gel column to give the title compound (0.072 g, 0.130 mmol, 72.8% yield) as an off-white foam. LCMS: m/e: 552 (M+H)+, 2.13 min (method 1). 1H NMR (400 MHz, chloroform-d) δ=5.24 (d, J=5.5 Hz, 1H), 4.73 (d, J=2.0 Hz, 1H), 4.63-4.58 (m, 1H), 3.65 (s, 3H), 2.55 (td, J=10.9, 5.3 Hz, 1H), 2.23 (s, 2H), 2.10-1.88 (m, 4H), 1.70 (s, 3H), 1.07 (s, 3H), 1.02 (s, 6H), 0.98 (s, 3H), 0.96 (s, 3H), 0.90 (s, 3H), 0.83 (s, 3H), 1.81-0.80 (m, 24H).

Step 2. Preparation of methyl 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoate

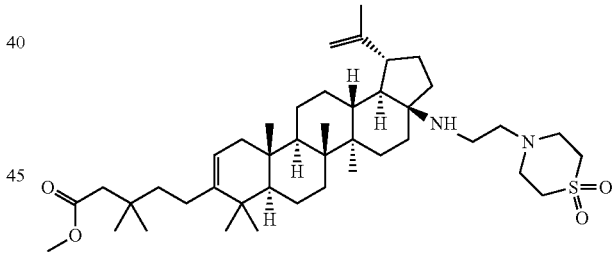

To a sealable flask containing methyl 5-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoate (0.07 g, 0.127 mmol) was added phosphoric acid, potassium salt (0.135 g, 0.634 mmol), potassium iodide (0.063 g, 0.381 mmol), and 4-(2-chloroethyl)thiomorpholine 1,1-dioxide, HCl (0.089 g, 0.381 mmol). The mixture was diluted with acetonitrile (1.25 mL), flushed with nitrogen, sealed, and heated to 100° C. After 15 h of heating, the mixture was cooled to rt, diluted with water (7 mL), and extracted with dichloromethane (3×7 mL). The combined organic layers were dried with sodium sulfate, filtered, and concentrated under reduced pressure. The residue was purified by flash chromatography using a 0-50% ethyl acetate in hexanes gradient and a 12 g silica gel column to give the title compound (52.4 mg, 58% yield) as a light-yellow film. LCMS: m/e: 713.7 (M+H)+, 2.10 min (method 1). ¹H NMR (400 MHz, chloroform-d) δ=5.24 (d, J=5.3 Hz, 1H), 4.71 (d, J=2.0 Hz, 1H), 4.62-4.55 (m, 1H), 3.65 (s, 3H), 3.14-2.98 (m, 8H), 2.73-2.53 (m, 4H), 2.50-2.42 (m, 1H), 2.23 (s, 2H), 1.69 (s, 3H), 1.06 (s, 3H), 1.02 (s, 6H), 0.98 (s, 3H), 0.97 (s, 3H), 0.90 (s, 3H), 0.82 (s, 3H), 2.01-0.80 (m, 27H).

Step 3

To a solution of methyl 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoate (0.052 g, 0.073 mmol) in 1,4-dioxane (2 mL) was added sodium hydroxide (1N) (0.365 mL, 0.365 mmol). The mixture was heated to 75° C. for 21 h, then was cooled to rt. The reaction had not completed, so an additional 0.2 mL of 1N NaOH was added and the mixture was again heated to 75° C. for 16 h. The mixture was cooled to rt, diluted with methanol, and purified by prep HPLC (method 2, retention time=11.6 minutes) to give 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoic acid, TFA (0.0346 g, 0.0425 mmol, 58% yield) as a white solid. LCMS: m/e: 699.7 (M+H)⁺, 1.84 min (method 1). ¹H NMR (400 MHz, acetic acid d₄) δ=5.29 (d, J=5.5 Hz, 1H), 4.81 (s, 1H), 4.71 (s, 1H), 3.52-3.44 (m, 1H), 3.34-3.01 (m, 11H), 2.91-2.81 (m, 1H), 2.29 (s, 2H), 1.73 (s, 3H), 1.23 (s, 3H), 1.09 (s, 3H), 1.06 (s, 6H), 1.02 (s, 3H), 0.95 (s, 3H), 0.91 (s, 3H), 2.26-0.88 (m, 26H).

Preparation of benzyl 1-ethoxy-4-methylenecyclohexanecarboxylate and tert-pentyl 1-ethoxy-4-methylenecyclohexanecarboxylate

Step 1. Preparation of 8-ethoxy-1,4-dioxaspiro[4.5]decane-8-carboxylic acid

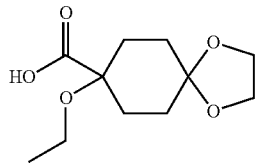

A solution of 1,4-dioxaspiro[4.5]decan-8-one (1.0 g, 6.40 mmol) in bromoform (6.15 mL, 64.0 mmol) was cooled to 0° C. To the solution was added a solution of potassium hydroxide (2.87 g, 51.2 mmol) in ethanol (20 mL) dropwise over 1 h. After stirring the mixture for an additional 22 h, the mixture was concentrated under reduced pressure, then was made acidic by slowly adding 6N HCl. The mixture was diluted with water (20 mL) and was extracted with dichloromethane (3×20 mL). The combined organic layers were dried over sodium sulfate, filtered, and concentrated under reduced pressure. The residue was dissolved in 1,4-dioxane (30 mL) and NaOH (20% wt.) (12.80 g, 64.0 mmol) was added. The mixture was heated to 75° C. for 4 h then cooled to rt and concentrated under reduced pressure. The mixture was diluted with 30 mL of water and washed with dichloromethane (20 mL). The separated aqueous layer was made acidic by adding 1N HCl then was extracted with ethyl acetate (4×30 mL). The combined organic layers were washed with brine, dried over magnesium sulfate, filtered, and concentrated under reduced pressure. The product was used in the next step with no additional purification. LCMS: m/e: 229.2 (M−H)⁻, 0.94 min (method 2).

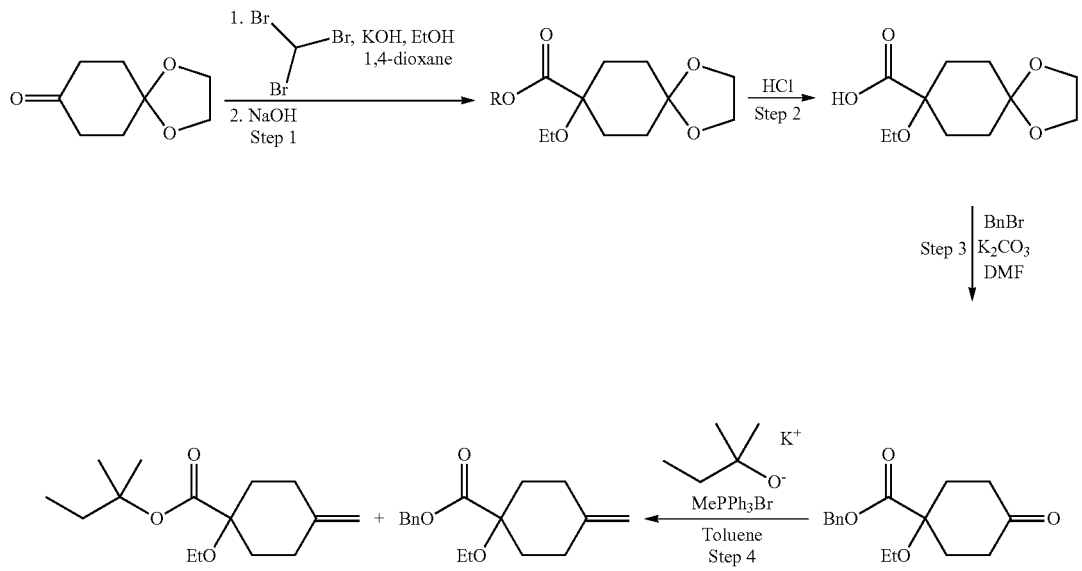

Step 2. Preparation of 1-ethoxy-4-oxocyclohexanecarboxylic acid

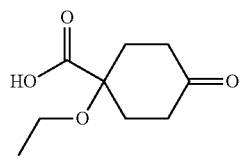

To a solution of the 8-ethoxy-1,4-dioxaspiro[4.5]decane-8-carboxylic acid in 1,4-dioxane (20 mL) was added HCl (6N) (7.53 mL, 45.2 mmol) and the mixture was stirred at rt for 16 h. The reaction mixture was diluted with water (30 mL) and extracted with ethyl acetate (3×40 mL). The organic layers were washed with brine, dried over magnesium sulfate, filtered, and concentrated under reduced pressure to give 1-ethoxy-4-oxocyclohexanecarboxylic acid (0.777 g, 4.17 mmol, 65% yield over 2 steps) as a red oil. $^1$H NMR (500 MHz, CHLOROFORM-d) δ=3.59 (q, J=7.0 Hz, 2H), 2.66-2.55 (m, 2H), 2.42-2.33 (m, 4H), 2.24-2.15 (m, 2H), 1.31 (t, J=6.9 Hz, 3H).

Step 3. Preparation of benzyl 1-ethoxy-4-oxocyclohexanecarboxylate

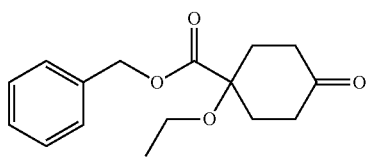 [SMILES: CCOC1(C(=O)OCc2ccccc2)CCC(=O)CC1]

To a solution of 1-ethoxy-4-oxocyclohexanecarboxylic acid (0.777 g, 4.17 mmol) in DMF (15 mL) was added potassium carbonate (1.153 g, 8.35 mmol) followed by benzyl bromide (0.546 mL, 4.59 mmol). The mixture was heated at 60° C. for 18 h, then cooled to rt. The mixture was diluted with water (30 mL) and extracted with ethyl acetate (2×30 mL). The organic layers were washed with water (3×30 mL), then with brine and dried over magnesium sulfate. The drying agent was removed by filtration and the filtrate was concentrated under reduced pressure. The residue was purified by flash chromatography using a 0-25% ethyl acetate in hexanes gradient and a 24 g silica gel column to give benzyl 1-ethoxy-4-oxocyclohexanecarboxylate (0.9 g, 3.26 mmol, 78% yield) as a light-yellow oil. $^1$H NMR (400 MHz, CHLOROFORM-d) δ=7.40-7.32 (m, 5H), 5.21 (s, 2H), 3.48 (q, J=6.9 Hz, 2H), 2.65-2.54 (m, 2H), 2.39-2.27 (m, 4H), 2.20-2.09 (m, 2H), 1.24 (t, J=7.0 Hz, 3H).

Step 4. Preparation of benzyl 1-ethoxy-4-methylenecyclohexanecarboxylate and tert-pentyl 1-ethoxy-4-methylenecyclohexanecarboxylate

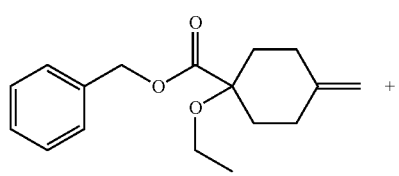

+

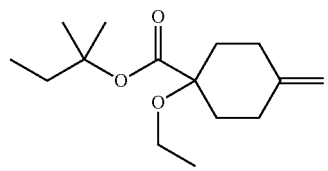

To a suspension of methyltriphenylphosphonium bromide (0.517 g, 1.448 mmol) in toluene (2 mL) was added potassium 2-methylbutan-2-olate (0.882 mL, 1.520 mmol) (ref. *J. Org. Chem.* 1982, 47, 1845-1855). The yellow suspension was stirred at rt for 30 minutes and a solution of benzyl 1-ethoxy-4-oxocyclohexanecarboxylate (0.2 g, 0.724 mmol) in toluene (2 mL) was added. The yellow suspension was heated at 50° C. for 2 h. The mixture was cooled to rt, diluted with water (20 mL), and extracted with ethyl acetate (3×20 mL). The organic layers were washed with brine, dried over magnesium sulfate, filtered, and concentrated under reduced pressure. The residue was purified by flash chromatography using a 0-20% ethyl acetate in hexanes gradient and a 24 g silica gel column to give 84 mg of a mixture of the two title compounds as a clear oil (0.4:0.6 ratio of benzyl ester:tert-pentyl ester). $^1$H NMR (benzyl ester) (500 MHz, CHLOROFORM-d) δ=7.39-7.30 (m, 5H), 5.18 (s, 2H), 4.65 (s, 2H), 3.41 (q, J=7.1 Hz, 2H), 2.39-2.30 (m, 2H), 2.18-2.12 (m, 2H), 2.08-1.96 (m, 2H), 1.88-1.77 (m, 2H), 1.20 (t, J=6.9 Hz, 3H). $^1$H NMR (tert-pentyl ester) (500 MHz, CHLOROFORM-d) δ=4.65 (s, 2H), 3.45 (q, J=6.9 Hz, 2H), 2.39-2.29 (m, 2H), 2.19-2.12 (m, 2H), 2.08-1.96 (m, 2H), 1.88-1.76 (m, 4H), 1.44 (s, 6H), 1.24 (t, J=7.0 Hz, 3H), 0.90 (t, J=7.5 Hz, 3H).

Preparation of benzyl 1-methoxy-4-methylenecyclohexanecarboxylate and tert-pentyl 1-methoxy-4-methylenecyclohexanecarboxylate

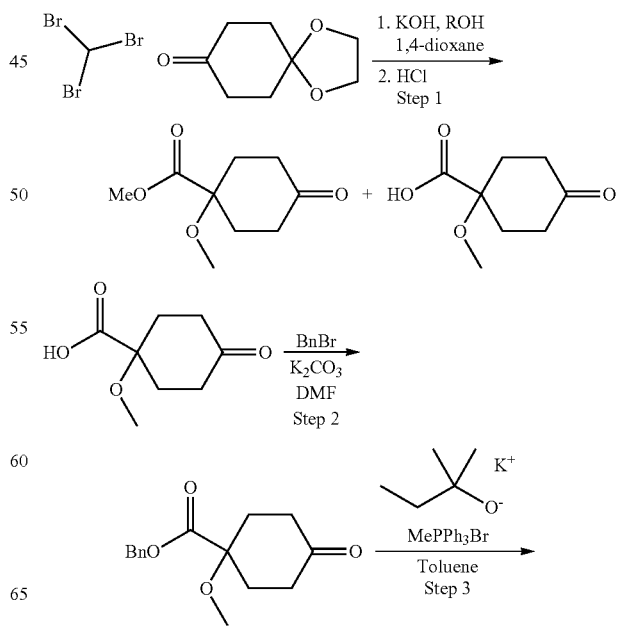

-continued

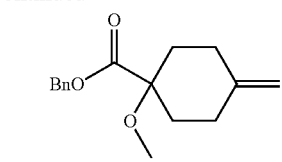

+

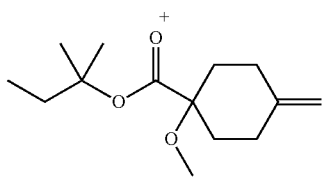

Step 1. Preparation of A Solution of methyl 1-methoxy-4-oxocyclohexanecarboxylate and 1-methoxy-4-oxocyclohexanecarboxylic acid

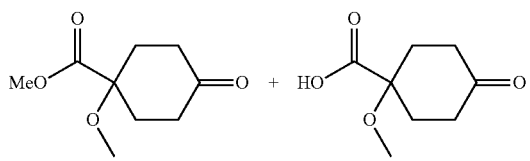

A solution of 1,4-dioxaspiro[4.5]decan-8-one (1.0 g, 6.40 mmol) in bromoform (6.15 mL, 64.0 mmol) was cooled to 0° C. To the solution was added a solution of potassium hydroxide (2.87 g, 51.2 mmol) in methanol (15 mL) dropwise over 2.5 h. After stirring the mixture for 23 h, the mixture was extracted with ethyl acetate (3×20 mL) and the organic layers were washed with brine, dried over magnesium sulfate, filtered, and concentrated under reduced pressure to give 1.2 g of a crude yellow oil which partially solidified upon standing. To a solution of the crude product in 1,4-dioxane (25 mL) was added HCl (6M) (9.25 mL, 55.5 mmol) and the mixture was stirred for 23 h at rt. The mixture was then diluted with water (25 mL) and extracted with ethyl acetate (3×25 mL). The organic layers were washed with brine, dried over magnesium sulfate, filtered, and concentrated under reduced pressure. The residue was purified by flash chromatography using a 25-75% ethyl acetate in hexanes gradient and a 40 g silica gel column to give two isolates. Isolate 1 (Rf=0.54, 1:1 ethyl acetate:hexanes with 0.5% acetic acid added, stained with Hanessian's stain) was a light red oil consistent with the methyl ester product (0.463 g, 2.49 mmol, 39% over 2 steps). Isolate 2 (Rf=0.13, 1:1 ethyl acetate:hexanes with 0.5% acetic acid added, stained with Hanessian's stain) was a light red oil consistent with the carboxylic acid (0.253 g, 1.47 mmol, 23% over 2 steps) which solidified upon standing at rt. $^1$H NMR (isolate 1) (500 MHz, CHLOROFORM-d) δ=3.80 (s, 3H), 3.37 (s, 3H), 2.63-2.53 (m, 2H), 2.37-2.29 (m, 4H), 2.18-2.09 (m, 2H). $^1$H NMR (isolate 2) (500 MHz, CHLOROFORM-d) δ=11.00 (br. s., 1H), 3.41 (s, 3H), 2.62-2.52 (m, 2H), 2.39-2.31 (m, 4H), 2.21-2.13 (m, 2H).

Step 2. Preparation of benzyl 1-methoxy-4-oxocyclohexanecarboxylate

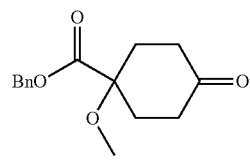

To a flask containing 1-methoxy-4-oxocyclohexanecarboxylic acid (0.253 g, 1.469 mmol) was added potassium carbonate (0.406 g, 2.94 mmol). The mixture was diluted with DMF (5 mL) and benzyl bromide (0.192 mL, 1.616 mmol) was added. The mixture was heated to 60° C. for 15.5 h, then cooled to rt, diluted with water (20 mL), and extracted with ethyl acetate (20 mL). The organic layer was washed with water three times, then with sat. aq. NaCl, and was finally dried over magnesium sulfate. The drying agent was removed by filtration and the filtrate was concentrated under reduced pressure. The residue was purified by flash chromatography using a 0-50% EtOAc in hexanes gradient and a 12 g silica gel column to give the title product (0.294 g, 1.12 mmol, 76% yield). $^1$H NMR (500 MHz, CHLOROFORM-d) δ=7.41-7.31 (m, 5H), 5.23 (s, 2H), 3.35 (s, 3H), 2.62-2.53 (m, 2H), 2.37-2.28 (m, 4H), 2.19-2.10 (m, 2H).

Step 3. Preparation of tert-pentyl 1-methoxy-4-methylenecyclohexanecarboxylate

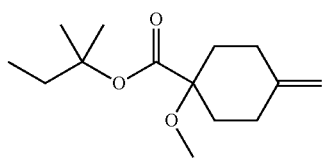 [SMILES: C=C1CCC(OC)(C(=O)OC(C)(C)CC)CC1]

To a suspension of methyltriphenylphosphonium bromide (0.425 g, 1.189 mmol) in toluene (2 mL) was added potassium 2-methylbutan-2-olate (0.725 mL, 1.249 mmol) (ref. *J. Org. Chem.* 1982, 47, 1845-1855). The yellow suspension was stirred at rt for 30 minutes and a solution of benzyl 1-methoxy-4-oxocyclohexanecarboxylate (0.156 g, 0.595 mmol) in toluene (2 mL) was added. The yellow suspension was heated at 50° C. for 2 h. The mixture was cooled to rt, diluted with water (20 mL), and extracted with ethyl acetate (3×20 mL). The combined organic layers were washed with brine, dried over magnesium sulfate, filtered, and concentrated under reduced pressure. The residue was purified by flash chromatography using a 0-20% EtOAc in hexanes gradient and a 24 g silica gel column to give the title product (0.085 g, 0.354 mmol, 60% yield). $^1$H NMR (500 MHz, CHLOROFORM-d) δ=4.67 (s, 2H), 3.32 (s, 3H), 2.38-2.28

(m, 2H), 2.21-2.12 (m, 2H), 2.04-1.97 (m, 2H), 1.87-1.78 (m, 4H), 1.47 (s, 6H), 0.93 (t, J=7.5 Hz, 3H).

Example 7

Preparation of 5-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)-2,2-dimethylpentanoic acid, TFA

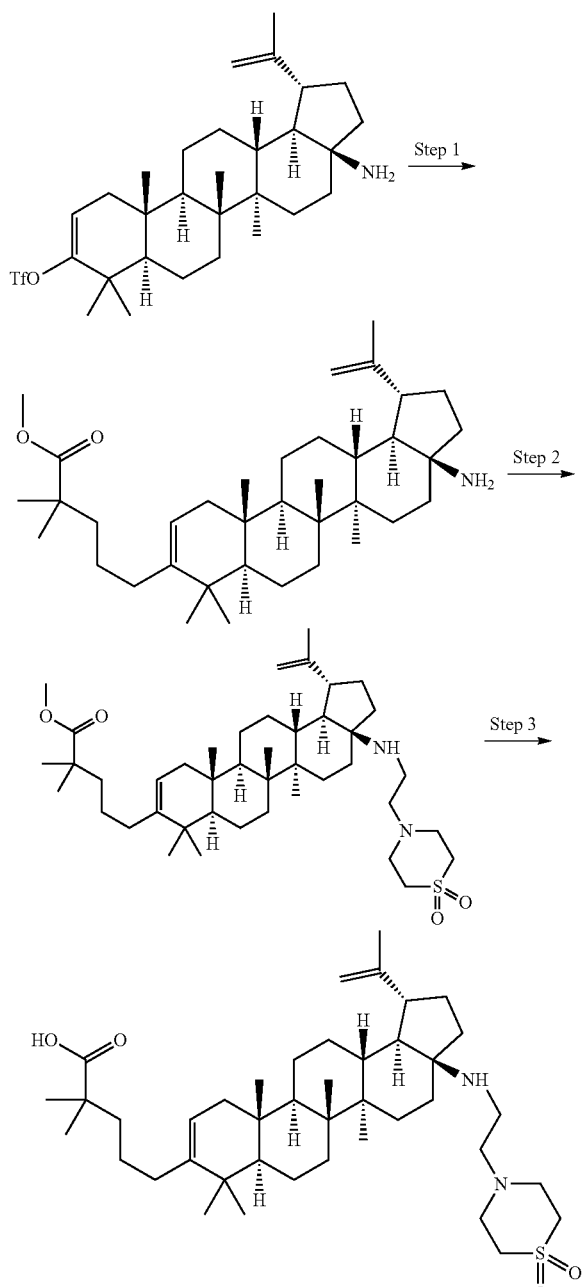

Example 7

Step 1. Preparation of methyl 5-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-2,2-dimethylpentanoate To a solution of methyl 2,2-dimethylpent-4-enoate (0.036 g, 0.251 mmol) in THF (1.5 mL) was added 9-BBN (0.574 mL, 0.287 mmol) dropwise. The mixture was stirred at rt for 2 h. To the mixture was added a solution of phosphoric acid, potassium salt (1M) (0.448 mL, 0.448 mmol) followed by a solution of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.1 g, 0.179 mmol) in 1,4-dioxane (1.5 mL) and finally 1,1'-bis(diphenylphosphino)ferrocenepalladium(II) dichloride, toluene (7.38 mg, 8.96 µmol). The mixture was heated to 85° C. for 17 h, then cooled to rt and diluted with water (15 mL). The mixture was extracted with ethyl acetate (3×15 mL). The organic layers were washed with brine, dried over magnesium sulfate, filtered, and concentrated under reduced pressure. The residue was purified by flash chromatography using a 5-50% ethyl acetate in hexanes gradient and a 12 g silica gel column to give the title compound (99 mg, 0.179 mmol, 100% yield) as a clear, colorless film. LCMS: m/e: 552.7 (M+H)$^+$, 2.14 min (method 1). $^1$H NMR (500 MHz, CHLOROFORM-d) δ=5.20 (d, J=5.5 Hz, 1H), 4.72 (d, J=1.9 Hz, 1H), 4.60 (dd, J=2.1, 1.3 Hz, 1H), 3.65 (s, 3H), 2.54 (td, J=10.9, 5.3 Hz, 1H), 1.69 (s, 3H), 1.17 (s, 6H), 1.07 (s, 3H), 0.96 (s, 3H), 0.95 (s, 3H), 0.87 (s, 3H), 0.82 (s, 3H), 2.11-0.78 (m, 30H).

Step 2. Preparation of methyl 5-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)-2,2-dimethylpentanoate To a sealable flask containing methyl 5-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)-2,2-dimethylpentanoate (99 mg, 0.179 mmol) was added phosphoric acid, potassium salt (190 mg, 0.897 mmol), potassium iodide (89 mg, 0.538 mmol), and 4-(2-chloroethyl)thiomorpholine 1,1-dioxide, HCl (126 mg, 0.538 mmol). The mixture was diluted with acetonitrile (2 mL), flushed with nitrogen, sealed, and heated to 100° C. for 16 h. The mixture was cooled to rt, diluted with water (10 mL), and the solids that formed were collected by filtration and washed with water to give methyl 5-((1R,3aS,5aR,5bR,7aR,11aS, 11bR,13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2,2-dimethylpentanoate (0.093 g, 0.130 mmol, 72.7% yield) as a tan solid. LCMS: m/e: 713.6 (M+H)$^+$, 2.08 min (method 1).

Step 3

To a solution of methyl 5-((1R,3aS,5aR,5bR,7aR,11aS, 11bR,13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2,2-dimethylpentanoate (0.093 g, 0.130 mmol) in 1,4-dioxane (3 mL) was added NaOH (1N) (0.652 mL, 0.652 mmol) and the mixture was heated to 75° C. After heating the mixture for 42 h, an additional 0.5 mL of NaOH was added to the mixture and it was again heated to 75° C. After 23 additional hours of heating, the mixture was cooled to rt and was purified by prep HPLC (method 6, retention time=8.6 minutes). Fractions containing the product were combined and concentrated under reduced pressure to give the title compound (0.032 g, 0.039 mmol, 30% yield) as a white solid. LCMS: m/e: 699.6 (M+H)+, 1.86 min (method 1). $^1$H NMR (500 MHz, Acetic Acid-$d_4$) δ=5.28 (d, J=5.8 Hz, 1H), 4.81 (s, 1H), 4.71 (s, 1H), 3.49 (dt, J=12.7, 3.3 Hz, 1H), 3.33-3.00 (m, 11H), 2.89-2.81 (m, 1H), 1.73 (s, 3H), 1.23 (s, 3H), 1.20 (s, 6H), 1.09 (s, 3H), 1.00 (s, 3H), 0.93 (s, 3H), 0.91 (s, 3H), 2.27-0.87 (m, 28H).

Example 8

Preparation of 4-(((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)methyl)-1-ethoxycyclohexanecarboxylic acid

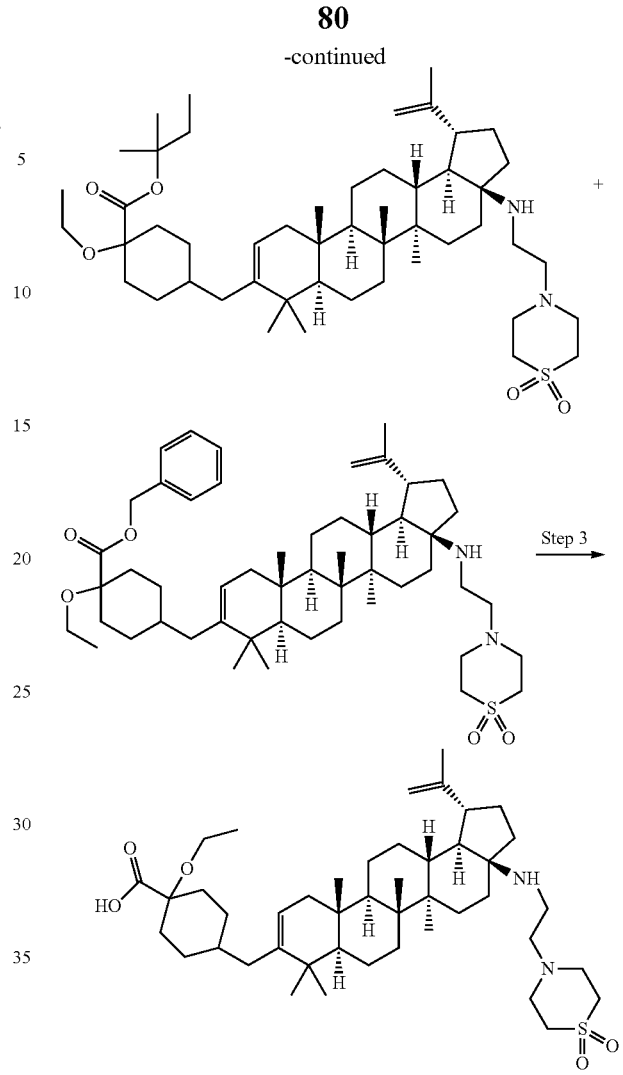

Example 8

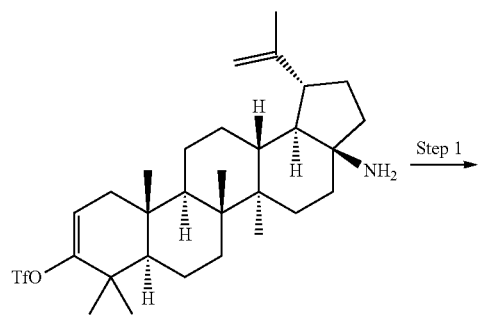

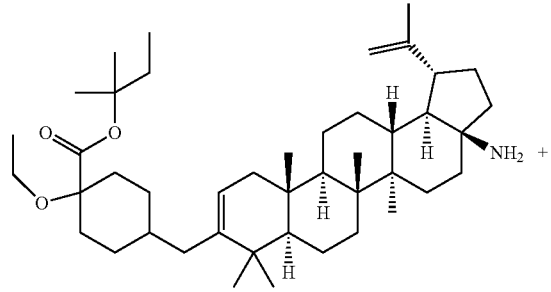

Step 1. Preparation of tert-pentyl 4-(((1R,3aS,5aR, 5bR,7aR,11aS,11bR,13aR,13bR)-3a-amino-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) methyl)-1-ethoxycyclohexanecarboxylate and benzyl 4-(((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) methyl)-1-ethoxycyclohexanecarboxylate A solution of the mixture of benzyl 1-ethoxy-4-methyl-enecyclohexanecarboxylate and tert-pentyl 1-ethoxy-4-methylenecyclohexanecarboxylate (84 mg) (0.4:0.6 ratio of benzyl ester:tert-pentyl ester) in THF (2 mL) was cooled to 0° C. and 9-BBN (0.5M in THF) (0.67 mL, 0.335 mmol) was added dropwise. The mixture was removed from the ice bath and was stirred at rt for 2 h. To the solution was added a solution of phosphoric acid, potassium salt (1M) (0.224 mL, 0.448 mmol) followed by a solution of (1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yltrifluoromethanesulfonate (0.1 g, 0.179 mmol)

in 1,4-dioxane (2 mL) and finally 1,1'-bis(diphenylphosphino)ferrocenepalladium(II) dichloride, toluene (11 mg, 0.013 mmol). The mixture was heated to 85° C. for 18 h, then cooled to rt, diluted with water (20 mL), and extracted with ethyl acetate (3×20 mL). The organic layers were washed with brine, dried over magnesium sulfate, filtered, and concentrated under reduced pressure. The residue was purified by flash chromatography using a 0-60% EtOAc in hexanes gradient and a 24 g silica gel column to give 83 mg of the title compounds which were directly used in the next step of the reaction. LCMS: m/e: 664.8 (M+H)$^+$, 2.52 min; 684.7 (M+H)$^+$, 2.43 minutes (method 1).

Step 2. Preparation of tert-pentyl 4-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)-1-ethoxycyclohexanecarboxylate and benzyl 4-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)-1-ethoxycyclohexanecarboxylate To a sealable flask containing 83 mg of the mixture of esters formed in step 1 was added phosphoric acid, potassium salt (0.133 g, 0.625 mmol), potassium iodide (0.033 g, 0.200 mmol), and 4-(2-chloroethyl)thiomorpholine 1,1-dioxide, HCl (0.088 g, 0.375 mmol). The mixture was diluted with acetonitrile (2 mL), flushed with nitrogen, sealed, and heated to 100° C. for 17 h. The mixture was cooled to rt, diluted with water (20 mL), and extracted with ethyl acetate (3×20 mL). The organic layers were washed with brine, dried over magnesium sulfate, filtered, and concentrated under reduced pressure. The residue was purified by flash chromatography using a 0-50% ethyl acetate in hexanes gradient and a 24 g silica gel column to give 93 mg of a mixture of the title compounds. LCMS: m/e: 845.9 (M+H)$^+$, 2.31 min; 825.9 (M+H)$^+$, 2.41 minutes (method 1).

Step 3

To a solution of the mixture of products from step 2 (93 mg) in 1,4-dioxane (3 mL) and methanol (1 mL) was added sodium hydroxide (1N) (0.563 mL, 0.563 mmol) along with additional solid sodium hydroxide (0.045 g, 1.127 mmol). The mixture was heated to reflux for 5 days, then was cooled to rt, diluted with water (15 mL), and acidified using 1N HCl. The solids that formed were collected by filtration then were dissolved in dioxane and methanol and purified by prep HPLC to give the TFA salt of the title compound (12 mg, 0.014 mmol) as a white solid. LCMS: m/e: 755.7 (M+H)$^+$, 1.95 min (method 1). $^1$H NMR (500 MHz, Acetic acid-d$_4$) δ=5.33-5.28 (m, 1H), 4.81 (s, 1H), 4.71 (s, 1H), 3.53-3.41 (m, 3H), 3.33-3.11 (m, 9H), 3.10-3.02 (m, 2H), 2.87 (td, J=10.6, 5.0 Hz, 1H), 1.73 (s, 3H), 1.23 (s, 3H), 1.10 (s, 3H), 2.35-0.87 (m, 45H).

Example 9

Preparation of 4-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methyl)-1-methoxycyclohexanecarboxylic acid

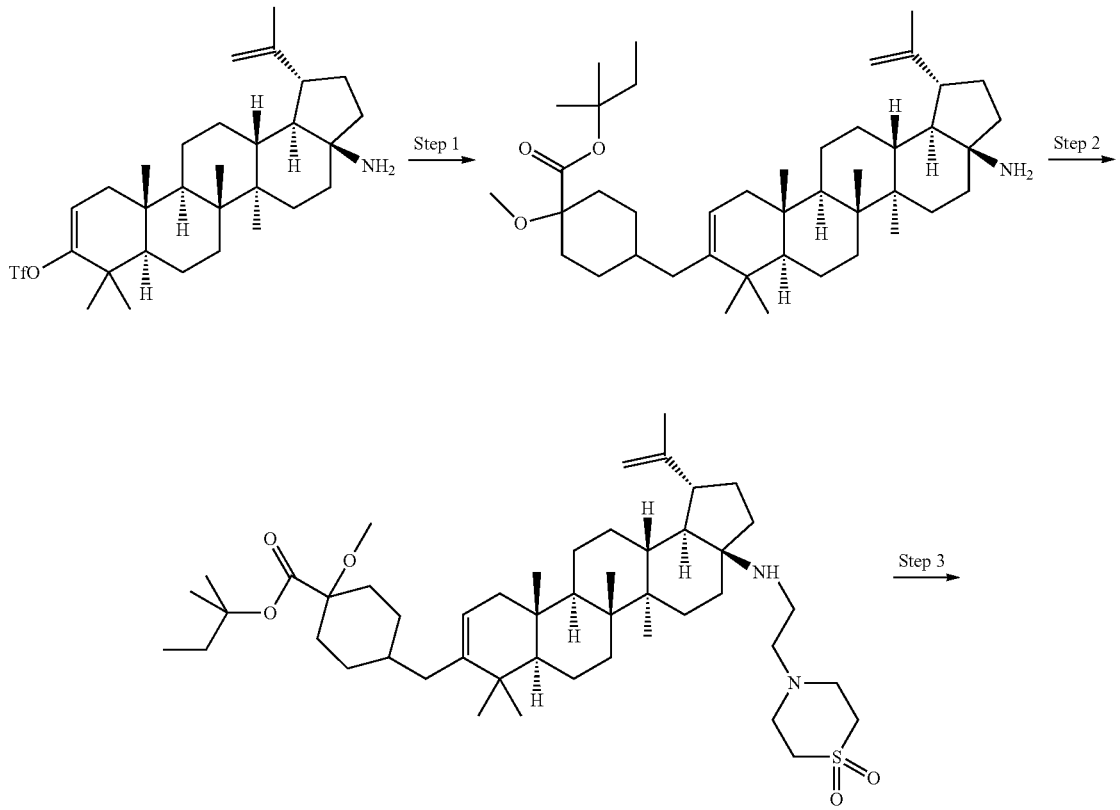

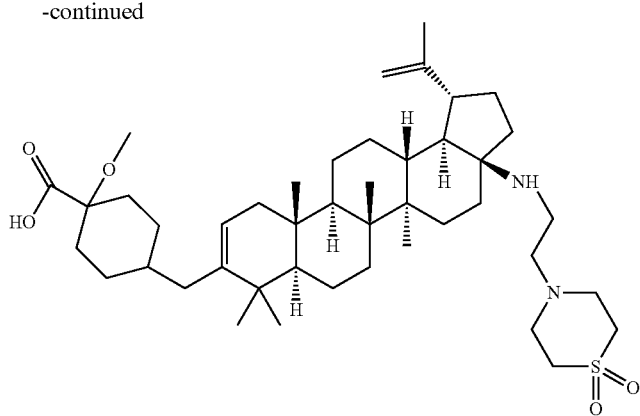

Example 9

Step 1. Preparation of tert-pentyl 4-((((1R,3aS,5aR, 5bR,7aR,11aS,11bR,13aR,13bR)-3a-amino-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) methyl)-1-methoxycyclohexanecarboxylate A solution of tert-pentyl 1-methoxy-4-methylenecyclohexanecarboxylate (0.075 g, 0.312 mmol) in THF (2 mL) was cooled to 0° C. and 9-BBN (0.5M in THF) (0.672 mL, 0.336 mmol) was added dropwise. The mixture was removed from the ice bath and was stirred at rt for 2 h. To the solution was added a solution of phosphoric acid, potassium salt (1M) (0.336 mL, 0.672 mmol) followed by a solution of (1R,3aS, 5aR,5bR,7aR,11aR,11bR,13aR,13bR)-3a-amino-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yltrifluoromethanesulfonate (0.15 g, 0.269 mmol) in 1,4-dioxane (2 mL) and finally 1,1'-bis (diphenylphosphino)ferrocenepalladium(II) dichloride, toluene (0.011 g, 0.013 mmol). The mixture was heated to 85° C. for 4 h, then cooled to rt and stirred overnight. The mixture was diluted with water (20 mL) and extracted with ethyl acetate (3×20 mL). The organic layers were washed with brine, dried over magnesium sulfate, filtered, and concentrated under reduced pressure. The residue was purified by flash chromatography using a 0-50% ethyl acetate in hexanes gradient and a 24 g silica gel column to give the title compound (117 mg, 0.18 mmol, 67%) as an off-white solid. LCMS: m/e: 650.8 (M+H)+, 2.35 min (method 1).

Step 2. Preparation of tert-pentyl 4-(((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)methyl)-1-methoxycyclohexanecarboxylate To a sealable flask containing tert-pentyl 4-(((1R,3aS,5aR, 5bR,7aR,11aS,11bR,13aR,13bR)-3a-amino-5a,5b,8,8,11a-pentamethyl-1- (prop-1-en-2-yl)-2,3,3a,4,5,5a,5b,6,7,7a,8, 11,11a,11b,12,13,13a,13b-octadecahydro-1H-cyclopenta[a] chrysen-9-yl)methyl)-1-methoxycyclohexanecarboxylate (0.117 g, 0.180 mmol) was added phosphoric acid, potassium salt (0.191 g, 0.900 mmol), potassium iodide (0.05 g, 0.301 mmol), and 4-(2-chloroethyl)thiomorpholine 1,1-dioxide, HCl (0.126 g, 0.540 mmol). The mixture was diluted with acetonitrile (2 mL), flushed with nitrogen, sealed, and heated to 100° C. for 16 h. The mixture cooled to rt, diluted with water (15 mL), and extracted with ethyl acetate (3×20 mL). The organic layers were washed with brine, dried over magnesium sulfate, filtered, and concentrated under reduced pressure. The residue was purified by flash chromatography using a 0-50% ethyl acetate in hexanes gradient and a 24 g silica gel column to give 174 mg of material. LCMS: m/e: 811.7 (M+H)+, 2.31 min (method 1).

Step 3

To a solution of tert-pentyl 4-(((1R,3aS,5aR,5bR,7aR, 11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)methyl)-1-methoxycyclohexanecarboxylate (0.138 g, 0.170 mmol) in dichloromethane (3 mL) was added TFA (1.5 mL, 19.47 mmol). The mixture was stirred at rt for 30 minutes, then concentrated under reduced pressure and purified by prep HPLC (method 6, retention time=10.2 minutes). The fractions containing the product were combined and concentrated under reduced pressure. The material obtained was purified a second time by prep HPLC (method 7, retention time 11.2 minutes) to give the TFA salt of the title product (0.016 g, 0.017 mmol, 11%) as a white solid. LCMS: m/e: 741.8 (M+H)+, 1.83 min (method 1). $^1$H NMR (500 MHz, Acetic) δ=5.34-5.28 (m, 1H), 4.81 (s, 1H), 4.71 (s, 1H), 3.50-3.44 (m, 1H), 3.29 (s, 3H), 3.32-3.02 (m, 11H), 2.91-2.83 (m, 1H), 1.73 (s, 3H), 1.23 (s, 3H), 1.10 (s, 3H), 2.35-0.86 (m, 42H).

Example 10

Preparation of 6-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)hexanoic acid

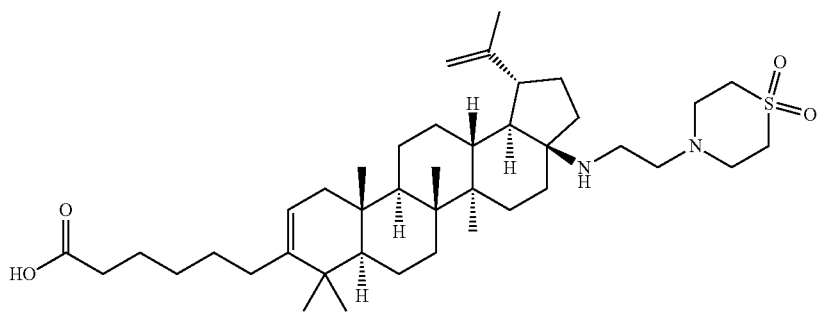

Step 1. Preparation of methyl 6-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)hexanoate

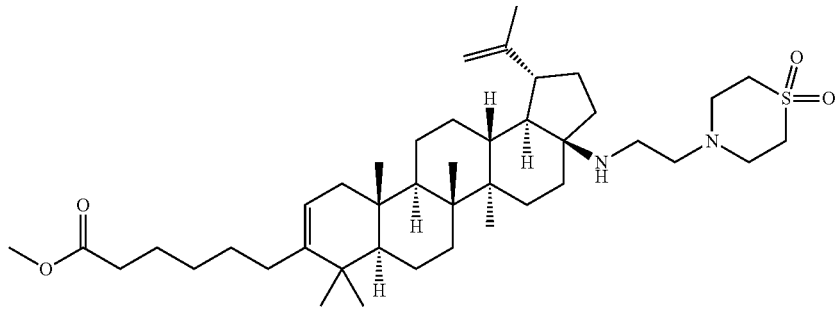

A solution of methyl hex-5-enoate (21.4 mg, 0.167 mmol) in THF (3 mL) under argon was cooled to 0° C. and 9-BBN (0.5 M in THF) (0.356 mL, 0.178 mmol) was added dropwise. The reaction mixture was warmed to rt and was stirred for 2 h. A solution of potassium phosphate tribasic (1M) (0.278 mL, 0.278 mmol) was added to the reaction mixture followed by a solution of (1R,3aS,5aR,5bR,7aR,11aR,11bR,13aR,13bR)-3a-((2-(1,1-dioxidothiomorpholino)ethyl)amino)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl triflouromethanesulfonate (80 mg, 0.111 mmol) in dioxane (3.00 mL). $PdCl_2(dppf) \cdot CH_2Cl_2$ adduct (4.5 mg, 5.6 µmol) was then added and the reaction mixture was stirred for 16 h at 85° C. The reaction mixture was cooled to room temperature and was diluted with water (10 mL). The aqueous layer was extracted with ethyl acetate (3×10 mL). The combined organic layers were dried (sodium sulfate) and concentrated under vacuum. The product was purified by column chromatography on silica gel (0%>50% ethyl acetate in hexanes) to afford methyl 6-((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) hexanoate (48.2 mg, 62% yield). LC/MS: m/e 699.5 $(M+H)^+$, 2.45 min (method 3).

Step 2

To a solution of methyl 6-((1R,3aS,5aR,5bR,7aR,11aS, 11bR,13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)hexanoate (48.2 mg, 0.069 mmol) in 1,4-dioxane (2 mL) and ethanol (1 mL) was added NaOH (5 N) (1 mL). The reaction mixture was heated for 16 h at 100° C. The mixture was cooled to room temperature and was concentrated. The residue was taken up in methanol and dioxane and was purified by prep HPLC (Method 9, $t_R$=7.32 min) to give the TFA salt of 6-((1R, 3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)hexanoic acid (20.2 mg, 35% yield) as a white solid. LC/MS m/e 685.5 $(M+H)^+$, 2.33 min (ionization peak, no UV) (method 3). $^1$H NMR (400 MHz, CHLOROFORM-d) δ 5.22 (d, J=5.0 Hz, 1H), 4.80 (s, 1H), 4.71 (s, 1H), 3.42 (d, J=11.5 Hz, 1H), 3.25-3.11 (m, 7H), 3.07 (br. s., 2H), 2.94-2.85 (m, J=10.3 Hz, 3H), 2.37 (td, J=7.6, 3.1 Hz, 2H), 2.27-0.83 (m, 30H), 1.71 (s, 3H), 1.19 (s, 3H), 1.06 (s, 3H), 0.99 (s, 3H), 0.91 (s, 3H), 0.85 (s, 3H).

Example 11

4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)butanoic acid

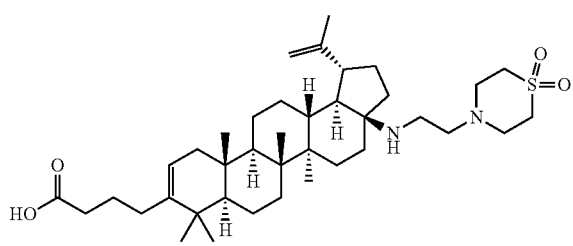

Step 1. Preparation of methyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)butanoate

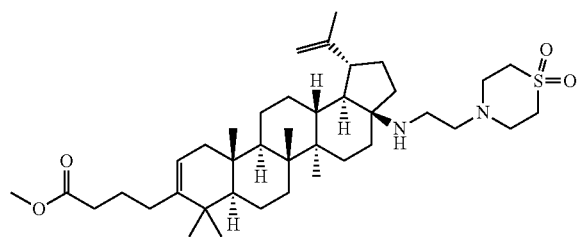

A solution of methyl but-3-enoate (16.7 mg, 0.167 mmol) in THF (3 mL) under argon was cooled to 0° C. and 9-BBN (0.5 M in THF) (0.356 mL, 0.178 mmol) was added dropwise. The reaction mixture was warmed to rt and was stirred for 2 h. A solution of potassium phosphate tribasic (1M) (59.0 mg, 0.278 mmol) was added to the reaction mixture followed by a solution of (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (80 mg, 0.111 mmol) in dioxane (3.00 mL). PdCl$_2$(dppf).CH$_2$Cl$_2$ adduct (4.5 mg, 5.6 µmol) was then added and the reaction mixture was stirred for 16 h at 85° C. The reaction mixture was cooled to room temperature and was diluted with water (10 mL). The aqueous layer was extracted with ethyl acetate (3×10 mL). The combined organic layers were dried (sodium sulfate) and concentrated under vacuum. The product was purified by column chromatography on silica gel (0%->50% ethyl acetate in hexanes) to afford methyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)butanoate (53 mg, 0.079 mmol, 71% yield). LC/MS: m/e 671.5 (M+H)$^+$, 2.36 min (method 3).

Step 2

To a solution of methyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)butanoate (53 mg, 0.079 mmol) in 1,4-dioxane (2 mL) and ethanol (1 mL) was added NaOH (1 N) (0.395 mL, 0.395 mmol). The reaction mixture was heated for 16 h at 100° C. The mixture was cooled to room temperature and was concentrated. The residue was taken up in methanol and dioxane and was purified by prep HPLC (Method 9, t$_R$=6.14) to give the TFA salt of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)butanoic acid (18.7 mg, 25% yield) as a white solid. LC/MS m/e 657.4 (M+H)$^+$, 2.22 min (ionization peak, no UV) (method 3). $^1$H NMR (400 MHz, CHLOROFORM-d) δ 5.24 (d, J=5.3 Hz, 1H), 4.80 (s, 1H), 4.71 (s, 1H), 3.47-3.39 (m, J=12.0 Hz, 1H), 3.25-3.01 (m, 9H), 2.95-2.84 (m, 3H), 2.42-2.31 (m, 2H), 2.28-0.81 (m, 26H), 1.71 (s, 3H), 1.18 (s, 3H), 1.06 (s, 3H), 0.99 (s, 3H), 0.93 (s, 3H), 0.83 (s, 3H).

Example 12

5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-N-hydroxy-3,3-dimethylpentanamide

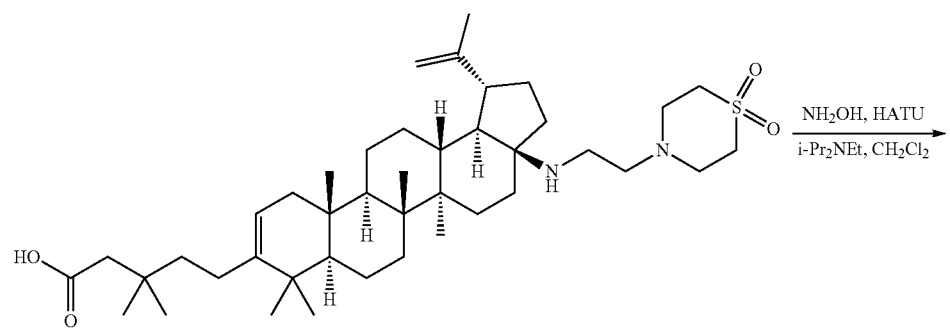

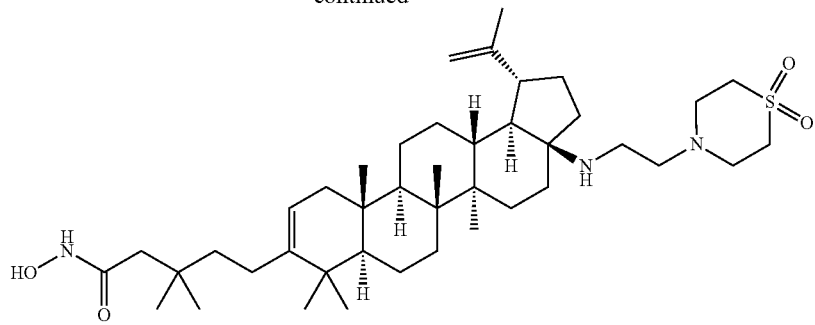

A solution of 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoic acid (35 mg, 0.050 mmol) in DCM (2 mL) was treated with HATU (28.6 mg, 0.075 mmol), N,N-diisopropylethylamine (0.026 mL, 0.150 mmol), and hydroxylamine (1.8 mg, 0.055 mmol). The reaction mixture was stirred at rt for 16 h. The mixture was concentrated and the crude product was purified by prep HPLC (Method 10) to afford 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-N-hydroxy-3,3-dimethylpentanamide (1.9 mg, 5% yield). LC/MS m/e 714.5 (M+H)$^+$, 2.23 min (ionization peak, no UV) (method 3). $^1$H NMR (500 MHz, DMSO-d$_6$) δ 10.29 (2, 1H), 5.20 (d, J=5.5 Hz, 1H), 4.69 (s, 1H), 4.55 (s, 1H), 3.14-3.01 (m, 4H), 2.98-2.84 (m, 4H), 2.65-2.55 (m, 3H), 2.50-2.44 (m, J=5.9 Hz, 1H), 2.40-2.31 (m, J=5.1 Hz, 1H), 1.97-0.76 (m, 28H), 1.65 (s, 3H), 1.03 (s, 3H), 0.95 (s, 3H), 0.94 (s, 9H), 0.87 (s, 3H), 0.79 (s, 3H).

Example 13

5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-N-methoxy-3,3-dimethylpentanamide

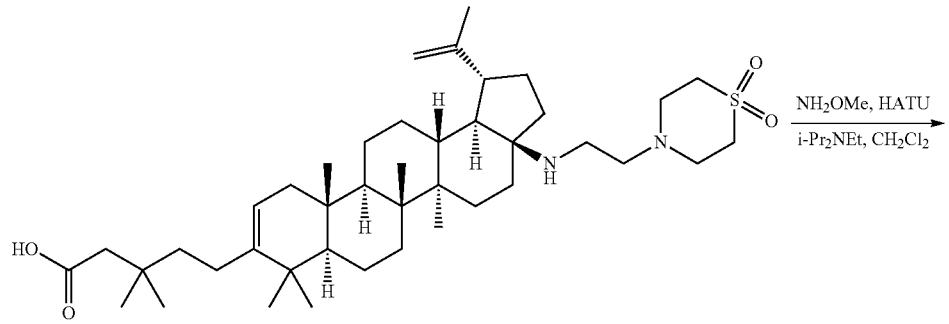

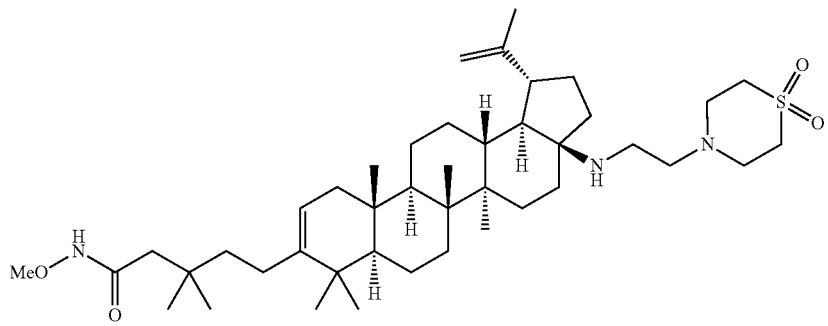

A solution of 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoic acid (30 mg, 0.043 mmol) in DCM (2 mL) was treated with HATU (24.5 mg, 0.064 mmol), N,N-diisopropylethylamine (0.022 mL, 0.129 mmol), and O-methylhydroxylamine, HCl (3.9 mg, 0.047 mmol). The reaction mixture was stirred at rt for 16 h. The mixture was concentrated and the crude product was purified by prep HPLC (Method 11) to afford 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-N-methoxy-3,3-dimethylpentanamide (5.4 mg, 17% yield). LC/MS m/e 728.5 (M+H)$^+$, 2.26 min (ionization peak, no UV) (method 3). $^1$H NMR (500 MHz, DMSO-d$_6$) δ 10.89 (s, 1H), 5.20 (d, J=5.9 Hz, 1H), 4.69 (s, 1H), 4.55 (s, 1H), 3.56 (s, 3H), 3.12-3.02 (m, 4H), 2.99-2.87 (m, 4H), 2.64-2.55 (m, 3H), 2.49-2.45 (m, 1H), 2.40-2.33 (m, 1H), 1.96-0.76 (m, 28H), 1.65 (s, 3H), 1.03 (s, 3H), 0.95 (s, 3H), 0.94 (s, 6H), 0.93 (s, 3H), 0.87 (s, 3H), 0.78 (s, 3H).

Example 14

N-cyano-5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanamide A solution of 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoic acid (30 mg, 0.043 mmol) in DMF (1 mL) was treated with EDC (11.7 mg, 0.061 mmol) and HOBT (8.2 mg, 0.053 mmol). The reaction mixture was stirred at rt for 1 h. N,N-diisopropylethylamine (0.013 mL, 0.073 mmol) was added to the reaction mixture and after stirring 10 min, cyanamide (1.0 mg, 0.024 mmol) was then added. The reaction mixture was stirred at room temperature for 16 h. The mixture was concentrated and the crude product was purified by prep HPLC (Method 12) to afford N-cyano-5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanamide (4.9 mg, 28% yield). LC/MS m/e 723.5 (M+H)$^+$, 2.29 min (method 3). $^1$H NMR (500 MHz, DMSO-d$_6$) δ 5.19 (d, J=5.9 Hz, 1H), 4.71 (s, 1H), 4.58 (s, 1H), 3.49 (t, J=4.8 Hz, 1H), 3.42 (t, J=5.5 Hz, 1H), 3.14-3.03 (m, 4H), 3.01-2.92 (m, 4H), 2.72-2.58 (m, 3H), 1.96-0.76 (m, 28H), 1.66 (s, 3H), 1.04 (s, 3H), 0.95 (s, 6H), 0.92 (s, 6H), 0.87 (s, 3H), 0.79 (s, 3H)

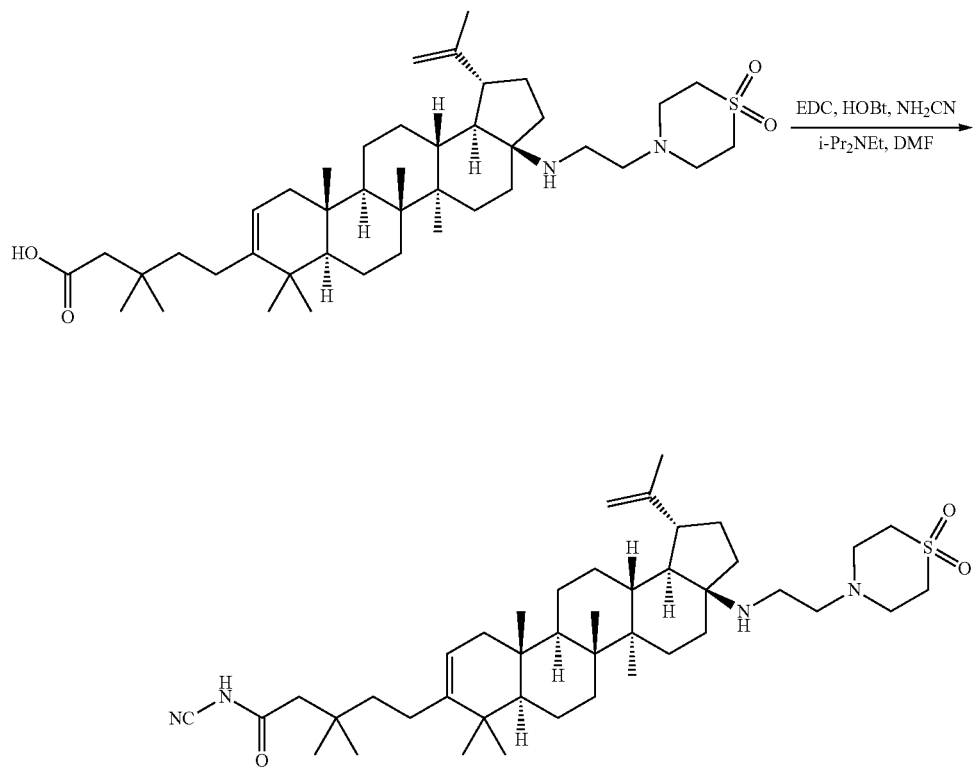

Example 15

5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethyl-N-(methylsulfonyl)pentanamide

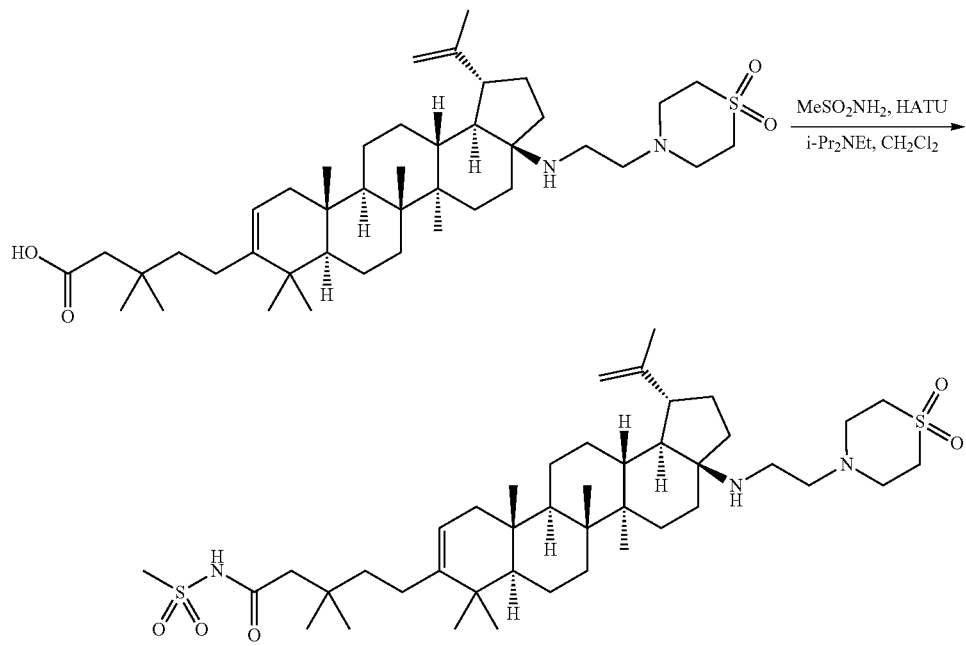

A solution of 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoic acid (30 mg, 0.043 mmol) in DCM (2 mL) was treated with HATU (28.6 mg, 0.075 mmol), N,N-diisopropylethylamine (0.026 mL, 0.150 mmol), and methanesulfonamide (5.3 mg, 0.055 mmol). The reaction mixture was stirred at rt for 16 h. The mixture was concentrated and the crude product was purified by prep HPLC (Method 13) to afford 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethyl-N-(methylsulfonyl)pentanamide (9.1 mg, 23% yield). LC/MS m/e 776.5 (M+H)$^+$, 2.34 min (ionization peak, no UV) (method 3). $^1$H NMR (500 MHz, DMSO-d$_6$) δ 5.20 (d, J=5.1 Hz, 1H), 4.69 (s, 1H), 4.55 (br. s., 1H), 3.08 (br. s., 1H), 3.00-2.91 (m, 3H), 2.81 (d, J=2.6 Hz, 3H), 2.74 (s, 3H), 2.64-2.56 (m, 3H), 2.48 (d, J=5.5 Hz, 1H), 2.40-2.32 (m, 1H), 1.95-0.76 (m, 29H), 1.91 (s, 3H), 1.65 (s, 3H), 1.03 (s, 3H), 0.95 (s, 3H), 0.94 (s, 6H), 0.93 (s, 3H), 0.87 (s, 3H), 0.78 (s, 3H).

Example 16

Preparation of 5-((1S,3aS,5aR,5bR,7aS,11aS,11bR,13aR,13bR)-3a-((2-(1,1-dioxidothiomorpholino)ethyl)amino)-1-isopropyl-5a,5b,8,8,11a-pentamethylicosahydro-1H-cyclopenta[a]chrysen-9-yl)pentanoic acid

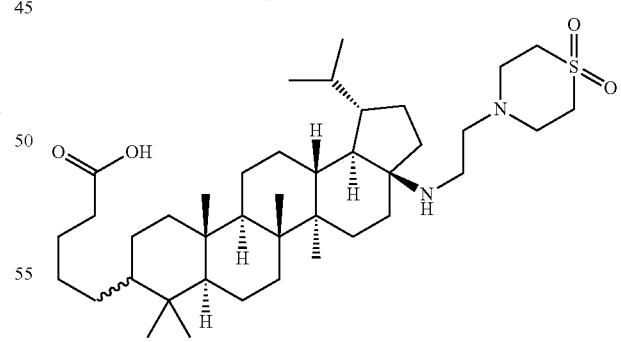

A solution of 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)pentanoic acid (0.031 g, 0.046 mmol) in ethanol (3 mL) and 1,4-dioxane (2 mL) was hydrogenated using the H-Cube system set to 50 bar of hydrogen and 50° C. The reaction was set up as a continuous loop and was monitored by LC/MS. After 7 h, the sample was removed and concentrated under reduced pressure. It was again diluted with ethanol and 1,4-dioxane and run on continuous loop on the H-Cube at 50 bar and 50° C. for an additional 4 h. The mixture was removed and was concentrated under reduced pressure, then was dissolved in 1,4-dioxane and ethanol and was purified by prep HPLC (method 8, retention time=10.6 minutes) to give the TFA salt of the title product (11.8 mg, 0.0149 mmol, 32%) as a white solid. LCMS: m/e: 675.4 (M+H)$^+$, 1.81 min (ionization peak, no UV) (method 3). $^1$H NMR (500 MHz, Acetic) δ=3.45-3.38 (m, 1H), 3.32-3.01 (m, 11H), 2.44-2.32 (m, 2H), 1.21 (s, 3H), 1.07 (s, 3H), 2.19-0.73 (m, 45H), 0.70 (s, 3H).

Example 17

Preparation of 5-((1S,3aS,5aR,5bR,7aS,11aS,11bR, 13aR,13bR)-3a-((2-(1,1-dioxidothiomorpholino) ethyl)amino)-1-isopropyl-5a,5b,8,8,11a-pentamethylicosahydro-1H-cyclopenta[a]chrysen-9-yl)-2,2-dimethylpentanoic acid A solution of 5-((1R,3aS,5aR,5bR,7aR,11aS,11bR,13aR, 13bR)-3a-((2-(1,1-dioxidothiomorpholino)ethyl)amino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-2,2-dimethylpentanoic acid (0.021 g, 0.030 mmol) in ethanol (3 mL) and 1,4-dioxane (2 mL) was hydrogenated using the H-Cube system set to 50 bar of hydrogen and 50° C. The reaction was set up as a continuous loop and was monitored by LC/MS. After 7 h, the sample was removed. LC/MS showed the reaction was not complete, so the mixture was again run on the H-Cube system using the continuous loop, 50 bar of hydrogen and 50° C. After 6 h, the mixture was removed from the H-Cube, concentrated under reduced pressure, then dissolved in 1,4-dioxane and methanol and purified by prep HPLC (method 8, retention time=12.4 minutes to give the TFA salt of the title product (0.008 g, 0.0097 mmol, 32%) as a white solid. LCMS: m/e: 703.7 (M+H)$^+$, 1.95 min (ionization peak, no UV) (method 3). $^1$H NMR (500 MHz, Acetic acid-d$_4$) δ=3.45-3.39 (m, 1H), 3.33-3.04 (m, 11H), 1.07 (s, 3H), 2.20-0.72 (m, 54H), 0.69 (s, 3H).

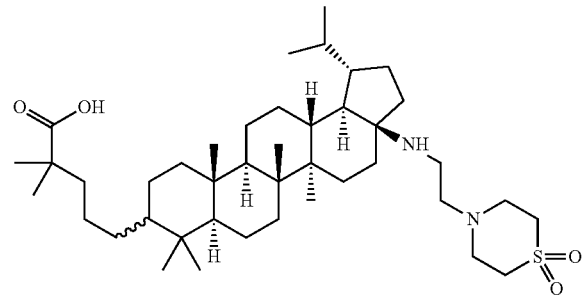

Example 18

Preparation of 3,3-dimethyl-5-((1R,3aS,5aR,5bR, 7aR,11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)pentanoic acid

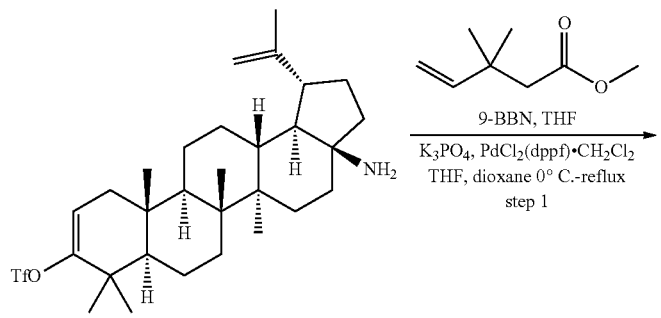

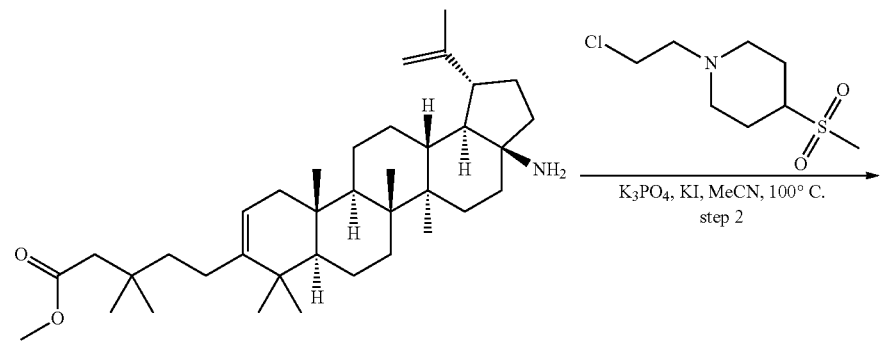

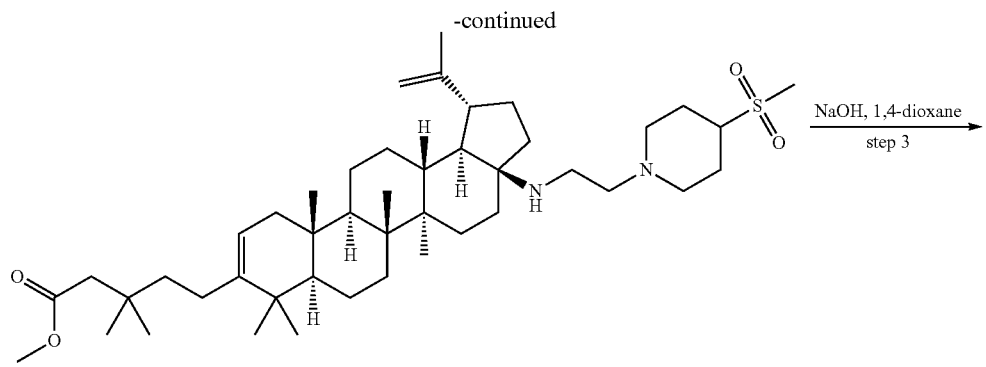

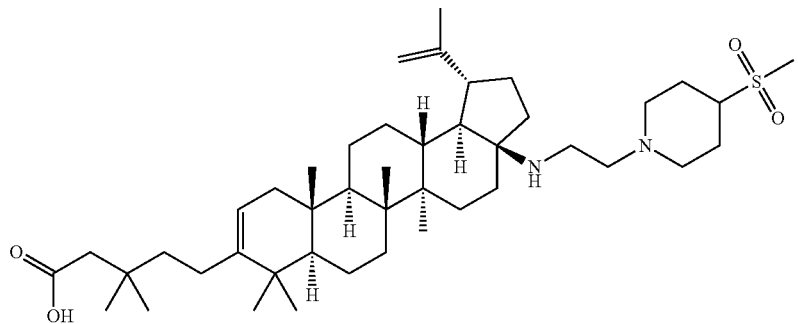

Example 18

Step 1. Preparation of methyl 5-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-3,3-dimethylpentanoate

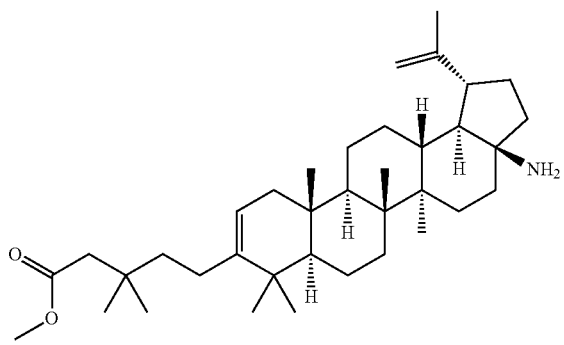

A solution of 4-pentenoic acid, 3,3-dimethyl-, methyl ester (1.275 mL, 8.07 mmol) in THF (20 mL) was cooled to 0° C. and 9-BBN (0.5M in THF) (17.21 mL, 8.61 mmol) was added dropwise. The mixture was removed from the ice bath and was stirred at rt for 2 h. To the solution was added a solution of phosphoric acid, potassium salt (1M) (6.72 mL, 13.45 mmol) followed by a solution of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (3 g, 5.38 mmol) in 1,4-dioxane (20 mL) and finally 1,1'-bis(diphenylphosphino)ferrocenepalladium(II) dichloride, toluene (0.221 g, 0.269 mmol). The mixture was heated to reflux for 15 h then cooled at rt, diluted with water (100 mL), and extracted with ethyl acetate (3×100 mL). The organic layers were washed with brine, dried over magnesium sulfate, filtered, and concentrated under reduced pressure. The filtrate was purified by flash chromatography using a 5-65% ethyl acetate in hexanes gradient and a 120 g silica gel column. The fractions containing the product were combined and concentrated under reduced pressure to give the title compound (2.33 g, 4.22 mmol, 78% yield) as a yellow foam. $^1$H NMR (400 MHz, CHLOROFORM-d) δ=5.24 (d, J=5.5 Hz, 1H), 4.73 (d, J=1.8 Hz, 1H), 4.60 (s, 1H), 3.65 (s, 3H), 2.55 (td, J=10.9, 5.1 Hz, 1H), 2.23 (s, 2H), 1.70 (s, 3H), 1.07 (s, 3H), 1.02 (s, 6H), 0.98 (s, 3H), 0.96 (s, 3H), 0.89 (s, 3H), 0.83 (s, 3H), 2.12-0.79 (m, 28H).

Step 2. Preparation of methyl 3,3-dimethyl-5-((1R, 3aS,5aR,5bR,7aR,11aS,11bR,13aR,13bR)-5a,5b,8,8, 11a-pentamethyl-3a-((2-(4-(methylsulfonyl)piperidin-1-yl)ethyl)amino)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) pentanoate

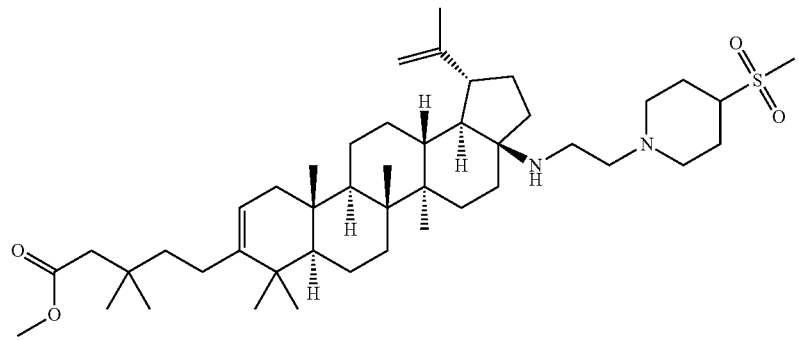

To a flask containing methyl 5-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)-3,3-dimethylpentanoate (0.06 g, 0.109 mmol) was added phosphoric acid, potassium salt (0.115 g, 0.544 mmol), potassium iodide (0.020 g, 0.120 mmol), and 1-(2-chloroethyl)-4-(methylsulfonyl)piperidine, HCl (prepared as described in WO2012106190 (0.057 g, 0.217 mmol). The mixture was diluted with acetonitrile (3 mL), flushed with nitrogen, and heated to reflux for 3 h. The mixture was cooled to rt, diluted with water (15 mL), and extracted with ethyl acetate (3×15 mL). The organic layers were washed with brine, dried over magnesium sulfate, filtered, and concentrated under reduced pressure. The residue was purified by flash chromatography using a 5-85% ethyl acetate in hexanes gradient and a 12 g silica gel column to give the title product (0.043 g, 0.058 mmol, 53.4% yield) as a light-yellow foam. LCMS: m/e: 741.6 (M+H)$^+$, 2.04 min (method 3).

Step 3

To a solution of methyl 3,3-dimethyl-5-((1R,3aS,5aR,5bR, 7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) pentanoate (0.04 g, 0.054 mmol) in 1,4-dioxane (1 mL) was added sodium hydroxide (20% wt.) (0.216 g, 1.079 mmol). The mixture was heated to 85° C. for 63 h then was cooled to rt and was purified by prep HPLC. The fractions containing the expected product were combined and concentrated under reduced pressure to give the TFA salt of the title product (19.4 mg, 0.023 mmol, 43% yield) as a white solid. LCMS: m/e: 727.7 (M+H)$^+$, 1.85 min (method 1). $^1$H NMR (500 MHz, Acetic acid-d$_4$) δ=5.28 (d, J=5.5 Hz, 1H), 4.83 (s, 1H), 4.72 (s, 1H), 3.89-3.66 (m, 6H), 3.45-3.37 (m, 1H), 3.30-3.19 (m, 2H), 2.99 (s, 3H), 2.82-2.74 (m, 1H), 2.46-2.37 (m, 2H), 2.29 (s, 2H), 1.73 (s, 3H), 1.12 (s, 3H), 1.07 (s, 3H), 1.06 (s, 6H), 1.02 (s, 3H), 0.94 (s, 3H), 0.88 (s, 3H), 2.24-0.84 (m, 28H).

Example 19

Preparation of (1R,3aS,5aR,5bR,7aR,11aS,13aR, 13bR)-9-(2-carboxyethyl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysene-3a-carboxylic acid

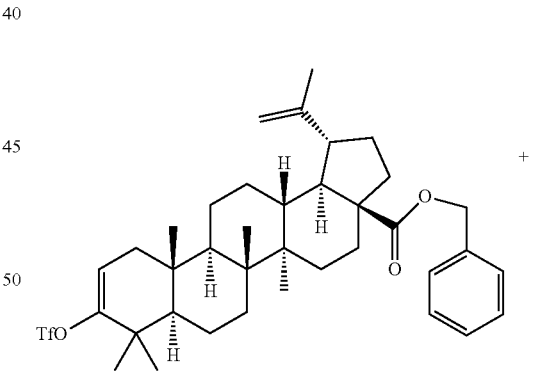

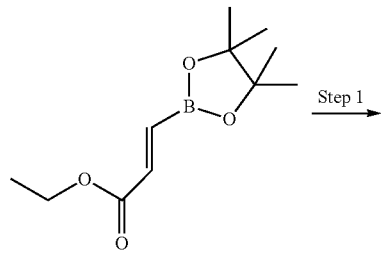

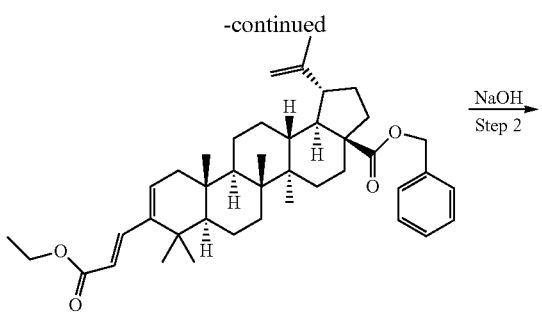

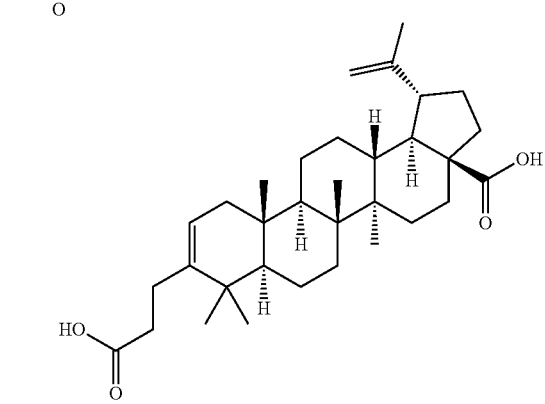

Example 19

Step 1. Preparation of (1R,3aS,5aR,5bR,7aR,11aS, 13aR,13bR)-benzyl 9-((E)-3-ethoxy-3-oxoprop-1-enyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate

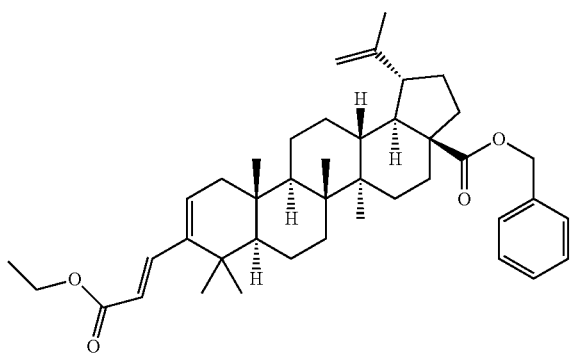

A mixture of (1R,3aS,5aR,5bR,7aR,11aR,13aR,13bR)-benzyl 5a,5b,8,8,11a-pentamethyl-1-(prop-1-en-2-yl)-9-(trifluoromethylsulfonyloxy)-2,3,3a,4,5,5a,5b,6,7,7a,8,11,11a, 11b,12,13,13a,13b-octadecahydro-1H-cyclopenta[a] chrysene-3a-carboxylate, prepared as described in WO2011153315, (50 mg, 0.074 mmol), (E)-ethyl 3-(4,4,5,5-tetramethyl-1,3,2-dioxaborolan-2-yl)acrylate (66.8 mg, 0.295 mmol), tetrakis(triphenylphosphine)palladium (8.54 mg, 0.0074 mmol) and sodium carbonate (39 mg, 0.369 mmol) in DME (1 mL) and water (1 mL) was heated to 100° C. for 1.5 hours. The reaction mixture was cooled to rt, extracted with ethyl acetate (3×5 mL). The extracts were combined, dried over sodium sulfate, filtered and concentrated under reduced pressure. The crude residue was purified by flash chromatography with 80-100% ethyl acetate/hexanes gradient to provide the title compound (20 mg, 43%). LCMS: m/e 627.55 (M+H)$^+$, 3.60 min (method 6).

Step 2. Preparation of (E)-3-((1R,3aS,5aR,5bR,7aR, 11aS,13aR,13bR)-3a-(benzyloxycarbonyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)acrylic acid

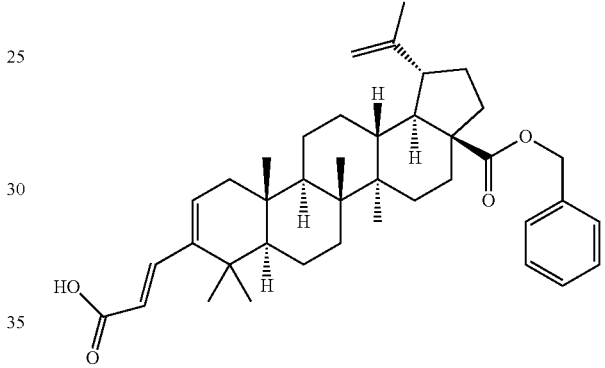

A mixture of (1R,3aS,5aR,5bR,7aR,11aS,13aR,13bR)-benzyl 9-((E)-3-ethoxy-3-oxoprop-1-enyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysene-3a-carboxylate (20 mg, 0.032 mmol) and 10 N sodium hydroxide (0.032 mL, 0.319 mmol) in dioxane (0.5 mL) and water (0.5 mL) was heated at 100° C. for 3 hours. The reaction mixture was neutralized with 1N HCl to pH=6 and extracted with ethyl acetate (3×4 mL). The extracts were combined, dried over sodium sulfate, filtered and concentrated under reduced pressure to provide the title compound (20 mg, 105%). This material was used in the next step without further purification. LCMS: m/e 597.68 (M–H)$^-$, 2.50 min (method 6).

Step 3

A mixture of (E)-3-((1R,3aS,5aR,5bR,7aR,11aS,13aR, 13bR)-3a-(benzyloxycarbonyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) acrylic acid (20 mg, 0.033 mmol) and 10% Pd/C (25 mg, 0.023 mmol) in MeOH (0.5 mL) and ethyl acetate (1 mL) was connected to a balloon of hydrogen and stirred at room temperature for 5 hours. The reaction mixture was filtered to remove Pd/C and the filtrates were concentrated under reduced pressure. The residue was dissolved in DMF and purified by prep HPLC to provide the desired product (1.59 mg, 9%). LCMS: m/e 509.6 (M–H)$^-$, 2.36 min (method 6). $^1$H NMR (400 MHz, <DMSOmix>) δ 5.21 (d, J=5.0 Hz, 1H), 4.70 (br. s., 1H), 4.57 (br. s., 1H), 3.05-0.98 (m, 27H), 1.67 (s., 3H), 0.96 (s., 6H), 0.93 (s., 3H), 0.89 (s., 3H), 0.79 (s., 3H).

Example A1
Preparation of 4-((((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclohexanecarboxylic acid, TFA
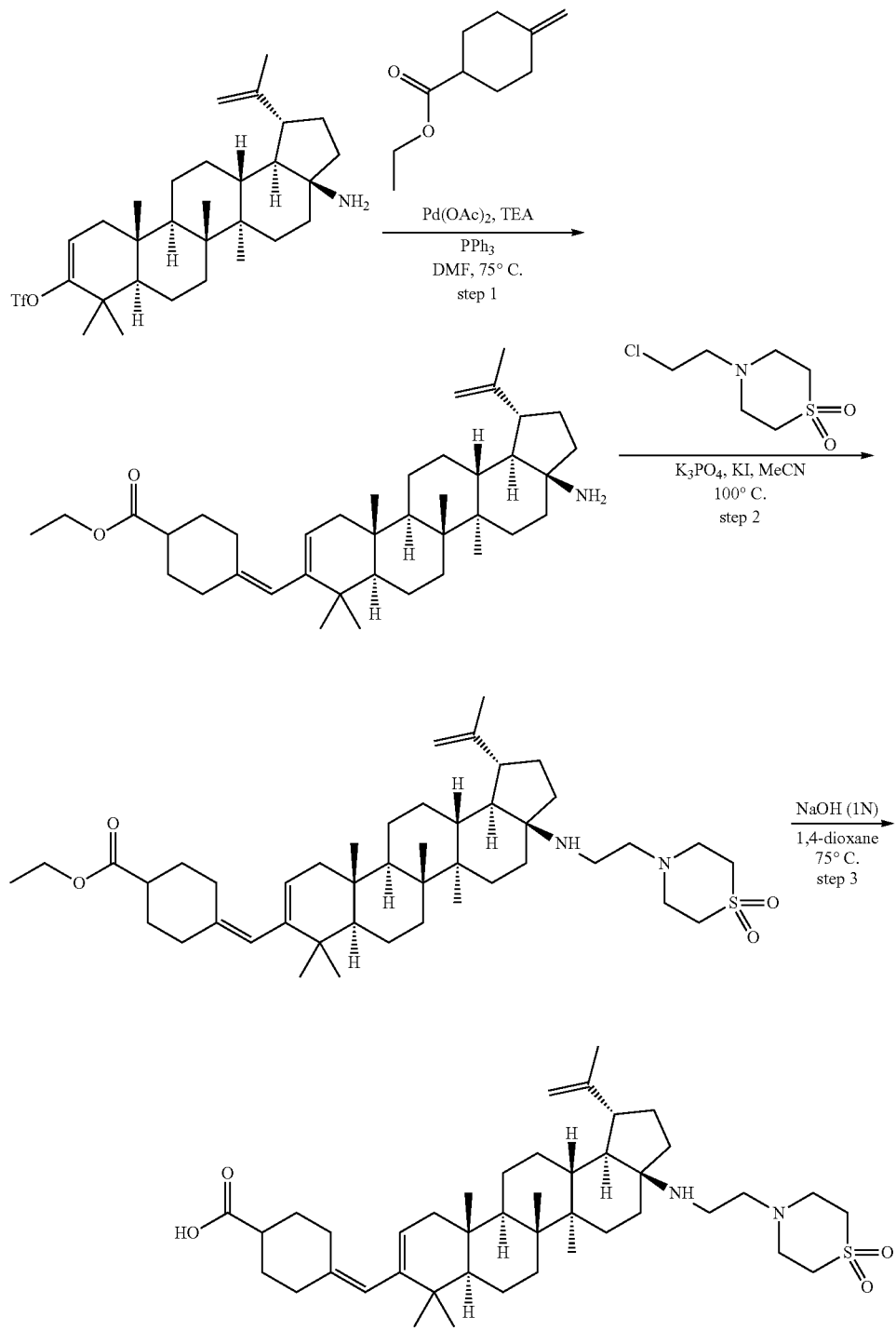
Example A1

Step 1: Preparation of ethyl 4-(((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclohexanecarboxylate

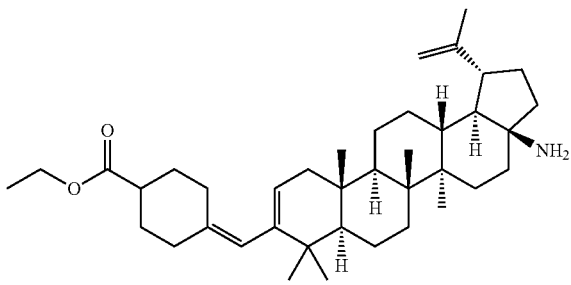

To a vial containing ethyl 4-methylenecyclohexanecarboxylate (0.030 g, 0.179 mmol) was added (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate (0.05 g, 0.090 mmol), triphenylphosphine (2.351 mg, 8.96 µmol), and palladium(II) acetate (1.006 mg, 4.48 µmol). The mixture was diluted with DMF (1 mL) and TEA (0.037 mL, 0.269 mmol) was added. The vial was flushed with nitrogen, then was sealed and heated to 75° C. for 21 h. The mixture was cooled to rt, diluted with water (3 mL), and extracted with dichloromethane (4×3 mL). The organic layers were dried over sodium sulfate, filtered, and concentrated under reduced pressure. The residue was purified by flash chromatography using a 0-75% ethyl acetate in hexanes gradient and a 12 g silica gel column to give the title compound (0.015 g, 0.026 mmol, 29.1% yield) as a clear film. LCMS: m/e: 576 (M+H)$^+$, 2.26 min (method 1).

Step 2: Preparation of ethyl 4-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclohexanecarboxylate To a sealable flask containing ethyl 4-(((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclohexanecarboxylate (0.015 g, 0.026 mmol) was added phosphoric acid, potassium salt (0.028 g, 0.130 mmol), potassium iodide (0.013 g, 0.078 mmol) and 4-(2-chloroethyl)thiomorpholine 1,1-dioxide (0.015 g, 0.078 mmol). The mixture was diluted with acetonitrile (1 mL), flushed with nitrogen, sealed, and heated to 100° C. After heating the mixture for 22 h, it was cooled to rt, diluted with water (5 mL), and extracted with dichloromethane (3×5 mL). The organic layers were dried with sodium sulfate, filtered, and concentrated under reduced pressure. The crude product was used in the next step with no additional purification. LCMS: m/e: 737.7 (M+H)$^1$, 2.22 min (method 1).

Step 3

To a solution of ethyl 4-(((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclohexanecarboxylate (19.2 mg, 0.026 mmol) in 1,4-dioxane (2 mL) was added NaOH (1N) (0.130 mL, 0.130 mmol). The mixture was warmed to 75° C. for 15 h then was cooled to rt. LC/MS showed the reaction was progressing, but some starting material still remained. An additional 0.05 mL of 1N NaOH was added and the mixture was heated to 75° C., then was cooled to rt, diluted with methanol and dioxane, and purified by prep HPLC (method 5) to give the title compound (1.0 mg, 0.0012 mmol, 4.6% yield. $^1$H NMR (400 MHz, acetic acid-d$_4$) δ=5.85 (br. s., 1H), 5.20 (d, J=6.0 Hz, 1H), 4.83 (s, 1H), 4.72 (s, 1H), 3.49-3.44 (m, 1H), 3.38-3.05 (m, 11H), 3.00-2.91 (m, 1H), 2.83-2.74 (m, 1H), 2.62-2.51 (m, 1H), 1.74 (s, 3H), 1.25 (s, 3H), 1.10 (s, 3H), 1.02 (s, 3H), 0.98 (s, 3H), 0.93 (s, 3H), 2.39-0.85 (m, 29H).

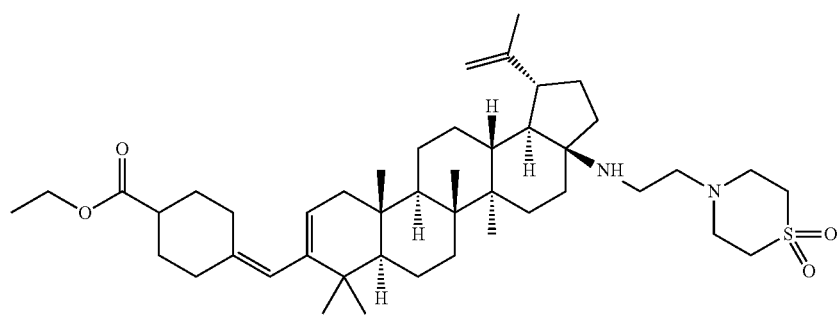

Example B1
Preparation of 4-((E)-2-((1R,3aS,5aR,5bR,7aR,11aS, 11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)vinyl)benzoic acid
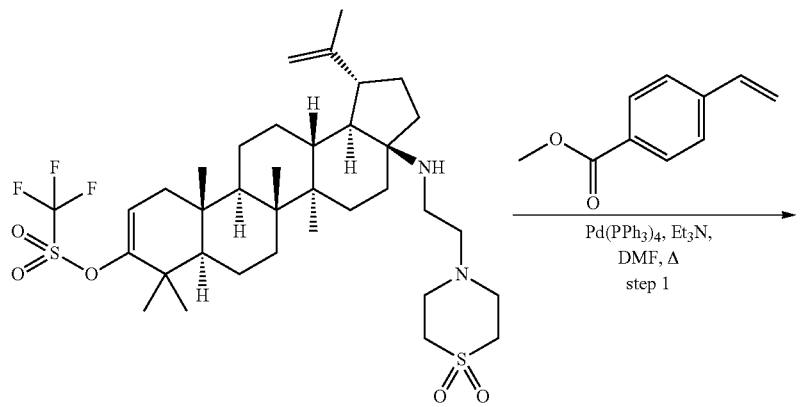
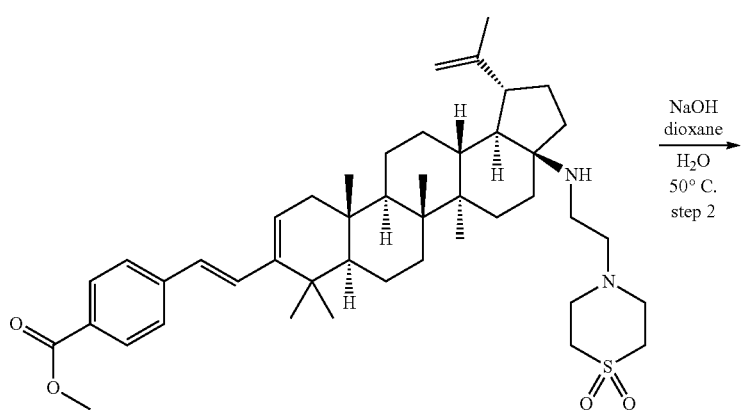
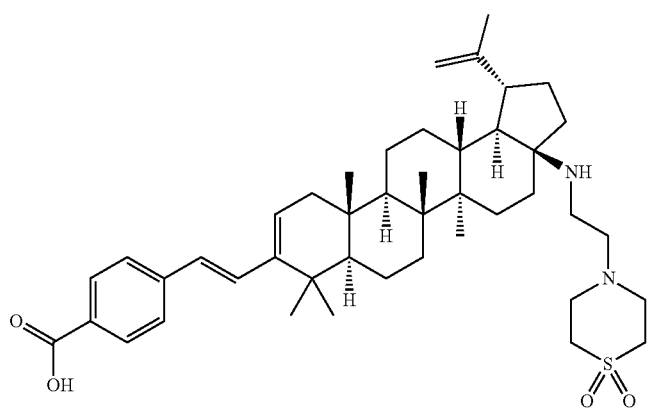
Example B1

Step 1. Preparation of methyl 4-((E)-2-((1R,3aS,5aR, 5bR,7aR,11aS,11bR,13aR,13bR)-3a-((2-(1,1-dioxi-dothiomorpholino)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)vinyl)benzoate

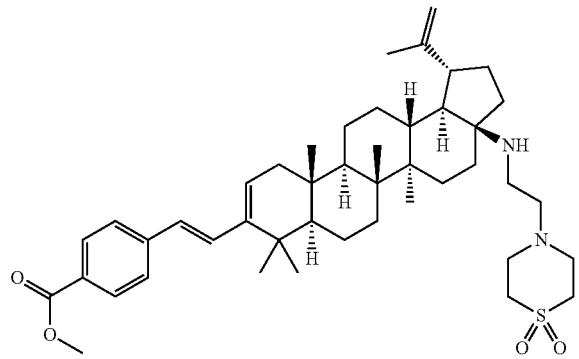

To a suspension of (1R,3aS,5aR,5bR,7aR,11aR,11bR, 13aR,13bR)-3a-((2-(1,1-dioxidothiomorpholino)ethyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yltrifluoromethanesulfonate (60 mg, 0.083 mmol), methyl 4-vinylbenzoate (27.1 mg, 0.167 mmol) and Pd(PPh$_3$)$_4$ (1.929 mg, 1.669 µmol) in DMF (0.5 mL) was added triethylamine (0.035 mL, 0.250 mmol). The mixture was chilled to −78° C., evacuation/purging cycles were performed three times followed by an N$_2$ purge. The flask was immersed into an oil bath at 75° C. Upon heating, the reaction mixture turned black. After heating the mixture for 2 h, the mixture was cooled to rt, diluted with ethyl acetate (50 mL) and washed with water (10 mL). The organic layer was collected and dried over sodium sulfate. After removal of solvents, the brown oil residue was purified by flash chromatography using a 0-45% EtOAc in hexanes gradient and a 12 g silica gel column to give the title compound as a white solid (35 mg, 57.4% yield). LCMS: m/e 731.6 (M+H)$^+$, 3.057 min (method 4). $^1$H NMR (400 MHz, CHLOROFORM-d) δ 7.98 (d, J=8.3 Hz, 2H), 7.57-7.53 (m, 2H), 6.93 (d, J=15.8 Hz, 1H), 6.73 (d, J=15.8 Hz, 1H), 5.91 (d, J=4.8 Hz, 1H), 4.75 (d, J=2.0 Hz, 1H), 4.63 (br. s., 1H), 3.93-3.90 (m, 3H), 3.15-3.02 (m, 8H), 2.84-2.50 (m, 5H), 2.15 (dd, J=17.7, 6.7 Hz, 1H), 2.02-1.73 (m, 5H), 1.71 (s, 3H), 1.66-1.21 (m, 16H), 1.13 (s, 3H), 1.08 (br. s., 3H), 1.03 (s, 3H), 1.00 (s, 3H), 0.90-0.87 (m, 3H).

Step 2

To a solution of methyl 4-((E)-2-((1R,3aS,5aR,5bR,7aR, 11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)vinyl) benzoate (35 mg, 0.048 mmol) in dioxane (2 mL) and MeOH (1 mL) was added 1N NaOH (1 mL, 1 mmol). The mixture was stirred at 50° C. for 2 h. The crude product was purified by prep HPLC (method 4) to give 4-((E)-2-((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) vinyl)benzoic acid as a white solid (12 mg, 35.0%). MS: m/e 717.5 (M+H)$^+$, 2.798 min (method 4). $^1$H NMR (400 MHz, CHLOROFORM-d) δ 8.08-7.95 (m, 2H), 7.47 (br. s., 2H), 6.98-6.83 (m, 1H), 6.77-6.64 (m, 1H), 5.87 (d, J=4.8 Hz, 1H), 4.72 (br. s., 1H), 4.61 (br. s., 1H), 3.27-3.06 (m, 8H), 2.95 (d, J=7.3 Hz, 2H), 2.86-2.62 (m, 3H), 2.23-2.00 (m, 3H), 1.98-1.79 (m, 4H), 1.73 (br. s., 3H), 1.66-1.50 (m, 5H), 1.48-1.18 (m, 10H), 1.11 (s, 3H), 1.09-1.05 (m, 3H), 1.03-0.96 (m, 6H), 0.76 (s, 3H).

Example B2

Preparation of 1-((tert-butoxycarbonyl)amino)-2-((E)-2-((1R,3aS,5aR,5bR,7aR,11aS,11bR,13aR, 13bR)-3a-((2-(1,1-dioxidothiomorpholino)ethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) vinyl)cyclopropanecarboxylic acid

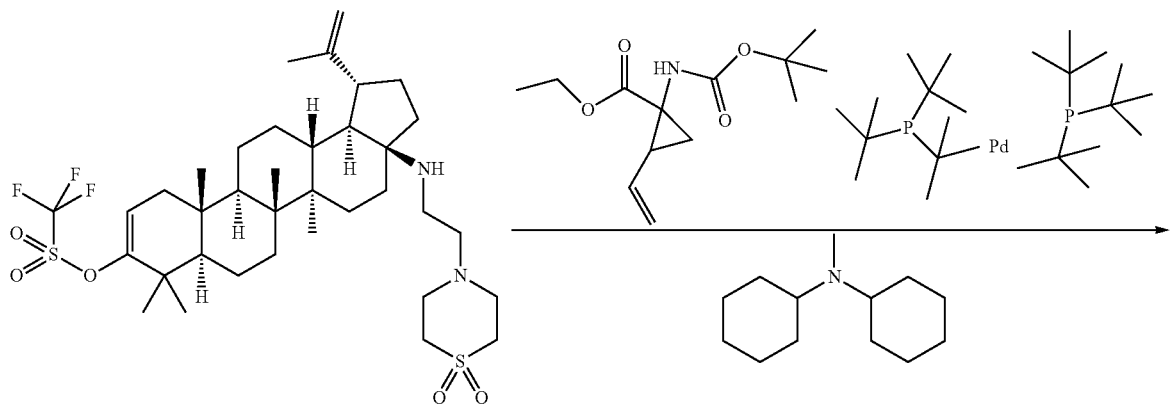

-continued

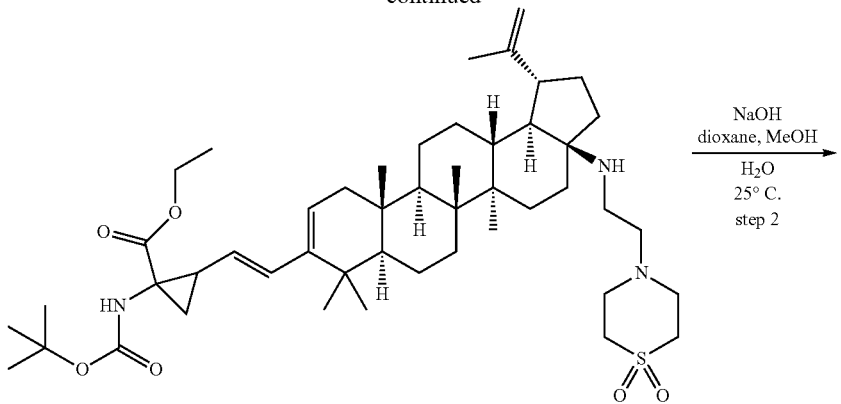

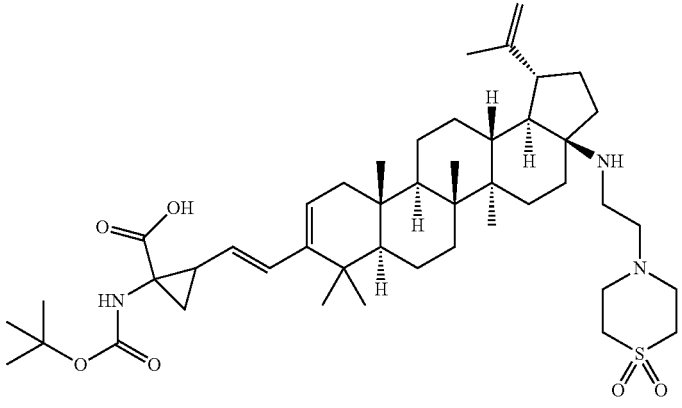

Example B2

Step 1. Preparation of ethyl 1-((tert-butoxycarbonyl) amino)-2-((E)-2-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)vinyl)cyclopropanecarboxylate

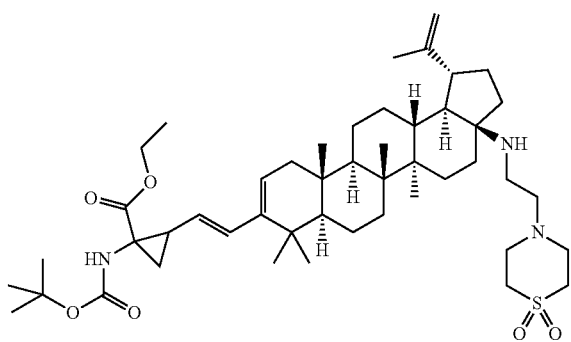

The mixture of (1R,3aS,5aR,5bR,7aR,11aR,11bR,13aR, 13bR)-3a-((2-(1,1-dioxidothiomorpholino)ethyl)amino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl trifluoromethanesulfonate (50 mg, 0.070 mmol), ethyl 1-((tert-butoxycarbonyl)amino)-2-vinylcyclopropanecarboxylate (17.76 mg, 0.070 mmol) and N-cyclohexyl-N-methylcyclohexanamine (0.018 mL, 0.083 mmol) in dioxane (1 mL) was placed in a sealable pressure tube and $N_2$ was bubbled through the solution for 10 min. Bis(tri-tertbutylphosphine) Palladium(0) (0.355 mg, 0.695 μmol) was added to the reaction mixture and the tube was sealed, and heated to 110° C. for 4 h. After cooling to rt, the crude reaction mixture was diluted with diethyl ether and filtered. The filtrate was concentrated and purified using a flash silica gel column (4 g; eluted with ethyl acetate in hexane from 0 to 45%) to give the title compound as a yellow film (13 mg, 22.7%). MS: m/e 824.55 (M+H)+, 2.625 min (method 4). $^1$H NMR (400 MHz, CHLOROFORM-d) δ 7.23-5.36 (m, 2H), 5.27-5.12 (m, 1H), 4.72 (br. s., 1H), 4.61 (br. s., 1H), 4.26 (m, 2H), 3.24-2.92 (m, 8H), 2.72-2.45 (m, 5H), 2.32-1.76 (m, 11H), 1.68 (br. s., 3H), 1.53-0.74 (m, 42H).

Step 2

To a solution of ethyl 1-((tert-butoxycarbonyl)amino)-2-((E)-2-((1R,3aS,5aR,5bR,7aR,11aS,11bR,13aR,13bR)-3a-((2-(1,1-dioxidothiomorpholino)ethyl)amino)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)vinyl)cyclopropanecarboxylate (12 mg, 0.015 mmol) in dioxane (2 mL) and MeOH (1 mL) was added 1N NaOH (1 mL, 1 mmol). The mixture was stirred at 25° C. for 2 h. The crude product was purified by prep HPLC (method 4) to give 1-((tert-butoxycarbonyl) amino)-2-((E)-2-((1R,3aS,5aR,5bR,7aR,11aS,11bR,13aR, 13bR)-3a-((2-(1,1-dioxidothiomorpholino)ethyl)amino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)vinyl)cyclopropanecarboxylic acid as a white solid (1 mg, 8.63%). MS: m/e 796.55 (M+H)+, 2.57 min (method 2). $^1$H NMR (400 MHz, METHANOL-$d_4$) δ 7.37-5.41 (m, 2H), 5.36-5.10 (m, 1H), 4.73 (br. s., 1H), 4.57 (br. s., 1H), 3.19-2.97 (m, 8H), 2.80-2.62 (m, 4H), 2.58-2.41 (m, 1H), 2.36-1.78 (m, 7H), 1.72 (s, 3H), 1.69-1.21 (m, 25H), 1.16 (m, 6H), 1.09-1.00 (m, 6H), 0.98-0.82 (m, 6H).

Example B3
Preparation of 1-fluoro-4-((((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclohexanecarboxylic acid
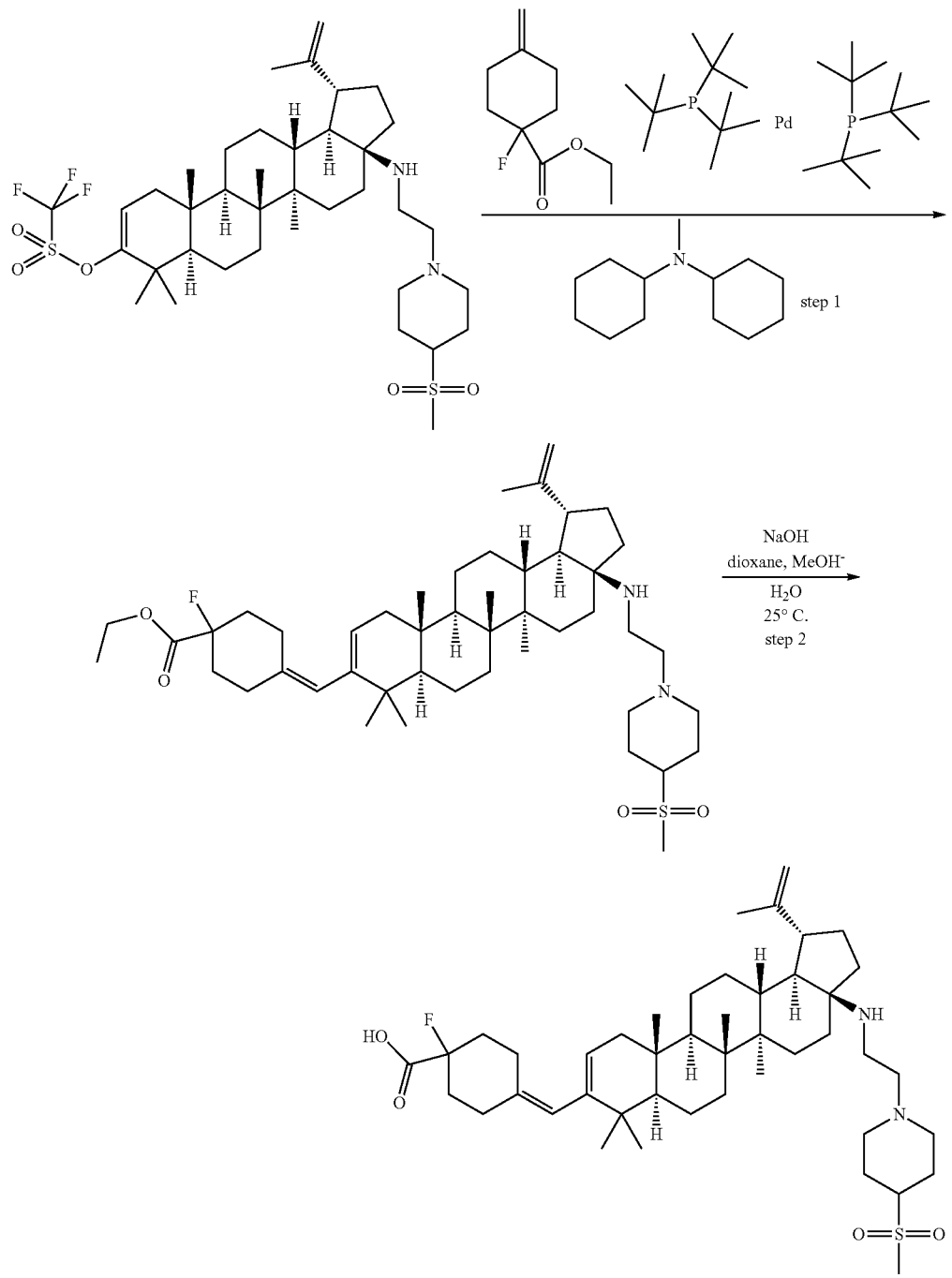
Example B3

Step 1. Preparation of ethyl 1-fluoro-4-(((1R,3aS, 5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)methylene) cyclohexanecarboxylate

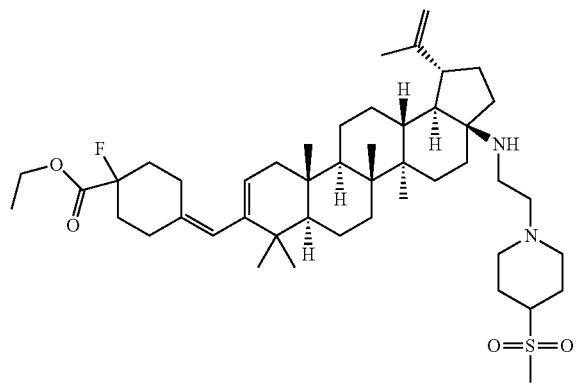

The mixture of (1R,3aS,5aR,5bR,7aR,11aR,11bR,13aR, 13bR)-5a,5b,8,8,11a-pentamethyl-3a-((2-(4-(methylsulfonyl)piperidin-1-yl)ethyl)amino)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yltrifluoromethanesulfonate (106 mg, 0.142 mmol), ethyl 1-fluoro-4-methylenecyclohexanecarboxylate (26.4 mg, 0.142 mmol) (prepared as described below) and N-cyclohexyl-N-methylcyclohexanamine (0.036 mL, 0.170 mmol) in dioxane (1 mL) was placed in a sealable pressure tube and $N_2$ was bubbled through the solution for 10 min. Bis(tri-tertbutylphosphine) Palladium(0) (0.725 mg, 1.419 μmol) was added to the reaction mixture and the tube was heated to 120° C. for 12 h. After cooling down to rt, the reaction mixture was diluted with diethyl ether and filtered. The filtrate was concentrated and partitioned over a silica gel flash column (12 g; eluted with ethyl acetate gradient in hexane from 0 to 50%) to give the title compound as a white solid. (93 mg, 84.0%). MS: m/e 783.6 (M+H)+, 3.088 min (method 2). $^1$H NMR (400 MHz, CHLOROFORM-d) δ 5.70-5.34 (m, 1H), 5.20 (m, 1H), 4.72 (s, 1H), 4.59 (s, 1H), 4.30-4.20 (m, 2H), 3.21-3.03 (m, 1H), 2.86-2.81 (m, 3H), 2.77-2.39 (m, 9H), 2.20-1.73 (m, 17H), 1.69 (s, 3H), 1.64-1.16 (m, 20H), 1.10-1.04 (m, 6H), 1.01-0.93 (m, 6H), 0.91-0.81 (m, 3H). $^{19}$F NMR (376 MHz, CHLOROFORM-d) δ −162.60-166.81 (m, 1F).

Step 2

1-fluoro-4-(((1R,3aS,5aR,5bR,7aR,11aS,11bR,13aR, 13bR)-5a,5b,8,8,11a-pentamethyl-3a-((2-(4-(methylsulfonyl)piperidin-1-yl)ethyl)amino)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)methylene) cyclohexanecarboxylic acid was prepared following the method described above for the preparation of 1-((tert-butoxycarbonyl)amino)-2-((E)-2-((1R,3aS,5aR,5bR,7aR, 11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)vinyl) cyclopropanecarboxylic acid, using ethyl 1-fluoro-4-(((1R, 3aS,5aR,5bR,7aR,11aS,11bR,13aR,13bR)-5a,5b,8,8,11a-pentamethyl-3a-((2-(4-(methylsulfonyl)piperidin-1-yl) ethyl)amino)-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)methylene)cyclohexanecarboxylate as the reactant in step 2. The reaction crude was purified by prep HPLC (method 4) to afford the title compound as a mixture of isomers in 20.7% of yield. MS: m/e 755.5 (M+H)+, 2.610 min (method 4). $^1$H NMR (400 MHz, METHANOL-$d_4$) δ 5.95-5.35 (m, 1H), 5.32-5.12 (m, 1H), 4.79 (br. s., 1H), 4.71 (s, 1H), 3.25-3.04 (m, 5H), 2.96 (s, 3H), 2.90-1.81 (m, 24H), 1.76 (s, 3H), 1.73-1.27 (m, 15H), 1.22 (br. s., 3H), 1.13-1.08 (m, 3H), 1.07-0.91 (m, 6H), 0.90-0.83 (m, 3H); $^{19}$F NMR (376 MHz, METHANOL-$d_4$) δ −154.27-167.89 (m, 1F).

Preparation of ethyl 1-fluoro-4-methylenecyclohexanecarboxylate

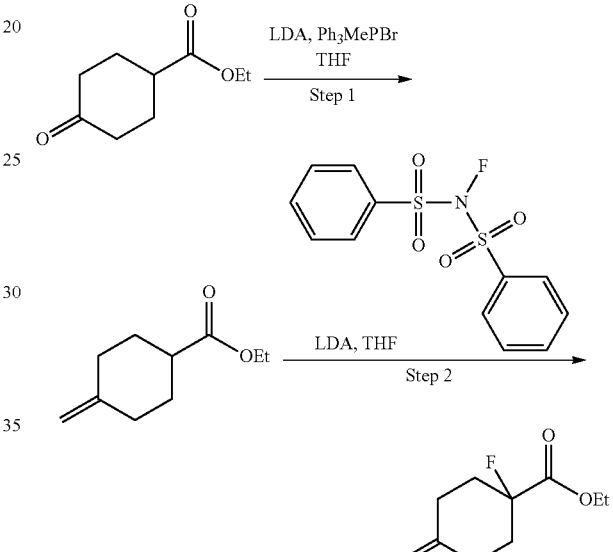

Step 1

Preparation of ethyl 4-methylenecyclohexanecarboxylate
N-butyllithium (21 mL, 52.5 mmol) was added dropwise to a solution of diisopropylamine (7.54 mL, 52.9 mmol) in THF (40 mL) at −78° C. over a period of 10 min. The resulted solution was stirred in an ice bath for 20 min. The above LDA solution was canulated into a suspension of methyltriphenylphosphonium bromide (19 g, 53.2 mmol) in THF (100 mL) in ice bath and the resulted mixture was stirred in the ice bath for 40 min. A solution of ethyl 4-oxocyclohexanecarboxylate (7.5 g, 44.1 mmol) in THF (20 mL) was added dropwise to this mixture. The reaction mixture was stirred for 18 h and diluted with hexane. The solid was filtered off and the filtrate was concentrated to afford a liquid. This crude product was plugged through silica gel pad (~2", EtOAc/hexane: 0 to 10%) to yield the title compound as a clear liquid (5.0 g, 68.8% yield). $^1$H NMR (400 MHz, CHLOROFORM-d) δ 4.76-4.60 (m, 2H), 4.20-4.08 (m, 2H), 2.45 (tt, J=11.1, 3.6 Hz, 1H), 2.35 (dt, J=13.5, 3.5 Hz, 2H), 2.14-1.96 (m, 4H), 1.67-1.52 (m, 2H), 1.30-1.22 (m, 3H)

Step 2

N-butyllithium (8.2 mL, 13.12 mmol) was added dropwise to a solution of diisopropylamine (2.1 mL, 14.73 mmol) in THF (10 mL) at −78° C. over a period of 10 min. The resulted solution was stirred in ice bath for 20 min. The resulting LDA solution was cooled to −78° C.

A solution of ethyl 4-methylenecyclohexanecarboxylate (2 g, 11.89 mmol) in THF (5 mL) was cooled at −78° C. and then added over a period of 5 min to the LDA solution. The resulted reaction mixture was stirred at −78° C. for 0.5 h. Then a solution of N-fluorobenzenesulfonamide (4.2 g, 13.32 mmol) in THF (25 mL) was added dropwise over a period of 5 min. The reaction mixture was stirred in the cool bath and allowed to slowly reach rt. After 18 h, it was diluted with EtOAc, washed with a saturated aqueous solution of NH$_4$Cl (2×), water and brine. The organic layer was dried over MgSO$_4$, concentrated and purified on a 25 g silica gel cartridge to afford the product as a liquid (1.97 g, 81% yield). $^1$H NMR (400 MHz, CHLOROFORM-d) δ 4.74 (t, J=1.6 Hz, 2H), 4.25 (q, J=7.2 Hz, 2H), 2.51-2.35 (m, 2H), 2.31-2.22 (m, 2H), 2.18-2.06 (m, 2H), 2.05-1.80 (m, 2H), 1.37-1.24 (m, 3H).

Example B4

Preparation of 3-((((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclobutanecarboxylic acid

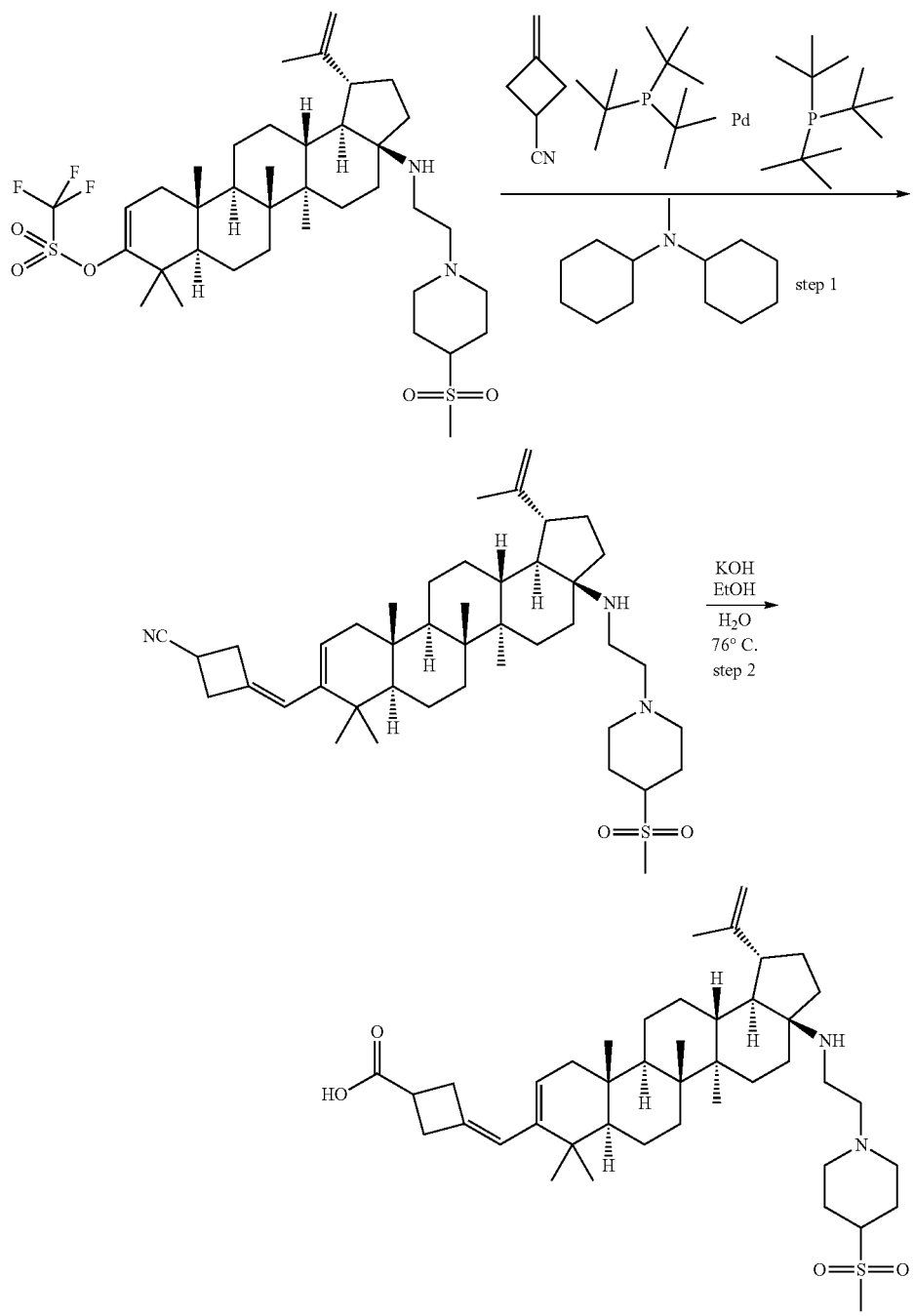

Example B4

Step 1. Preparation of 3-(((1R,3aS,5aR,5bR,7aR, 11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)methylene) cyclobutanecarbonitrile

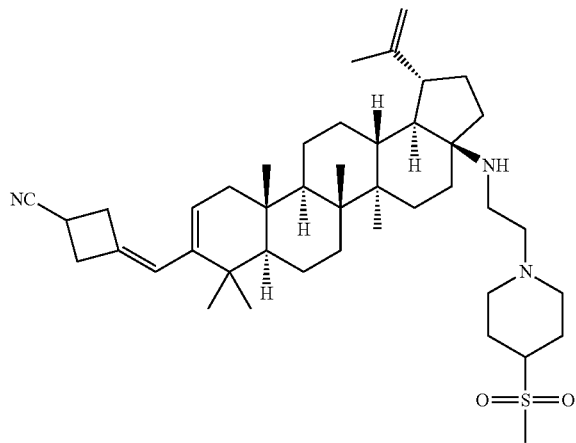

A mixture of (1R,3aS,5aR,5bR,7aR,11aR,11bR,13aR, 13bR)-5a,5b,8,8,11a-pentamethyl-3a-((2-(4-(methylsulfonyl)piperidin-1-yl)ethyl)amino)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yltrifluoromethanesulfonate (60 mg, 0.080 mmol), 3-methylenecyclobutanecarbonitrile (7.48 mg, 0.080 mmol) and N-cyclohexyl-N-methylcyclohexanamine (0.021 mL, 0.096 mmol) in dioxane (1 mL) was placed in a sealable tube and $N_2$ was bubbled through the solution for 10 min. Bis(tritertbutylphosphine) Palladium(0) (1.231 mg, 2.410 μmol) was added to the reaction mixture and the tube was heat to 120° C. for 12 h. After cooling down to rt, the reaction was diluted with diethyl ether and filtered. The filtrate was concentrated and purified using a silica gel flash column (12 g; eluted with ethyl acetate gradient in hexane from 0 to 50%) to give the title compound as a white solid. (30 mg, 54.1%). MS: m/e 690.5 (M+H)$^+$, 2.618 min (method 4). $^1$H NMR (400 MHz, CHLOROFORM-d) δ 5.81 (br. s., 1H), 5.27 (d, J=5.5 Hz, 1H), 4.72 (d, J=1.8 Hz, 1H), 4.59 (d, J=0.8 Hz, 1H), 3.28-2.98 (m, 5H), 2.91-2.76 (m, 4H), 2.72-2.52 (m, 4H), 2.50-2.36 (m, 2H), 2.32-1.74 (m, 13H), 1.70 (s, 3H), 1.68-1.12 (m, 16H), 1.09 (s, 3H), 1.04-0.99 (m, 3H), 0.96 (m, 3H), 0.92-0.79 (m, 6H).

Step 2

To a solution of 3-(((1R,3aS,5aR,5bR,7aR,11aS,11bR, 13aR,13bR)-5a,5b,8,8,11a-pentamethyl-3a-((2-(4-(methylsulfonyl)piperidin-1-yl)ethyl)amino)-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)methylene) cyclobutanecarbonitrile (30 mg, 0.043 mmol) in ethanol (2 mL) was added potassium hydroxide (1 mL, 0.043 mmol). A white precipitate was formed. The mixture became clear after warming up to 76° C. The reaction solution was stirred at 76° C. for 7 h. The crude product was purified without further work up by prep HPLC (method 4) to give 3-(((1R,3aS,5aR, 5bR,7aR,11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)methylene)cyclobutanecarboxylic acid as a white solid (9 mg, 29.2%). MS: m/e 709.55 (M+H)$^+$, 2.54 min (method 4). $^1$H NMR (400 MHz, METHANOL-d$_4$) δ 5.72 (br. s., 1H), 5.38 (d, J=5.5 Hz, 1H), 4.78 (s, 1H), 4.68 (s, 1H), 3.28-2.75 (m, 14H), 2.96 (s, 3H), 2.65-2.52 (m, 1H), 2.42-2.27 (m, 1H), 2.23-1.80 (m, 11H), 1.75 (s, 3H), 1.69-1.27 (m, 14H), 1.22 (s, 3H), 1.10 (br. s., 3H), 1.01 (br. s., 3H), 0.96-0.93 (m, 3H), 0.90-0.87 (m, 3H).

Example B5

Preparation of 5-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)penta-2,4-dienoic acid

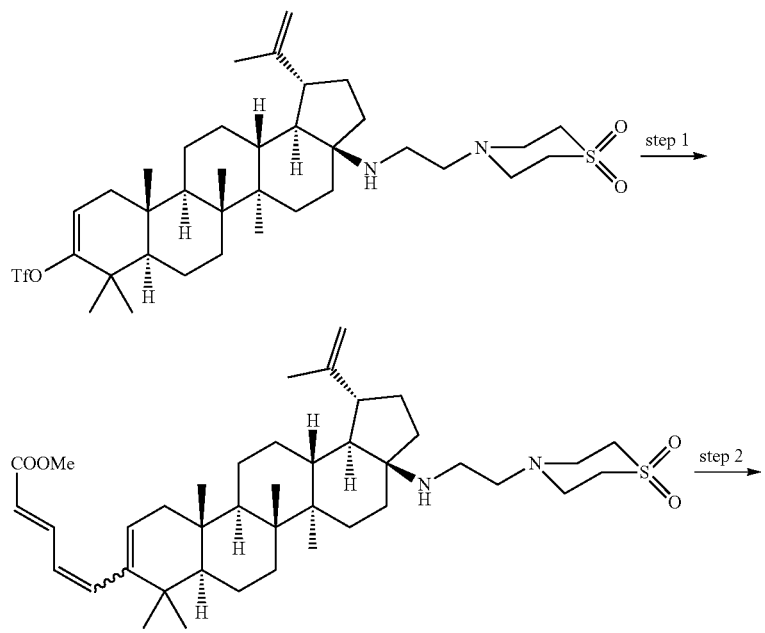

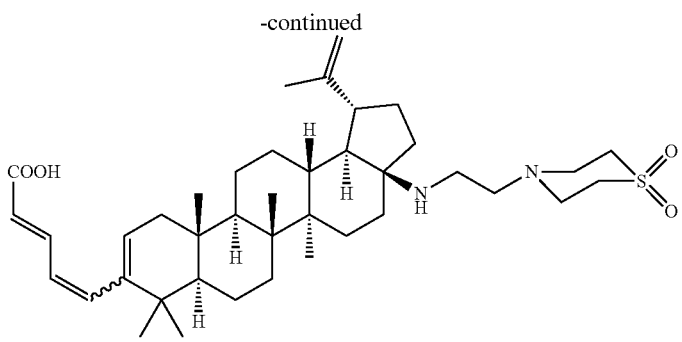

Example B5

Step 1: Preparation of methyl 5-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)penta-2,4-dienoate

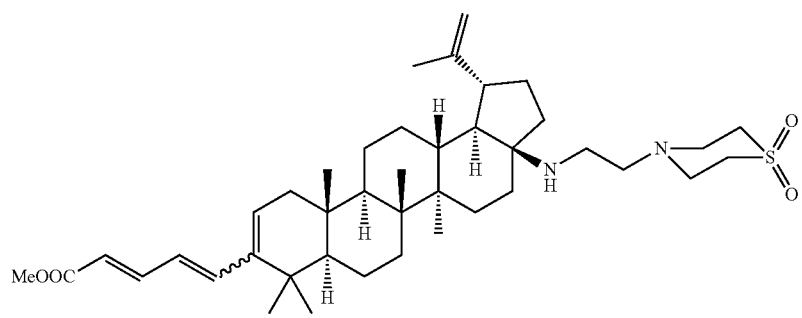

The title compound was prepared following the procedure described in step 1 of the preparation of 1-fluoro-4-(((1R,3aS, 5aR,5bR,7aR,11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)methylene)cyclohexanecarboxylic acid using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yltrifluoromethanesulfonate and (E)-methyl penta-2,4-dienoate as the reactants. The crude material was used in the next step without further purification. MS: m/e 681.5 (M+H)+, 2.52 min (method 5).

Step 2

5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)penta-2,4-dienoic acid was prepared following the procedure described in step 2 of the preparation of 1-fluoro-4-(((1R,3aS,5aR,5bR,7aR,11aS,11bR,13aR, 13bR)-5a,5b,8,8,11a-pentamethyl-3a-((2-(4-(methylsulfonyl)piperidin-1-yl)ethyl)amino)-1-(prop-1-en-2-yl)-2,3,3a, 4,5,5a,5b, 6,7,7a,8,11,11a,11b,12,13,13a,13b-octadecahydro-1H-cyclopenta[a]chrysen-9-yl)methylene) cyclohexanecarboxylic acid using the corresponding crude product from step 1 as the reactant. The title compound was obtained as a mixture of 2E,4E- and 2E,4Z-2,4-dienoic acid isomers (solid, 11%). MS: m/e 667.5 (M+H)+, 2.41 min (method 5). For 2E,4E isomer, 1H NMR (400 MHz, CHLOROFORM-d) δ 7.40-7.26 (m, 1H), 6.54 (d, J=15.1 Hz, 1H), 6.18 (dd, J=15.3, 11.0 Hz, 1H), 5.88 (d, J=15.1 Hz, 1H), 5.65 (s., 1H), 4.80 (s, 1H), 4.66 (s, 1H), 3.22-2.63 (m, 12H), 2.21-0.81 (m, 23H), 1.71 (s, 3H), 1.13 (s, 3H), 1.01 (s, 3H), 0.99 (s, 3H), 0.91 (s, 3H), 0.71 (s, 3H).

Example B6

Preparation of 5-((1R,3aS,5aR,5bR,7aR,11aS,11bR, 13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)penta-2,4-dienoic acid

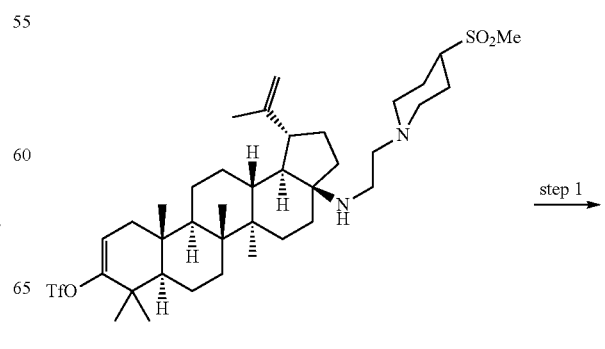

step 1

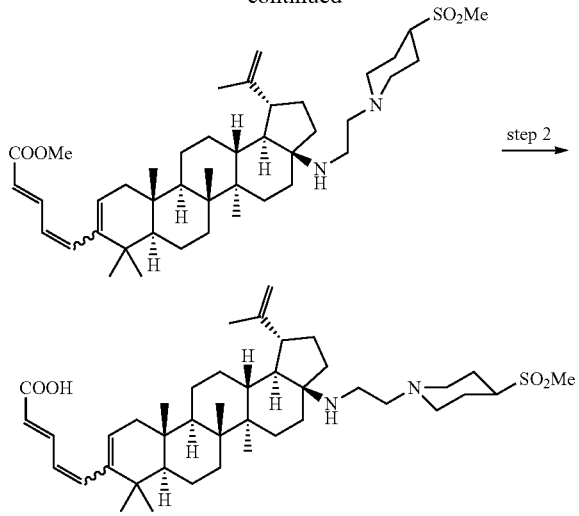

Example B6

Step 1: Preparation of methyl 5-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)penta-2,4-dienoate

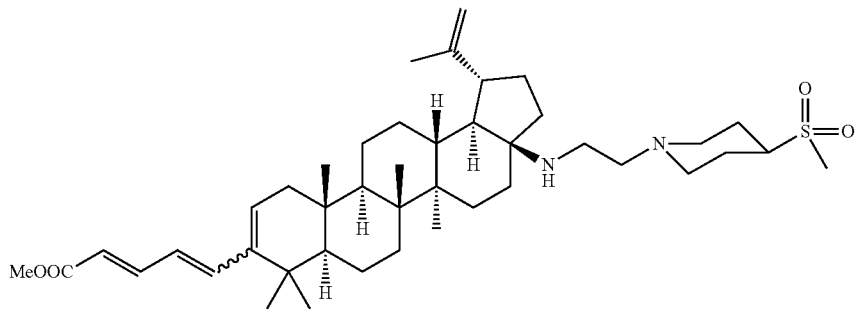

The title compound was prepared following the procedure described in step 1 of the preparation of 1-fluoro-4-(((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclohexanecarboxylic acid using (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yltrifluoromethanesulfonate and (E)-methyl penta-2,4-dienoate as the reactants. The crude material was used in next step without purification. MS: m/e 709.5 (M+H)$^+$, 2.55 min (method 5).

Step 2

5-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)penta-2,4-dienoic acid was prepared was prepared following the procedure described in step 2 of the preparation of 1-fluoro-4-(((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)methylene)cyclohexanecarboxylic acid using the corresponding crude product from step 1 as the reactant. The title compound was obtained as a mixture of 2E,4E- and 2E,4Z-2,4-dienoic acid isomers (solid, 39%). MS: m/e 695.5 (M+H)$^+$, 2.38 min (method 5). For 2E,4E isomer, $^1$H NMR (400 MHz, CHLOROFORM-d) δ 7.35-7.24 (m, 1H), 6.50 (d, J=15.3 Hz, 1H), 6.16 (dd, J=15.2, 11.2 Hz, 1H), 5.89 (d, J=15.1 Hz, 1H), 5.60 (s, 1H), 4.82 (s, 1H), 4.66 (s, 1H), 3.38-2.52 (m, 12H), 2.87 (s, 3H), 2.33-0.83 (m, 24H), 1.71 (s, 3H), 1.13 (s, 3H), 0.99 (s, 3H), 0.97 (s, 3H), 0.89 (s, 3H), 0.68 (s, 3H).

Biology Data for the Examples

"μM" means micromolar;
"mL" means milliliter;
"μl" means microliter;
"mg" means milligram;
"μg" means microgram;

The materials and experimental procedures used to obtain the results reported in Table 1 are described below.

HIV Cell Culture Assay—MT-2 cells and 293T cells were obtained from the NIH AIDS Research and Reference Reagent Program. MT-2 cells were propagated in RPMI 1640 media supplemented with 10% heat inactivated fetal bovine serum, 100 g/ml penicillin G and up to 100 units/ml streptomycin. The 293T cells were propagated in DMEM media supplemented with 10% heat inactivated fetal bovine serum (FBS), 100 units/ml penicillin G and 100 μg/ml streptomycin. The proviral DNA clone of NL$_{4-3}$ was obtained from the NIH AIDS Research and Reference Reagent Program. A recombinant NL$_{4-3}$ virus, in which a section of the nef gene from NL4-3 was replaced with the *Renilla* luciferase gene, was used as a reference virus. In addition, residue Gag P373 was converted to P373S. Briefly, the recombinant virus was prepared by transfection of the altered proviral clone of NL$_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty

(50) μL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$ data for the compounds is shown in Table 1.

TABLE 1

| Example # | Structure | $EC_{50}$ μM |
|---|---|---|
| 1 | 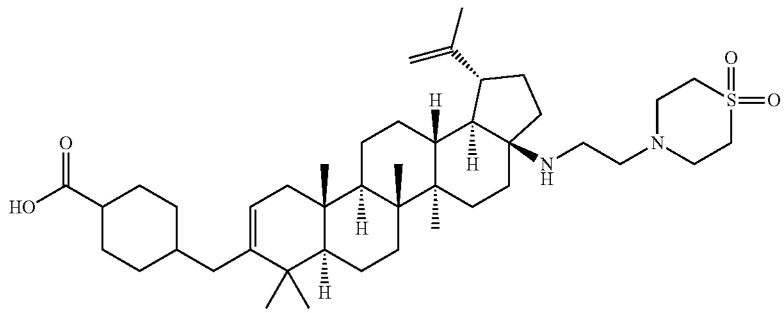 | 2.96E−03 |
| 2 | Isomer 1 | 2.00E−03 |
| 3 | Isomer 2 | 1.72E−03 |
| 4 | 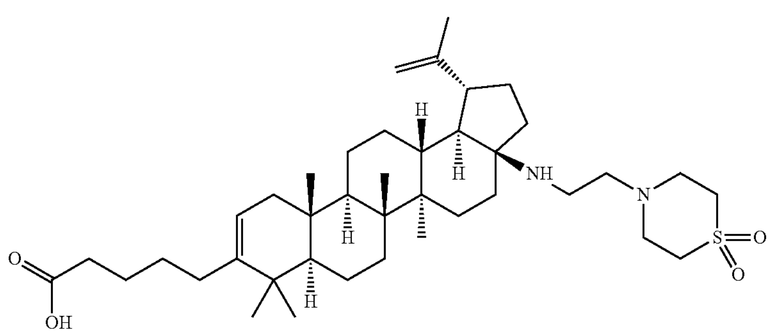 | 2.27E−03 |

TABLE 1-continued

| Example # | Structure | EC$_{50}$ μM |
|---|---|---|
| 5 | 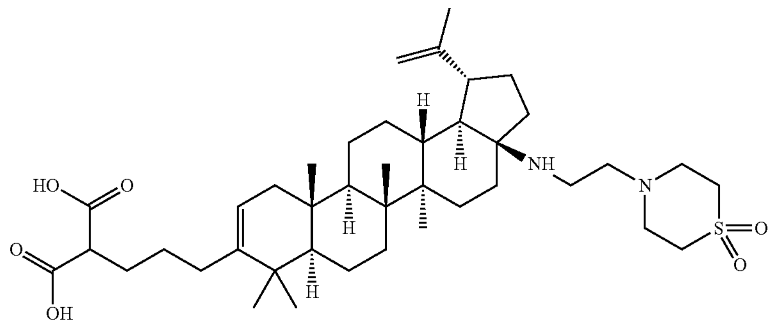 | 0.31 |
| 6 | 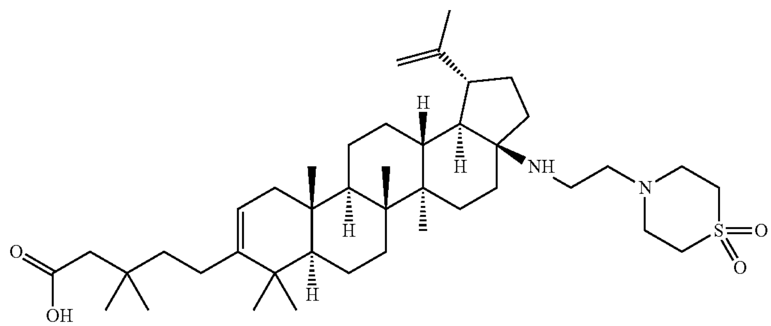 | 1.38E−03 |
| 7 | 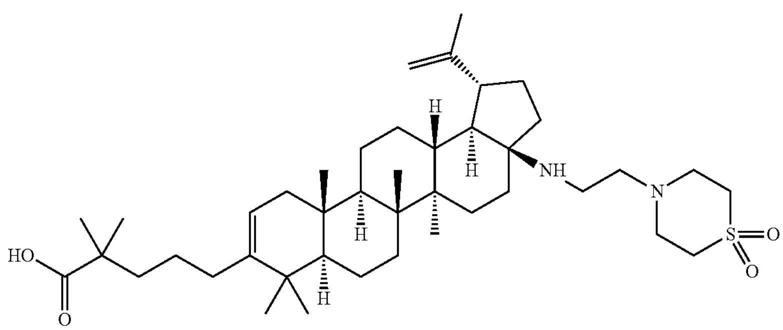 | 5.3E−03 |
| 8 | 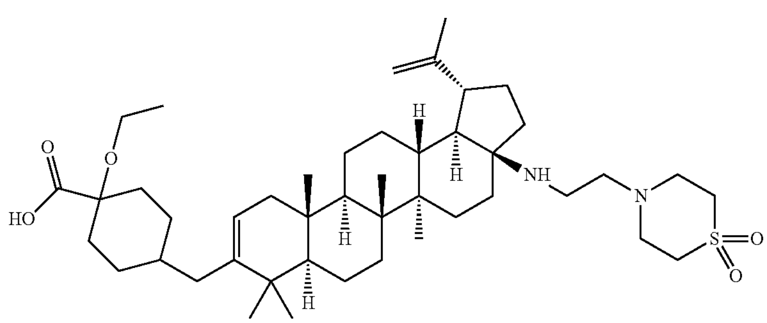 | 4.2E−03 |

TABLE 1-continued

| Example # | Structure | EC$_{50}$ µM |
|---|---|---|
| 9 | 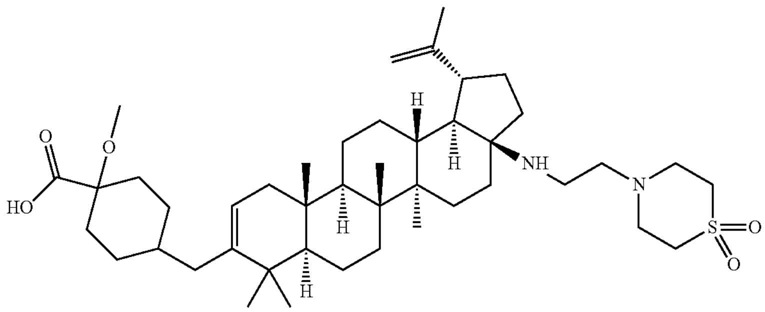 | 3.7E-03 |
| 10 | 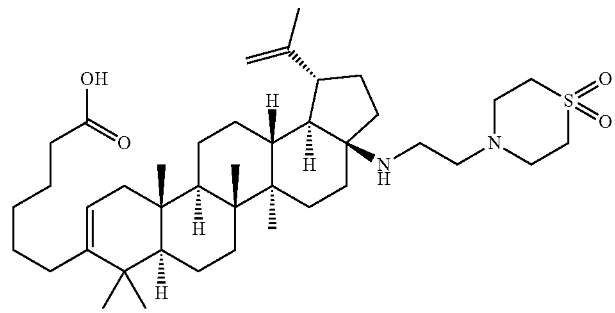 | 3.1E-03 |
| 11 | 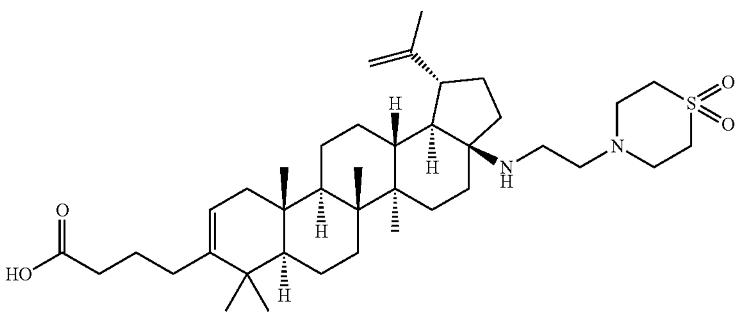 | 0.01 |
| 12 | 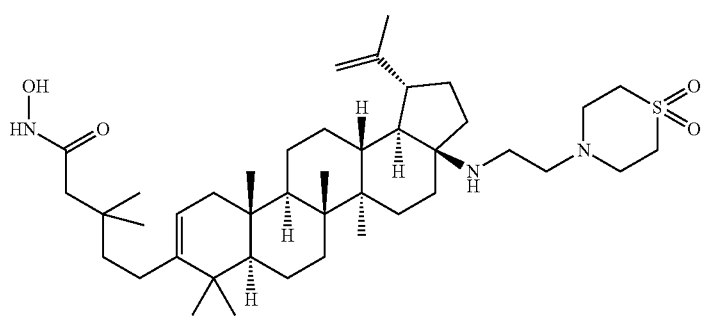 | 2.0E-03 |
| 13 | 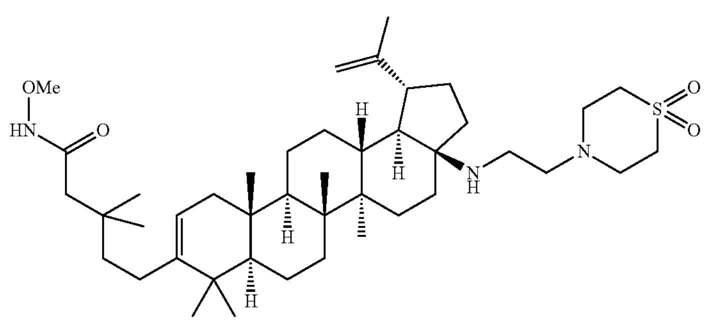 | 0.03 |

TABLE 1-continued

| Example # | Structure | EC$_{50}$ μM |
|---|---|---|
| 14 | 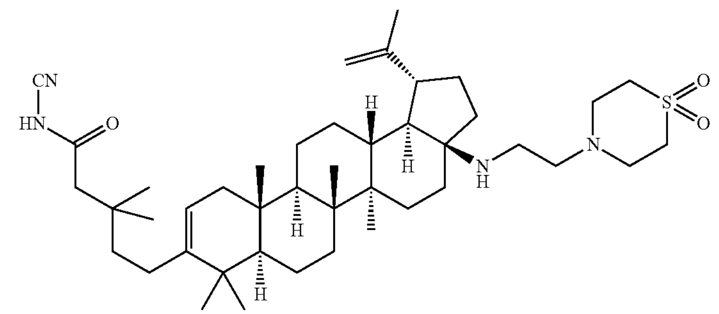 | 4.7E−03 |
| 15 | 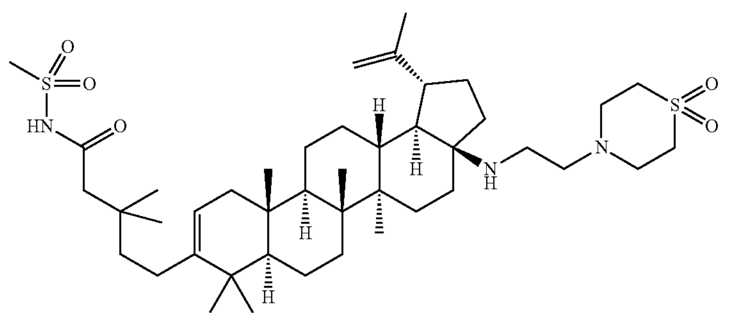 | 1.6E−03 |
| 16 | 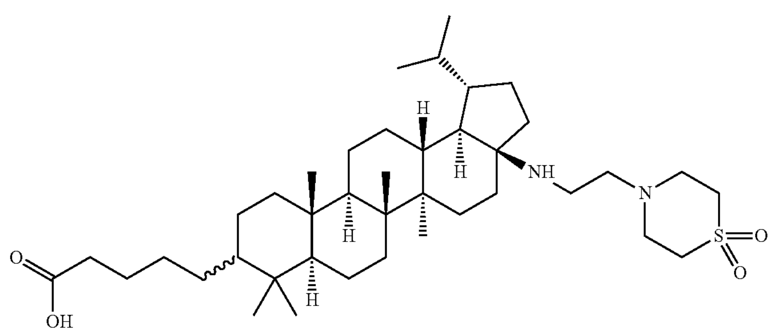 | 1.0E−03 |
| 17 | 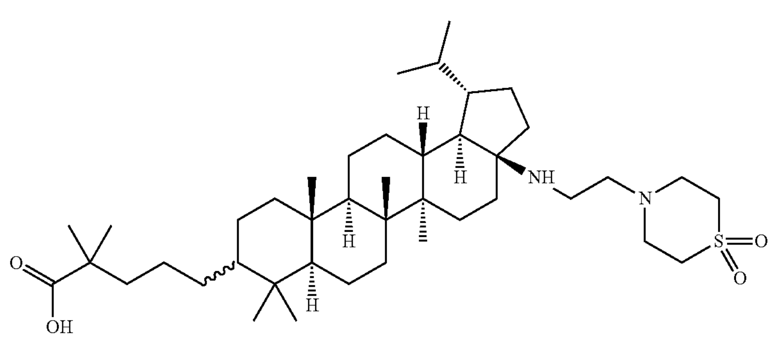 | 7.3E−03 |

TABLE 1-continued
| Example # | Structure | EC$_{50}$ µM |
|---|---|---|
| 18 | 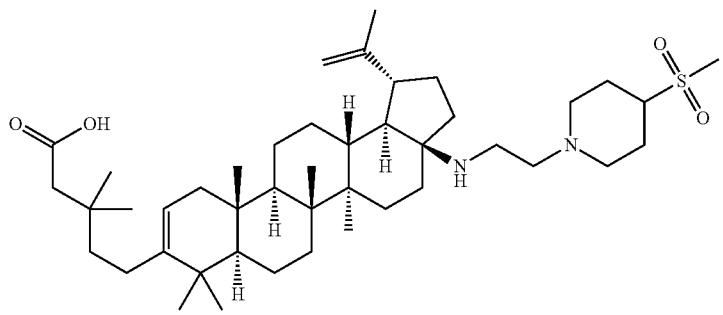 | 1.1E−03 |
| 19 | 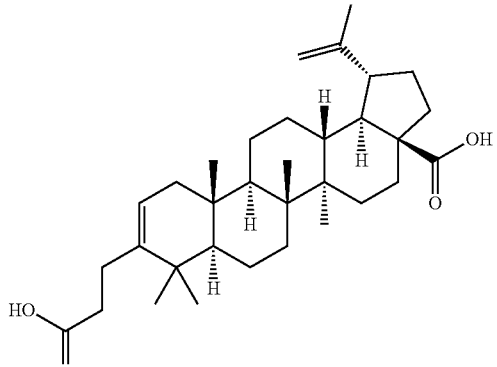 | 0.47 |
| A1 | 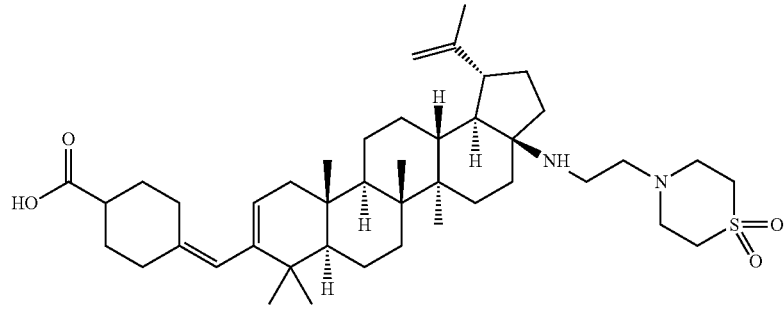 | 3.55E−03 |
| B1 | 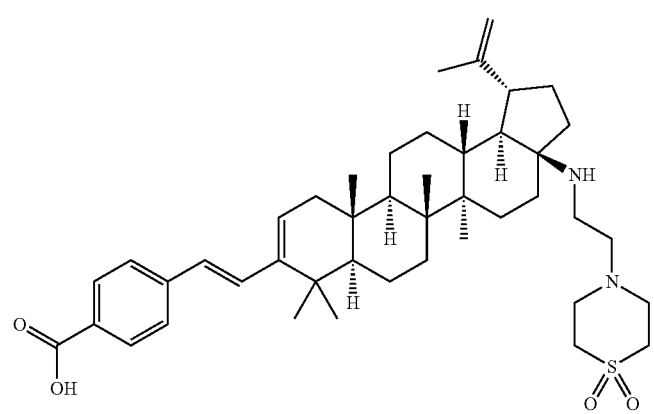 | 0.01 |

TABLE 1-continued
| Example # | Structure | EC$_{50}$ μM |
|---|---|---|
| B2 | 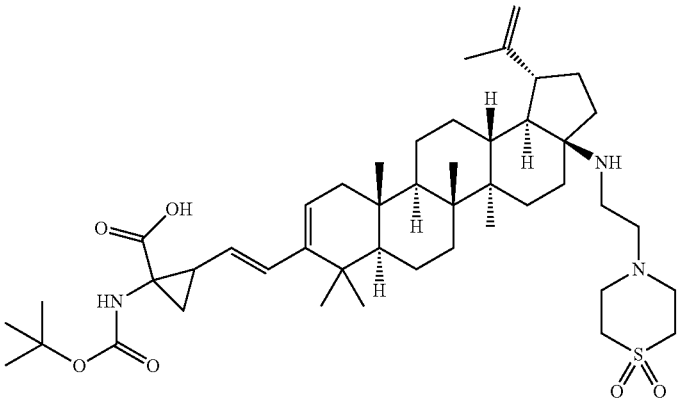 | 0.04 |
| B3 | 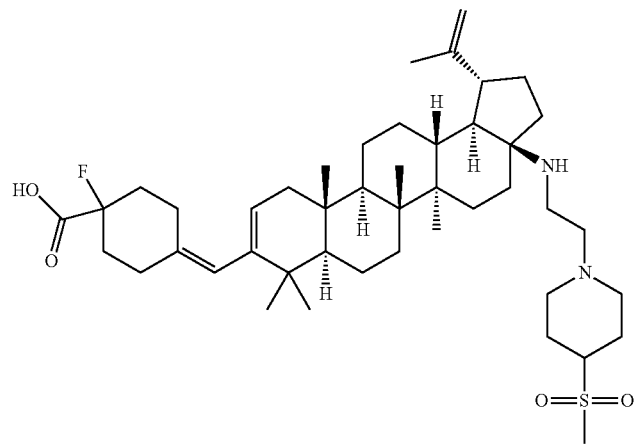 | 4.49E−03 |
| B4 | 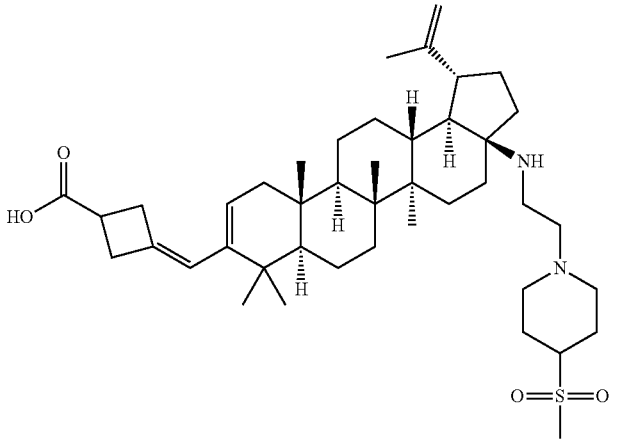 | 6.00E−04 |

| Example # | Structure | EC$_{50}$ µM |
|---|---|---|
| B5 | 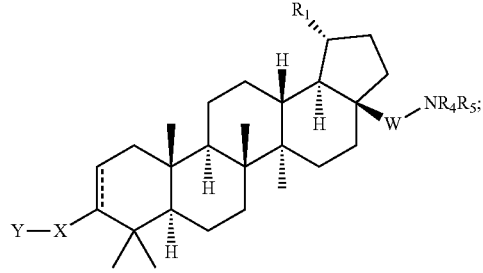 | |
| B6 | 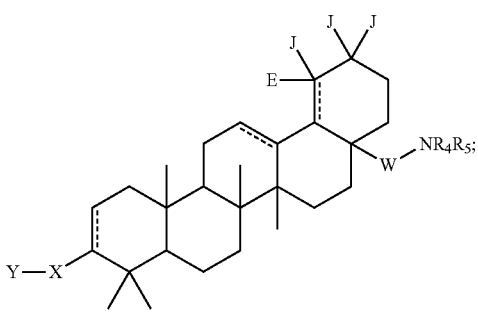 | |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound which is selected from the group of:

a compound of Formula I

Formula I a compound of Formula II

Formula II

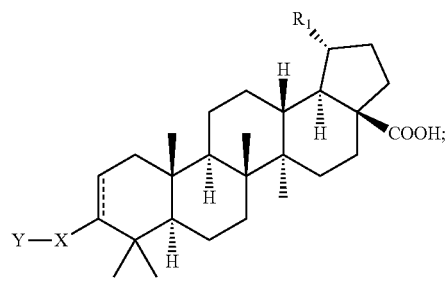

a compound of Formula III

Formula III and a compound of formula IV

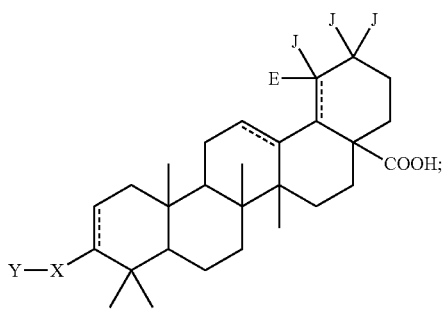

Formula IV wherein $R_1$ is isopropenyl or isopropyl;
J and E are independently —H or —$CH_3$, and E is absent when the double bond is present;
X is selected from the group of —$C_{0-10}$ alkyl, —$C_{2-10}$ alkenyl, —$C_{4-10}$ alkadienyl,

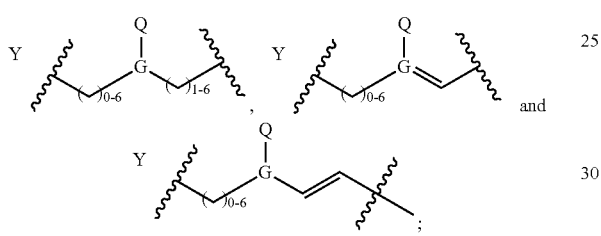

wherein G is selected from the group of $C_{3-9}$ cycloalkyl, aryl, heteroaryl, fused bicycle and

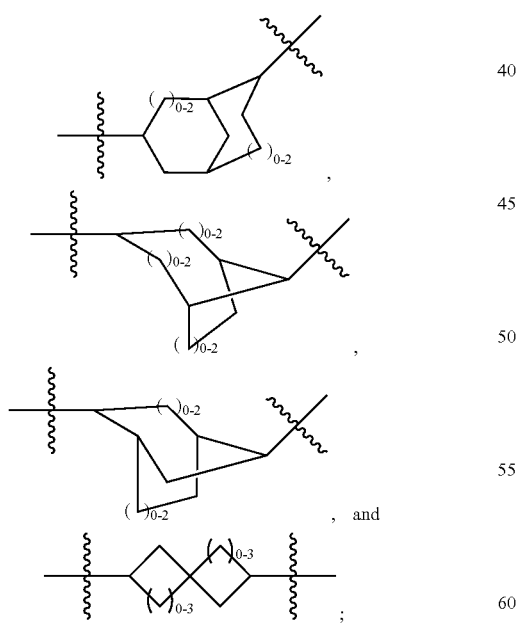

wherein X is optionally further substituted with A, wherein A is at least one member selected from the group of -halo, —$OR_2$, —$C_{1-6}$ alkyl, —$C_{1-6}$ alkylsubstituted alkyl, —$C_{3-9}$ cycloalkyl, —$C_{1-6}$ alkyl-$Q_0$, —$NR_2R_2$, —$NHCOOR_3$, —$COOR_2$ and —$CONR_2R_2$;

Q and $Q_0$ are selected from the group of -halo, —$OR_2$, —$C_{1-6}$ alkyl, —$C_{1-6}$ alkylsubstituted alkyl, —$C_{3-9}$ cycloalkyl, —$NR_2R_2$, —$NHCOOR_3$, —$COOR_2$ and —$CONR_2R_2$;

$R_2$ is —H, —$C_{1-6}$ alkyl, -alkylsubstituted $C_{1-6}$ alkyl or -arylsubstituted $C_{1-6}$ alkyl;

Y is selected from the group of —$COOR_2$, —C(O)$NR_2SO_2R_3$, —C(O)$NHSO_2NR_2R_2$, —$NR_2SO_2R_3$, —$SO_2NR_2R_2$, —$SO_2NR_2C(O)R_3$, -tetrazole, —C(O)NHCN and —C(O)$NHOR_2$;

W is absent, —$CH_2$ or —CO;

$R_3$ is —$C_{1-6}$ alkyl, -alkylsubstituted —$C_{1-6}$ alkyl, —$C_{3-6}$ cycloalkyl or $C_{1-6}$ alkyl-$C_{3-6}$ cycloalkyl;

$R_4$ is selected from the group of —H, —$C_{1-6}$ alkyl, —$C_{1-6}$ alkyl-$C(OR_3)_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, —$SO_2NR_2R_2$,

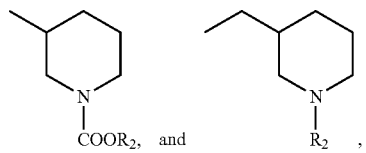

with the proviso that $R_4$ or $R_5$ is not —$COR_6$ or —$COCOR_6$ when W is CO;

wherein $Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;

with the proviso that only one of $R_4$ or $R_5$ is selected from the group of —$COR_6$, —$COCOR_6$, —$SO_2R_7$ and —$SO_2NR_2R_2$;

or when W is absent or is $CH_2$, then $R_4$ and $R_5$ is taken together with the adjacent N to form

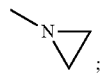

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substitutedalkyl-$Q_2$, —$C_{3-6}$ cycloalkyl-$Q_2$, aryl-$Q_2$, —$NR_{13}R_{14}$, and —$OR_{15}$;

wherein $Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —$C_{1-6}$ alkyl, —$C_{1-6}$ substituted alkyl, —$C_{3-6}$ cycloalkyl, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, and $R_8$ and $R_9$ is also independently selected from the group of

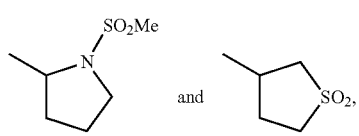 and 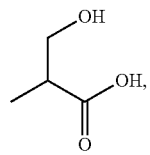

or $R_8$ and $R_9$ are taken together with the adjacent N to form a cycle selected from the group of:

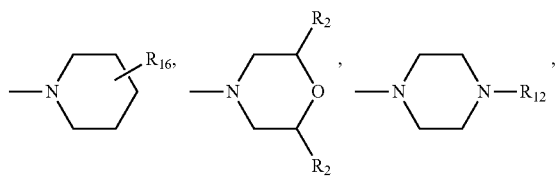

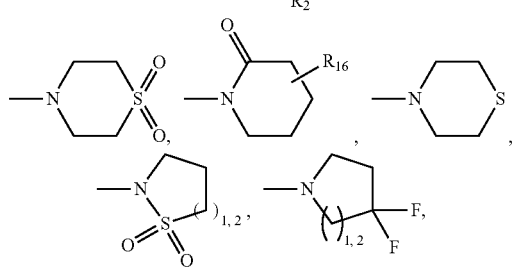

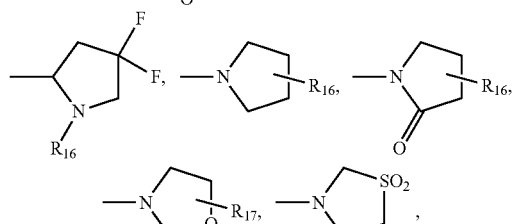

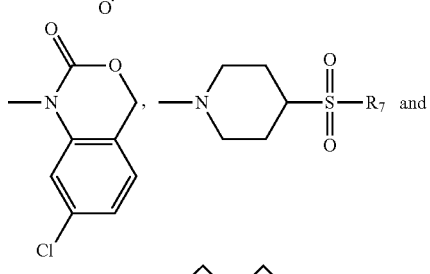

with the proviso that only one of $R_8$ or $R_9$ is —COOR$_3$;

$R_{10}$ and $R_{11}$ are independently selected from the group of —H, —C$_{1-6}$ alkyl, —C$_{1-6}$ substituted alkyl and —C$_{3-6}$ cycloalkyl, or $R_{10}$ and $R_{11}$ are taken together with the adjacent N to form the cycle

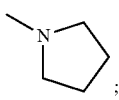;

$R_{12}$ is selected from the group of —C$_{1-6}$ alkyl, —C$_{1-6}$ alkyl-OH; —C$_{1-6}$ alkyl, —C$_{1-6}$ substituted alkyl,—C$_{3-6}$ cycloalkyl, —COR$_7$, —COONR$_{22}$R$_{23}$, —SOR$_7$, and —SONR$_{24}$R$_{25}$;

$R_{13}$ and $R_{14}$ are independently selected from the group of —H, —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$, C$_{1-6}$ substituted alkyl-Q$_3$ and

or $R_{13}$ and $R_{14}$ are taken together with the adjacent N to form a cycle selected from the group of:

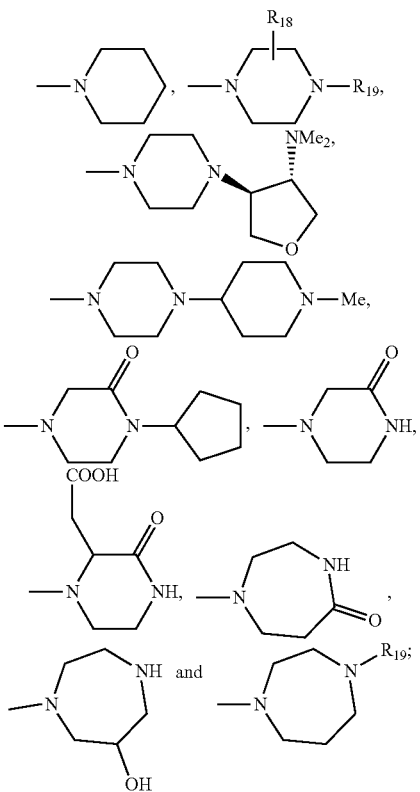

$Q_3$ is selected from the group of heteroaryl, substituted heteroaryl, —NR$_{20}$R$_{21}$, —CONR$_2$R$_2$, —COOR$_2$, —OR$_2$, and —SO$_2$R$_3$;

$R_{15}$ is selected from the group of —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$ and —C$_{1-6}$ substituted alkyl-Q$_3$;

$R_{16}$ is selected from the group of —H, —C$_{1-6}$ alkyl, —NR$_2$R$_2$, and —COOR$_3$;

$R_{17}$ is selected from the group of —H, —C$_{1-6}$ alkyl, —COOR$_3$, and aryl;

$R_{18}$ is selected from the group of —COOR$_2$ and —C$_{1-6}$ alkyl-COOR$_2$;

$R_{19}$ is selected from the group of —H, —C$_{1-6}$ alkyl, —C$_{1-6}$ alkyl-Q$_4$, —COR$_3$, —COOR$_3$, wherein Q$_4$ is selected from the group of —NR$_2$R$_2$ and —OR$_2$;

$R_{20}$ and $R_{21}$ are independently selected from the group of —H, —C$_{1-6}$ alkyl, —C$_{1-6}$ substituted alkyl, —C$_{1-6}$ substituted alkyl-OR$_2$, and —COR$_3$, or $R_{20}$ and $R_{21}$ are taken together with the adjacent N to form a cycle selected from the group of

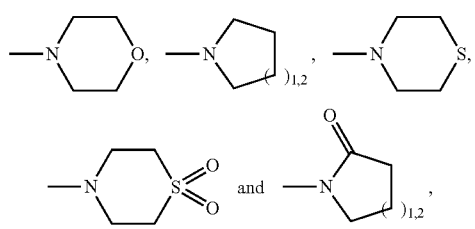

with the proviso that only one of $R_{20}$ or $R_{21}$ is —$COR_3$;

$R_{22}$ and $R_{23}$ are independently selected from the group of H, —$C_{1-6}$ alkyl, —$C_{1-6}$ substituted alkyl, and —$C_{1-6}$ cycloalkyl, or $R_{22}$ and $R_{23}$ are taken together with the adjacent N to form a cycle selected from the group of

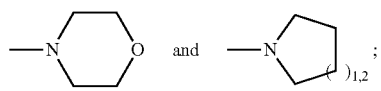

$R_{24}$ and $R_{25}$ are independently from the group of H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl; and $Q_5$ is selected from the group of halogen and $SO_2R_3$; and pharmaceutically acceptable salts thereof.

2. A compound of claim 1, wherein Y is —$COOR_2$.
3. A compound of claim 2, wherein Y is —COOH.
4. A compound of claim 1, wherein $R_1$ is isopropenyl.
5. A compound of claim 4, wherein W is absent.
6. A compound which is selected from the group of:

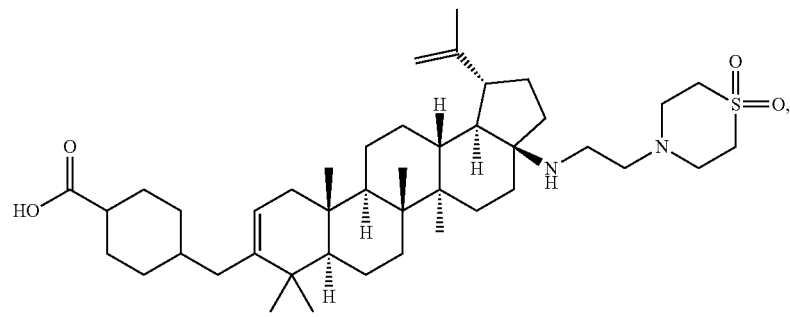

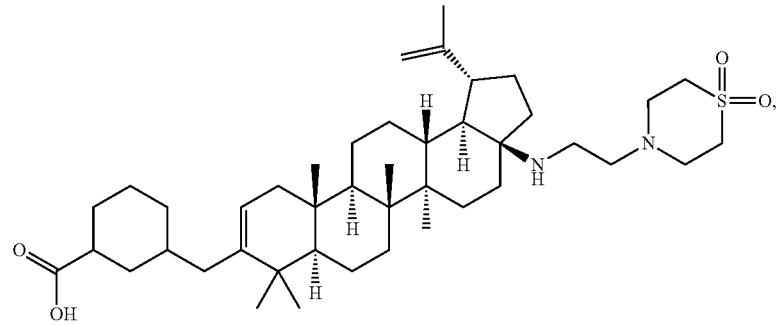

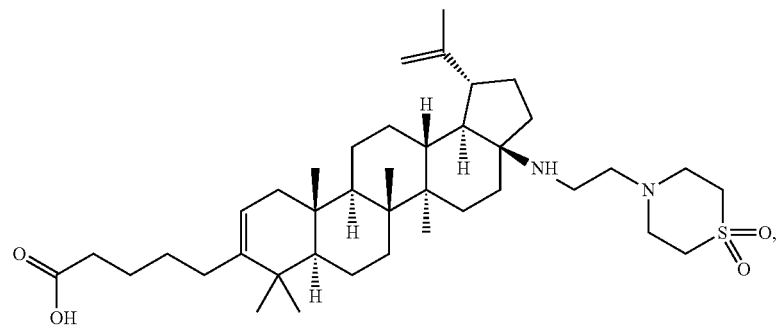

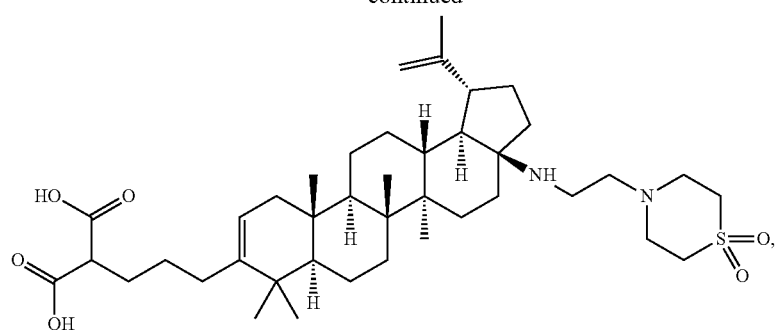
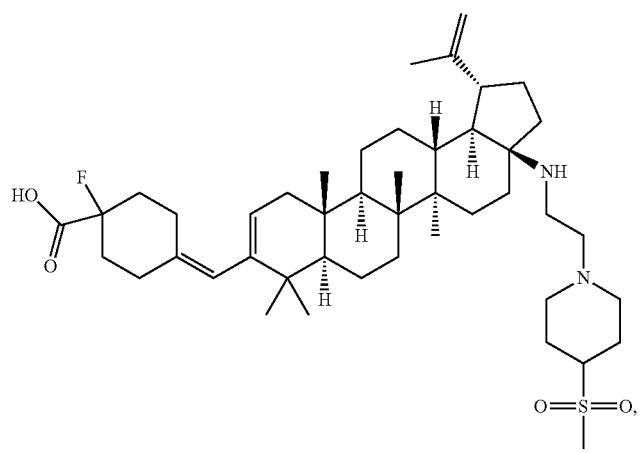
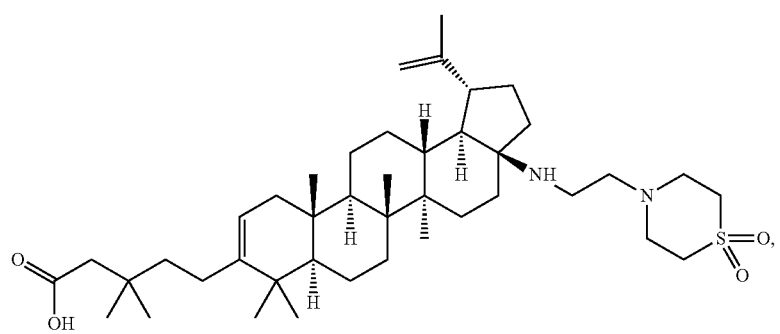
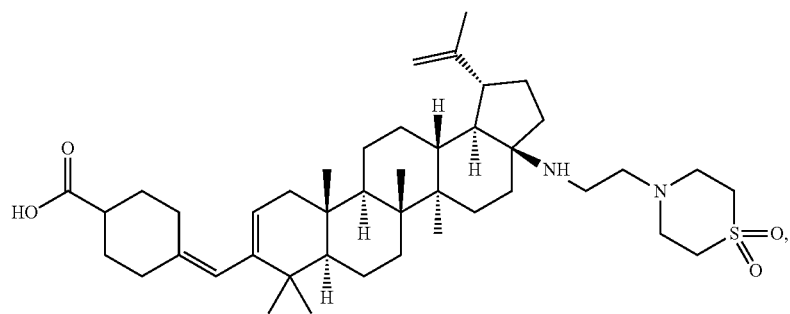

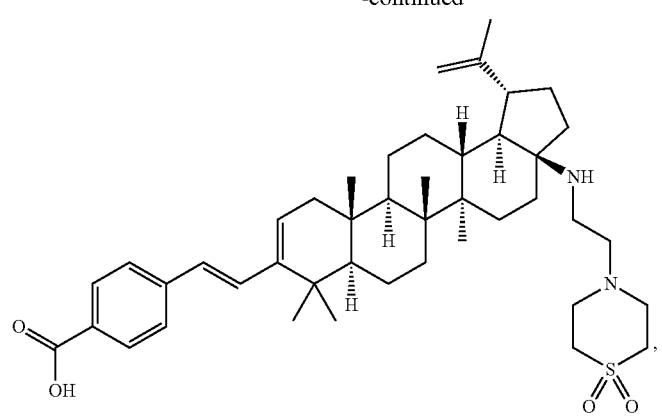
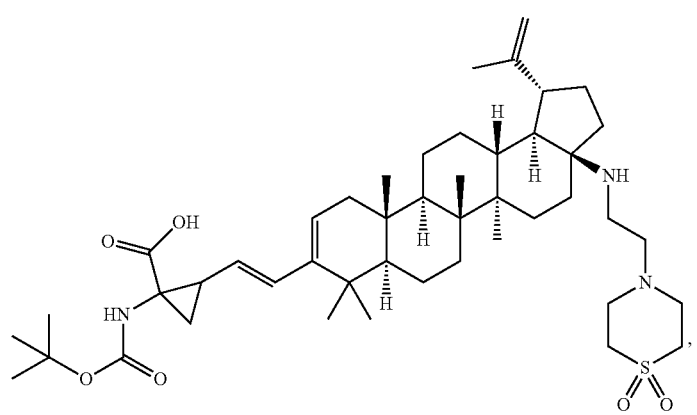
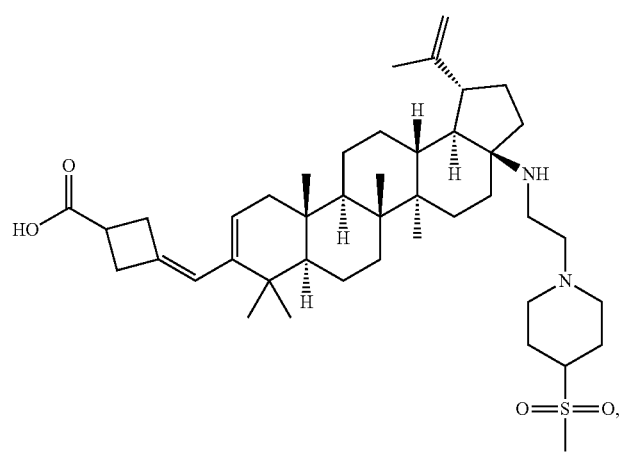
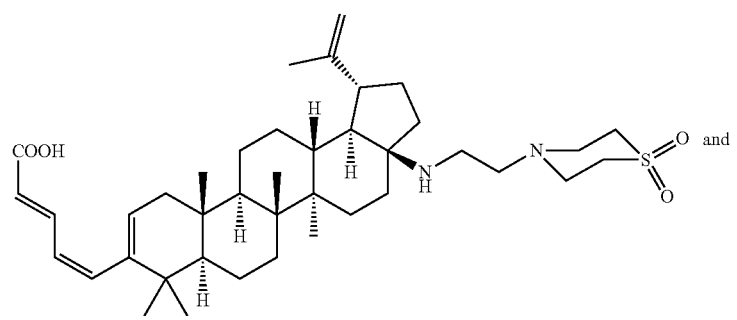

-continued

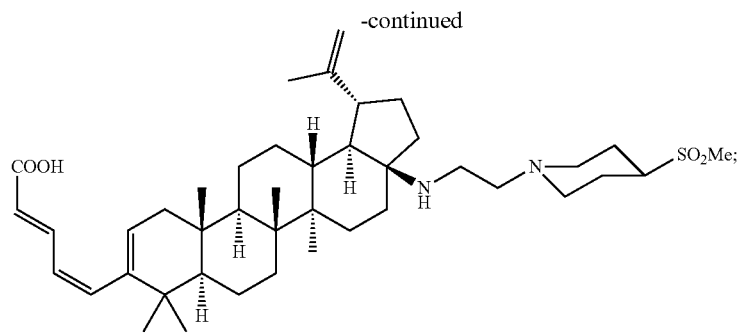

and pharmaceutically acceptable salts thereof.

7. A pharmaceutical composition which comprises an HIV ameliorating amount of one or more of the compounds as claimed in claim 1, together with one or more pharmaceutically acceptable carriers, excipients or diluents.

8. The pharmaceutical composition of claim 7, useful for treating infection by HIV, which additionally comprises an HIV ameliorating amount of an AIDS treatment agent selected from the group of: (a) an AIDS antiviral agent; (b) an anti-infective agent; (c) an immunomodulator; and (d) another HIV entry inhibitor.

9. A method for treating a mammal infected with the HIV virus comprising administering to said mammal an HIV ameliorating amount of a compound as claimed in claim 1, and one or more pharmaceutically acceptable carriers, excipients or diluents.

10. A pharmaceutical composition which comprises an HIV ameliorating amount of one or more of the compounds as claimed in claim 6, together with one or more pharmaceutically acceptable carriers, excipients or diluents.

11. The pharmaceutical composition of claim 10, useful for treating infection by HIV, which additionally comprises an HIV ameliorating amount of an AIDS treatment agent selected from the group of: (a) an AIDS antiviral agent; (b) an anti-infective agent; (c) an immunomodulator; and (d) another HIV entry inhibitor.

12. A method for treating a mammal infected with the HIV virus comprising administering to said mammal an HIV ameliorating amount of a compound as claimed in claim 6, and one or more pharmaceutically acceptable carriers, excipients or diluents.

13. A compound of claim 1, wherein said compound is a compound of Formula I.

\* \* \* \* \*